US006723744B2

(12) United States Patent
Aspnes et al.

(10) Patent No.: US 6,723,744 B2
(45) Date of Patent: Apr. 20, 2004

(54) INDOLE CARBOXYLIC ACIDS AS THYROID RECEPTOR LIGANDS

(75) Inventors: Gary E. Aspnes, Rockville, RI (US); Yuan-Ching P. Chiang, East Lyme, CT (US)

(73) Assignee: Pfizer, Inc., New York, NY (US)

(*) Notice: Subject to any disclaimer, the term of this patent is extended or adjusted under 35 U.S.C. 154(b) by 0 days.

(21) Appl. No.: 10/255,180

(22) Filed: Sep. 24, 2002

(65) Prior Publication Data

US 2003/0078289 A1 Apr. 24, 2003

Related U.S. Application Data

(60) Provisional application No. 60/325,385, filed on Sep. 26, 2001.

(51) Int. Cl.[7] ............................................. A61K 31/40
(52) U.S. Cl. .................................... 514/419; 548/492
(58) Field of Search ........................... 548/492; 514/419

(56) References Cited

U.S. PATENT DOCUMENTS

| 4,069,343 A | 1/1978 | Sellstedt et al. ............ 424/319 |
| 4,554,290 A | 11/1985 | Boger et al. ................ 514/487 |
| 4,766,121 A | 8/1988 | Ellis et al. .................. 514/247 |
| 4,826,876 A | 5/1989 | Ellis et al. .................. 514/535 |
| 4,910,305 A | 3/1990 | Ellis et al. .................. 544/239 |
| 5,061,798 A | 10/1991 | Emmett et al. ............. 544/239 |
| 5,232,947 A | 8/1993 | Sato et al. .................. 514/549 |
| 5,284,971 A | 2/1994 | Walker et al. .............. 562/429 |
| 5,401,772 A | 3/1995 | Yokoyama et al. ......... 514/539 |
| 5,569,674 A | 10/1996 | Yokoyama, deceased et al. ........................ 514/539 |
| 5,654,468 A | 8/1997 | Yokoyama, deceased et al. ........................ 560/43 |
| 2003/0078288 A1 * | 4/2003 | Haning et al. .............. 514/415 |

FOREIGN PATENT DOCUMENTS

| EP | 0580550 | 10/1997 | ......... C07C/233/56 |
| EP | 1033364 | 9/2000 | ......... C07C/255/50 |
| EP | 1088191 | 9/2000 | ......... C07C/235/74 |
| EP | 1/148054 | 10/2001 | |
| WO | WO 0007972 | 2/2000 | ......... C07C/59/135 |
| WO | WO 0039077 | 7/2000 | ......... C07C/311/00 |
| WO | WO 0058279 | 10/2000 | ......... C07C/311/29 |
| WO | WO 0072810 | 12/2000 | ............ A61K/7/06 |
| WO | WO 0072811 | 12/2000 | ............ A61K/7/06 |
| WO | WO 0072812 | 12/2000 | ............ A61K/7/06 |
| WO | WO 0072813 | 12/2000 | ............ A61K/7/06 |
| WO | WO 0072920 | 12/2000 | ............ A61P/17/14 |
| WO | WO 0051971 | 4/2001 | ......... C07D/253/06 |
| WO | WO 01/70687 | 9/2001 | |

OTHER PUBLICATIONS

Mirziashvili et al., 1991, "synthesis of 5–(p–chlorophenyl)sulfonylindoles", CAS:1991:471307.*

N. Yokoyama, et al., *Synthesis and Structure—Activity Relationships of Oxamic Acid and Acetic Acid Derivatives Related to L–Thyronine*, J. Med. Chem. (1995), 38, 695–707.

Z. F. Stephan, et al., *Demonstration of potent lipid–lowering activity by a thyromimetic agent devoid of cardiovascular and thermogenic effects*, Atheroscierosis, (1996), 126, 53–63.

D. M. T. Chan, et al., *New N–and O–Arylations with Pheyiboronic Acids and Cupric Acetate*, Tetrahedron Letters, (1998), 39, 2933–2936.

A. H. Taylor, et al., *Beneficial Effects of a Novel Thyromimetic on Lipoprotein Metabolism*, Molecular Phamacology, (1997), 52, 542–547.

J. L. Stanton, et al., *Synthesis and Biological Activity of Phenoxyphenyl Oxamic Acid Derivatives Related to L–thyronine*, Bioorganic & Medicinal Chemistry Letters, (2000), 10, 1661–1663.

A. H. Underwood, et al., *A thyromimetic that decreases plasma cholesterol levels without increasing cardiac activity*, Nature, (1986), 324, pp. 425–429.

R. E. Steele, et al., *CGS 26214, the tyroxine connection revisited*, Atheroscierosis X, (1995), 106: 321–324.;.

United States non–provisional patent application No. 09/671,668, filed Sep. 27, 2000 (our reference: PC10219A) (equivalent to EP 1088191).

United States non–provisional patent application No. 09/767771, filed Jan. 23, 2001 (our reference: PC10655A) (claims priority of provisional patent application Ser. No. 60/177,987, filed Jan. 25, 2000).

* cited by examiner

Primary Examiner—Joseph K. McKane
Assistant Examiner—Robert Shiao
(74) Attorney, Agent, or Firm—J. Michael Dixon

(57) ABSTRACT

A compound of the formula

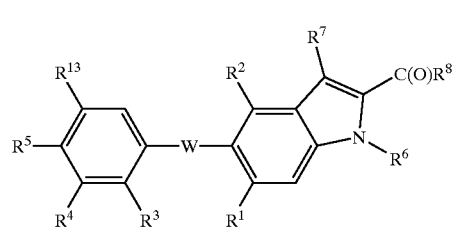

I wherein W, $R^1$, $R^2$, $R^3$, $R^4$, $R^5$, $R^6$, $R^7$, $R^8$ and $R^{13}$ are as defined herein, useful in the treatment of obesity, overweight condition, hyperlipidemia, glaucoma, cardiac arrhythmias, skin disorders, thyroid disease, hypothyroidism, thyroid cancer and related disorders and diseases such as diabetes mellitus, atherosclerosis, hypertension, coronary heart disease, congestive heart failure, hypercholesteremia, depression, osteoporosis and hair loss.

23 Claims, No Drawings

INDOLE CARBOXYLIC ACIDS AS THYROID RECEPTOR LIGANDS

CROSS-REFERENCE TO RELATED APPLICATION

This non-provisional application claims the benefit of U.S. provisional application No. 60/325,385, filed Sep. 26, 2001.

BACKGROUND OF THE INVENTION

The present invention relates to novel thyroid receptor ligands and, more preferably, relates to indole carboxylic acids, and derivatives thereof, which are useful in the treatment of obesity, overweight condition, hyperlipidemia, glaucoma, cardiac arrhythmias, skin disorders, thyroid disease, hypothyroidism, thyroid cancer and related disorders and diseases such as diabetes mellitus, atherosclerosis, hypertension, coronary heart disease, congestive heart failure, hypercholesteremia, depression, osteoporosis and hair loss. The present invention also provides methods, pharmaceutical compositions and kits for treating such diseases and disorders.

Thyroid hormones are important in normal development and in maintaining metabolic homeostasis. For example, thyroid hormones stimulate the metabolism of cholesterol to bile acids and enhance the lipolytic responses of fat cells to other hormones.

Thyroid hormones also affect cardiac function both directly and indirectly, e.g., by increasing the metabolic rate. For example, tachycardia, increased stroke volume, increased cardiac index, cardiac hypertrophy, decreased peripheral vascular resistance and increased pulse pressure are observed in patients with hyperthyroidism.

Disorders of the thyroid gland are generally treated by administering either naturally occurring thyroid hormones or analogues that mimic the effects of thyroid hormones. Such analogues are called thyromimetics or thyroid receptor ligands.

Two naturally occurring thyroid hormones, 3,5,3',5'-tetraiodo-L-thyronine (also referred to as "$T_4$" or thyroxine) and 3,5,3'-triiodo-L-thyronine (also referred to as "$T_3$"), are shown below:

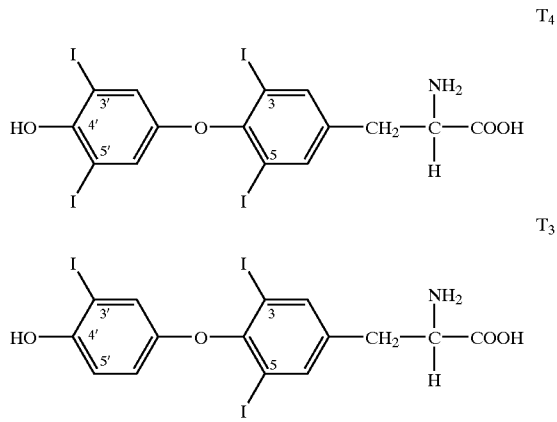

$T_3$ is more biologically active than $T_4$, and differs from $T_4$ by the absence of the 5' iodine. $T_3$ may be produced directly in the thyroid gland, or in peripheral tissues, by the removal of the 5' iodine of $T_4$ by deiodinase enzymes. Thyroid receptor ligands can be designed to be structurally similar to $T_3$. In addition, naturally occurring metabolites of $T_3$ are known.

As discussed above, thyroid hormones affect cardiac functioning, for example, by causing an increase in heart rate, and accordingly, an increase in oxygen consumption. While the increase in oxygen consumption can result in certain desired metabolic effects, nonetheless, it does place an extra burden on the heart, which in some situations, may give rise to damaging side effects. Therefore, as described in A. H. Underwood et al., *Nature*, 324: 425–429 (1986), efforts have been made to synthesize thyroid hormone analogs that function to lower lipids and serum cholesterol, without generating the adverse cardiac effects referred to above.

U.S. Pat. Nos. 4,766,121; 4,826,876; 4,910,305; and 5,061,798 disclose thyroid hormone mimetics, namely, 3,5-dibromo-3'-[6-oxo-3(1H)-pyridazinylmethyl]-thyronines.

U.S. Pat. No. 5,284,971 discloses thyromimetic cholesterol lowering agents, namely, 4-(3-cyclohexyl-4-hydroxy or -methoxy phenylsulfonyl)-3,5 dibromo-phenylacetic acid compounds.

U.S. Pat. Nos. 5,401,772 (also published European Patent Application 0 580 550); U.S. Pat. Nos. 5,654,468 and 5,569,674 disclose certain lipid lowering agents, namely, heteroacetic acid derivatives, more specifically oxamic acid derivatives, which compete with radiolabeled $T_3$ in binding assays using rat liver nuclei and plasma membrane preparations.

Certain oxamic acids and derivatives thereof are known in the art, e.g., U.S. Pat. No. 4,069,343 describes the use of certain oxamic acids to prevent immediate type hypersensitivity reactions; U.S. Pat. No. 4,554,290 describes the use of certain oxamic acids to control pests on animals and plants; and U.S. Pat. No. 5,232,947 describes the use of certain oxamic acids to improve damaged cerebral functions of the brain.

In addition, certain oxamic acid derivatives of thyroid hormones are known in the art. For example, N. Yokoyama et al. in an article published in the *Journal of Medicinal Chemistry*, 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (*Atherosclerosis* X) 106: 321–324 (1995) and Z. F. Stephan et al. in an article published in *Atherosclerosis*, 126: 53–63 (1996), describe a certain oxamic acid derivative useful as a lipid-lowering thyromimetic agent that has reduced adverse cardiac activities.

Commonly assigned International Patent Application Publication No. WO 00/51971, published Sep. 8, 2000, and commonly assigned European Patent Application EP 1 033 364, published Sep. 6, 2000, disclose certain oxamic acids and derivatives thereof as thyroid receptor ligands. Commonly assigned U.S. non-provisional patent application, Ser. No. 09/671668, filed Sep. 27, 1999, discloses certain 6-azauracil derivatives as thyroid receptor ligands. Commonly assigned U.S. provisional patent application, Ser. No. 60/177987, filed Jan. 25, 2000, discloses certain tetrazole compounds as thyroid receptor ligands.

D. M. T. Chan et al., *Tetrahedron Letters*, 39: 2933–2936 (1998) discloses new N- and O-arylations with phenylboronic acids and cupric acetate.

International Patent Application Publication No. WO 00/58279, published Oct. 5, 2000, discloses diaryl derivatives and their use as medicaments.

International Patent Application Publication No. WO 00/07972, published Feb. 17, 2000, discloses glucocorticoid and thyroid hormone receptor ligands for the treatment of metabolic disorders.

International Patent Application Publication No. WO 00/39077, published Jul. 6, 2000, discloses novel thyroid receptor ligands.

A. H. Taylor et al., "Beneficial Effects of a Novel Thyromimetic on Lipoprotein Metabolism," *Molecular Pharmacology*, 52:542–547 (1997), discloses beneficial effects of a novel thyromimetic on lipoprotein metabolism.

J. L. Stanton et al., "Synthesis and Biological Activity of Phenoxyphenyl Oxamic Acid Derivatives Related to L-Thyronine," *Bioorganic &Medicinal Chemistry Letters*, 10: 1661–1663 (2000), discloses the synthesis and biological activity of phenoxyphenyl oxamic acid derivatives related to L-thyronine.

International Patent Application Publication No. WO 00/72810, published Dec. 7, 2000, discloses a method of treating hair loss using certain sulfonyl thyromimetic compounds. International Patent Application Publication No. WO 00/72811, published Dec. 7, 2000, discloses methods of treating hair loss using certain compounds described therein. International Patent Application Publication No. WO 00/72812, published Dec. 7, 2000, discloses methods of treating hair loss using certain diphenylether derivatives. International Patent Application Publication No. WO 00/72813, published Dec. 7, 2000, discloses methods of treating hair loss using certain diphenylmethane derivatives. International Patent Application Publication No. WO 00/72920, published Dec. 7, 2000, discloses certain substituted biaryl ether compounds and compositions for treating hair loss. International Patent Application Publication No. WO 00/73292, published Dec. 7, 2000, discloses certain biaryl compounds and compositions for treating hair loss.

Obesity is a major health risk that leads to increased mortality and incidence of Type 2 diabetes mellitus, hypertension and dyslipidemia. In the US, more than 50% of the adult population is overweight, and almost ¼ of the population is considered to be obese (BMI greater than or equal to 30). The incidence of obesity is increasing in the U.S. at a 3% cumulative annual growth rate. While the vast majority of obesity occurs in the US and Europe, the prevalence of obesity is also increasing in Japan. The prevalence of obesity in adults is 10%–25% in most countries of western Europe.

Obesity is a devastating disease. In addition to harming physical health, obesity can wreak havoc on mental health because obesity affects self-esteem, which ultimately can affect a person's ability to interact socially with others. Unfortunately, obesity is not well understood, and societal stereotypes and presumptions regarding obesity only tend to exacerbate the psychological effects of the disease. Because of the impact of obesity on individuals and society, much effort has been expended to find ways to treat obesity, but little success has been achieved in the long-term treatment and/or prevention of obesity. The present invention provides methods of treating obesity by administering to an obese patient or a patient at risk of becoming obese a therapeutically effective amount of a thyromimetic of the present invention.

The thyromimetics of the present invention can also be used to treat diabetes, atherosclerosis, hypertension, coronary heart disease, hypercholesterolemia, hyperlipidemia, thyroid disease, thyroid cancer, hypothyroidism, depression, glaucoma, cardiac arrhythmias, congestive heart failure, and osteoporosis.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes remains less than satisfactory.

The use of insulin currently requires multiple daily doses, usually by self-injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can have side effects that limit their use, or an agent may not be effective with a particular patient. In the case of insulin dependent diabetes mellitus (Type I), insulin is usually the primary course of therapy. Hypoglycemic agents that have fewer side effects or succeed where others fail are needed.

Atherosclerosis, a disease of the arteries, is recognized to be a leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of "fibrous plaques," which consist of accumulated intimal smooth muscle cells laden with lipid and are surrounded by extra-cellular lipid, collagen, elastin and proteoglycans. The cells plus matrix form a fibrous cap that covers a deeper deposit of cell debris and more extra-cellular lipid. The lipid is primarily free and esterified cholesterol. A fibrous plaque forms slowly, and is likely in time to become calcified and necrotic, advancing to a "complicated lesion," which accounts for arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition that occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

Hair loss is a common problem, which occurs, for example, through natural processes or is often chemically promoted through the use of certain therapeutic drugs designed to alleviate conditions such as cancer. Often such hair loss is accompanied by lack of hair regrowth which causes partial or full baldness.

As is well known in the art, hair growth occurs by a cycle of activity which involves alternating periods of growth and rest. This cycle is often divided into three main stages which are known as anagen, catagen and telogen. Anagen is the growth phase of the cycle and may be characterized by penetration of the hair follicle deep into the dermis with rapid proliferation of cells, which are differentiating to form hair. The next phase is catagen, which is a transitional stage marked by the cessation of cell division, and during which the hair follicle regresses through the dermis and hair growth is ceased. The next phase, telogen, is often characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. When hair growth ceases, most of the hair follicles reside in telogen and anagen is not engaged, thus causing the onset of full or partial baldness.

Interestingly, it is known that the thyroid hormone known as thyroxine ("T4") converts to thyronine ("T3") in human skin by deiodinase I, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. Furthermore, T3 and T4 have been the subject of several patent publications relating to treatment of hair loss, including, for example, International Patent Application Publication No. WO 00/72810, published Dec. 7, 2000; International Patent Application Publication No. WO 00/72811, published Dec. 7, 2000; International Patent Application Publication No. WO 00/72812, published Dec. 7, 2000; International Patent Application Publication No. WO 00/72813, published Dec. 7, 2000; International Patent Application Publication No. WO 00/72920, published Dec. 7, 2000; International Patent Application Publication No. WO 00/73292, published Dec. 7, 2000; and references cited therein.

SUMMARY OF THE INVENTION

The present invention relates to a compound of the formula

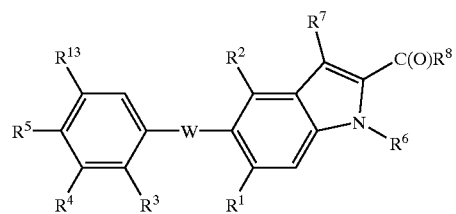

and the pharmaceutically acceptable salts thereof; wherein
W is oxygen, $CH_2$, $CF_2$, $NR^{12}$, $S(O)_m$ wherein m is 0, 1 or 2;
$R^1$, $R^2$, and $R^3$ are each independently selected from the group consisting of hydrogen, halo, cyano, trifluoromethyl, trifluomethoxy and $(C_1-C_6)$alkyl;
$R^4$ is hydrogen, halo, cyano, $(C_1-C_{12})$alkyl, $(C_2-C_{12})$alkenyl, $(C_2-C_{12})$alkynyl, $(C_3-C_{10})$cycloalkyl, $(C_3-C_{10})$cycloalkyl$(C_1-C_6)$alkyl, $(C_6-C_{10})$aryl, $(C_6-C_{10})$aryl$(C_1-C_6)$alkyl, $(C_2-C_9)$heteroaryl, $(C_2-C_9)$heteroaryl$(C_1-C_6)$alkyl, $(C_2-C_9)$heterocycloalkyl, $(C_2-C_9)$heterocycloalkyl$(C_1-C_6)$alkyl, $-OR^9$, $-S(O)_2NR^{10}R^{11}$, $-C(O)NR^{10}R^{11}$, $-C(O)R^{10}$, $-CH(OH)R^{10}$, $-NR^{12}C(O)R^{10}$, $-NR^{12}C(O)NR^{10}R^{11}$, $-NR^{12}S(O)_2R^{10}$ or $-S(O)_nR^{10}$
wherein n is 0, 1 or 2;
$R^5$ is hydroxy, fluoro, $(C_1-C_4)$alkoxy or $-OC(O)R^{10}$;
$R^6$ is hydrogen, $-C(O)CH_3$ or $(C_1-C_6)$alkyl;
$R^7$ is hydrogen or $(C_1-C_6)$alkyl;
$R^8$ is $OR^{12}$ or $NR^9R^{12}$;
$R^9$ for each occurrence is independently hydrogen, $(C_1-C_{12})$alkyl, $(C_3-C_{10})$cycloalkyl, $(C_2-C_9)$heterocycloalkyl, $(C_6-C_{10})$aryl or $(C_2-C_9)$heteroaryl;
$R^{10}$ for each occurrence is independently hydrogen, $(C_1-C_{12})$alkyl, $(C_2-C_{12})$alkenyl, $(C_2-C_{12})$alkynyl, $(C_3-C_{10})$cycloalkyl, $(C_3-C_9)$cycloalkyl$(C_1-C_6)$alkyl, $(C_6-C_{10})$aryl, $(C_2-C_9)$heteroaryl or halo$(C_6-C_{10})$aryl;
$R^{11}$ for each occurrence is independently hydrogen, $(C_1-C_6)$alkyl, $(C_3-C_{10})$ cycloalkyl or $(C_3-C_9)$ cycloalkyl$(C_1-C_6)$alkyl;

or $R^{10}$ and $R^{11}$ may be taken together with the nitrogen to which they are attached to form a 3 to 10 membered heterocyclic group which may contain a second heteroatom selected from oxygen, sulfur or $NR^{14}$ wherein $R^{14}$ is hydrogen or $(C_1-C_6)$alkyl;

$R^{12}$ for each occurrence is independently hydrogen or $(C_1-C_6)$alkyl;

$R^{13}$ is hydrogen, halo or $(C_1-C_6)$alkyl;

or $R^3$ and $R^4$ may be taken together with the carbons to which they are attached to form a compound of the formula

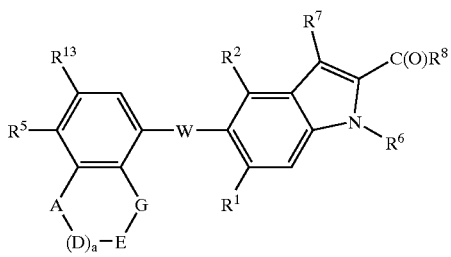

II wherein a is 0, 1, 2 or 3;

A, D, E and G are each independently selected from the group consisting of $CR^{16}R^{17}$, $NR^{18}$, oxygen or sulfur;

$R^{16}$ and $R^{17}$ for each occurrence are each independently selected from hydrogen or $(C_1-C_6)$alkyl; and $R^{18}$ is hydrogen, $(C_1-C_6)$alkyl, $-C(O)R^{10}$ or $-S(O)_2R^{10}$ wherein $R^{10}$ is defined as above.

The term "alkyl" means a straight or branched chain hydrocarbon. Representative examples of alkyl groups include methyl, ethyl, propyl, isopropyl, butyl, isobutyl, tert-butyl, sec-butyl, pentyl, and hexyl. Preferred alkyl groups are $(C_1-C_{12})$alkyl optionally substituted by one to three groups independently selected from halo, hydroxy, oxo, $(C_1-C_6)$alkoxy, $(C_6-C_{10})$aryl, $(C_3-C_{10})$cycloaklyl, $(C_2-C_9)$heterocycloalkyl or $(C_2-C_9)$heteroaryl.

The term "alkoxy" means an alkyl group bonded to an oxygen atom. Representative examples of alkoxy groups include methoxy, ethoxy, tert-butoxy, propoxy, and isobutoxy. Preferred alkoxy groups are $(C_1-C_{12})$alkoxy.

The term "halogen" or "halo" means a radical derived from the elements chlorine, fluorine, bromine, or iodine.

The term "cycloalkyl" means a cyclic hydrocarbon. Examples of cycloalkyl groups include cyclopropyl, cyclobutyl, cyclopentyl, cyclohexyl, and cycloheptyl. Preferred cycloalkyl groups are $(C_3-C_{10})$cyloalkyl. It is also possible for the cycloalkyl group to have one or more double bonds or triple bonds, or a combination of double bonds and triple bonds, but is not aromatic. Examples of cycloalkyl groups having a double or triple bond include cyclopentenyl, cyclohexenyl, cyclohexadienyl, cyclobutadienyl, and the like. It is also noted that the term cycloalkyl includes polycylic compounds such as bicyclic or tricyclic compounds. The cycloalkyl groups may be substituted or unsubsituted with from one to four substitutents.

The term "aryl" means a cyclic, aromatic hydrocarbon. Examples of aryl groups include phenyl, naphthyl and biphenyl. The aryl group may be optionally substituted by halo, cyano, trifluoromethoxy or perfluoro$(C_1-C_4)$alkyl.

The term "heteroatom" includes oxygen, nitrogen, sulfur, and phosphorous.

The term "heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from O, N, and S. The heteroaryl group, including each heteroatom, can be unsubstituted or substituted with from 1 to 4 substituents, as chemically feasible. For example, the heteroatom S may be substituted with one or two oxo groups, which may be shown as =O.

The term "heterocycloalkyl" mean a cycloalkyl group in which one or more of the carbon atoms has been replaced with heteroatoms. If the heterocycloalkyl group contains more than one heteroatom, the heteroatoms may be the same or different. Examples of heterocycloalkyl groups include tetrahydrofuryl, morpholinyl, piperazinyl, piperidyl, and pyrrolidinyl. Preferred heterocycloalkyl groups are five and six membered rings and contain from one to three heteroatoms independently selected from O, N, and S. It is also possible for the heterocycloalkyl group to have one or more double bonds or triple bonds or a combination of double bonds and triple bonds, but it is not aromatic. Examples of heterocycloalkyl groups containing double or triple bonds include dihydrofuran, and the like. A heterocycloalkyl group, including each heteroatom, can be unsubstituted or substituted with from 1 to 4 substituents, as chemically feasible. For example, the heteroatom S may be substituted with one or two oxo groups, which may be shown as =O.

It is also noted that the cyclic ring groups, i.e., aryl, heteroaryl, cycloalkyl, heterocycloalkyl, can comprise more than one ring. For example, the naphthyl group is a fused bicyclic ring system. It is also intended that the present invention include ring groups that have bridging atoms, or ring groups that have a spiro orientation. For example, "spirocycloalkyl" means a cycloalkyl ring having a spiro union (the union formed by a single atom which is the only common member of the rings). In addition, it is understood that, unless specifically noted otherwise, all suitable isomers of the cyclic ring groups are included herein.

Preferred compounds of formula I include those wherein W is oxygen.

Other preferred compounds of formula I include those wherein $R^1$ and $R^2$ are each independently halo, cyano or $(C_1-C_6)$alkyl.

Other preferred compounds of formula I include those wherein $R^3$ is hydrogen or $(C_1-C_4)$alkyl.

Other preferred compounds of formula I include those wherein $R^4$ is halo, $(C_1-C_{12})$alkyl, $-C(O)NR^{10}R^{11}$, $-S(O)_2NR^{10}R^{11}$, $-S(O)_2R^{10}$, $-C(O)R^{10}$, $-CH(OH)R^{10}$ or $-(CH_2)-(C_6-C_{10})$aryl.

Other preferred compounds of formula I include those wherein $R^{10}$ is hydrogen, $(C_1-C_8)$alkyl, $(C_3-C_9)$cycloalkyl, $(C_3-C_9)$cycloaklyl$(C_1-C_6)$alkyl, $(C_6-C_{10})$aryl or halo$(C_6-C_{10})$aryl.

Other preferred compounds of formula I include those wherein $R^{11}$ is hydrogen, $(C_1-C_6)$alkyl, $(C_3-C_9)$cycloalkyl or $(C_3-C_9)$cycloalkyl$(C_1-C_6)$alkyl.

Other preferred compounds of formula I include those wherein $R^5$ is hydroxy.

Other preferred compounds of formula I include those wherein $R^6$ is hydrogen or $(C_1-C_6)$alkyl.

Other preferred compounds of formula I include those wherein $R^7$ is hydrogen or $(C_1-C^4)$alkyl.

Other preferred compounds of formula I include those wherein $R^8$ is $OR^{12}$ wherein $R^{12}$ is hydrogen or $(C_1-C_6)$alkyl.

Other preferred compounds of formula I include those wherein $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is halo; $R^5$ is hydroxy; $R^6$ is hydrogen or $(C_1-C_6)$alkyl; $R^7$ is hydrogen or $(C_1-C_4)$alkyl, $R^8$ is $OR^{12}$ wherein $R^{12}$ is hydrogen or $(C_1-C_6)$alkyl, and $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is $(C_1-C_{12})$alkyl; $R^5$ is hydroxy; $R^6$ is hydrogen or $(C_1-C_6)$alkyl; $R^7$ is hydrogen or $(C_1-C_4)$alkyl; $R^8$ is $OR^{12}$ wherein $R^{12}$ is hydrogen or $(C_1-C_6)$alkyl, and $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is —C(O)N$R^{10}R^{11}$; $R^{10}$ is hydrogen, $(C_1-C_8)$alkyl, $(C_3-C_9)$cycloalkyl, $(C_3-C_9)$cycloalkyl$(C_1-C_6)$alkyl, $(C_6-C_{10})$aryl or halo$(C_6-C_{10})$aryl; $R^{11}$ is hydrogen, $(C_1-C_6)$alkyl, $(C_3-C_9)$cycloalkyl or $(C_3-C_9)$cycloalkyl$(C_1-C_6)$alkyl; $R^5$ is hydroxy; $R^6$ is hydrogen or $(C_1-C_6)$alkyl; $R^7$ is hydrogen or $(C_1-C_4)$alkyl; $R^8$ is $OR^{12}$ wherein $R^{12}$ is hydrogen or $(C_1-C_6)$alkyl, and $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is —S(O)$_2$N$R^{10}R^{11}$; $R^{10}$ is hydrogen, $(C_1-C_8)$alkyl, $(C_3-C_9)$cycloalkyl, $(C_3-C_9)$cycloalkyl$(C_1-C_6)$alkyl, $(C_6-C_{10})$aryl or halo$(C_6-C_{10})$aryl; $R^{11}$ is hydrogen, $(C_1-C_6)$alkyl, $(C_3-C_9)$cycloalkyl or $(C_3-C_9)$cycloalkyl$(C_1-C_6)$alkyl; $R^5$ is hydroxy; $R^6$ is hydrogen or $(C_1-C_6)$alkyl; $R^7$ is hydrogen or $(C_1-C_4)$alkyl; $R^8$ is $OR^{12}$ wherein $R^{12}$ is hydrogen or $(C_1-C_6)$alkyl, and $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is —S(O)$_2R^{10}$; $R^{10}$ is hydrogen, $(C_1-C_8)$alkyl, $(C_3-C_9)$cycloalkyl, $(C_3-C_9)$cycloalkyl$(C_1-C_6)$alkyl, $(C_6-C_{10})$aryl or halo$(C_6-C_{10})$aryl; $R^5$ is hydroxy; $R^6$ is hydrogen or $(C_1-C_6)$alkyl; $R^7$ is hydrogen or $(C_1-C_4)$alkyl; $R^8$ is $OR^{12}$ wherein $R^{12}$ is hydrogen or $(C_1-C_6)$alkyl, and $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is —C(O)$R^{10}$; $R^{10}$ is hydrogen, $(C_1-C_8)$alkyl, $(C_3-C_9)$cycloalkyl, $(C_3-C_9)$cycloalkyl$(C_1-C_6)$alkyl, $(C_6-C_{10})$aryl or halo$(C_6-C_{10})$aryl; $R^5$ is hydroxy; $R^6$ is hydrogen or $(C_1-C_6)$alkyl; $R^7$ is hydrogen or $(C_1-C_4)$alkyl; $R^8$ is $OR^{12}$ wherein $R^{12}$ is hydrogen or $(C_1-C_6)$alkyl, and $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is —CH(OH)$R^{10}$; $R^{10}$ is hydrogen, $(C_1-C_8)$alkyl, $(C_3-C_9)$cycloalkyl, $(C_3-C_9)$cycloalkyl$(C_1-C_6)$alkyl, $(C_6-C_{10})$aryl or halo$(C_6-C_{10})$aryl; $R^5$ is hydroxy; $R^6$ is hydrogen or $(C_1-C_6)$alkyl; $R^7$ is hydrogen or $(C_1-C_4)$alkyl; $R^8$ is $OR^{12}$ wherein $R^{12}$ is hydrogen or $(C_1-C_6)$alkyl, and $R^{13}$ is hydrogen, chloro, fluoro, methyl or isopropyl.

More preferred compounds of formula I include those wherein W is oxygen; $R^1$ and $R^2$ are each independently halo, cyano or $(C_1-C_6)$alkyl; $R^3$ is hydrogen or $(C_1-C_4)$alkyl; $R^4$ is —(CH$_2$)-$(C_6-C_{10})$aryl; $R^5$ is hydroxy; $R^6$ is hydrogen or $(C_1-C_6)$alkyl; $R^7$ is hydrogen or $(C_1-C_4)$alkyl; $R^8$ is $OR^{12}$ wherein $R^{12}$ is hydrogen or $(C_1-C_6)$alkyl, and $R^{13}$ is hydrogen, chloro, fluoro, methyl or isopropyl.

Specifically preferred compounds of formula I are selected from the group consisting of:

5-(4-Hydroxy-3-isopropyl-phenoxy)-4,6-dimethyl-1H-indole-2-carboxylic acid;

4,6-Dichloro-5-(4-hydroxy-3-isopropyl-phenoxy)-1H-indole-2-carboxylic acid;

5-(3-sec-butyl-4-hydroxy-phenoxy)-4,6-dimethyl-1H-indole-2-carboxylic acid;

5-[3-(4-Fluoro-benzyl)-4-hydroxy-phenoxy]-4,6-dimethyl-1H-indole-2-carboxylic acid;

5-{3-[(4-Fluoro-phenyl)-hydroxy-methyl]-4-hydroxy-phenoxy}-4,6-dimethyl-1H-ondole-2-carboxylic acid;

5-[3-(2-Cyclopentyl-1-hydroxy-ethyl)-4-hydroxy-phenoxyl]-4,6-dimethyl-1H-indole-2-carboxylic acid;

5-[3-(4-Fluoro-benzoyl)-4-hydroxy-phenoxyl]-4,6-dimethyl-1H-indole-2-carboxylic acid;

5-[3-(Cyclobutyl-methyl-carbamoyl)-4-hydroxy-phenoxyl]-4,6-dimethyl-1H-indole-2-carboxylic acid;

5-(3-Cyclobutylmethanesulfonyl-4-hydroxy-phenoxy)-4,6-dimethyl-1H-indole-2-carboxylic acid;

4,6-Dichloro-5-(3-cyclobutylmethanesulfonyl-4-hydroxy-phenoxy)-1H-indole-2-carboxylic acid;

4,6-Dichloro-5-(4-hydroxy-3-isopropyl-phenoxy)-1-methyl-1H-indole-2-carboxylic acid;

4,6-Dichloro-5-(4-hydroxy-3-isopropyl-phenoxy)-3-methyl-1H-indole-2-carboxylic acid;

5-[3-(4-Fluoro-benzenesulfonyl)-4-hydroxy-phenoxy]-4,6-dimethyl-1H-indole-2-carboxylic acid;

5-[3-(4-Fluoro-benzenesulfonyl)-4-hydroxy-phenoxy]-3,4,6-trimethyl-1H-indole-2-carboxylic acid;

4,6-Dichloro-5-(3-cyclobutylsulfamoyl-4-hydroxy-phenoxy)-1H-indole-2-carboxylic acid;

4-Chloro-50(3-cyclopropylsulfamoyl-4-hydroxy-phenoxy)-5-methyl-1H-indole-2-carboxylic acid;

4,6-Dichloro-5-[4-hydroxy-3-(1-isopropyl-2-methyl-propylcarbamoyl)-phenoxy]-1H-indole-2-carboxylic acid;

5-[3-(4-Fluoro-benzenesulfonyl)-4-hydroxy-phenoxy]-1,4,6-trimethyl-1H-indole-2-carboxylic acid;

5-[3-[(4-Fluoro-phenyl)-hydroxy-methyl]-4-hydroxy-phenoxy)-3,4,6-trimethyl-1H-indole-2-carboxylic acid;

5-[3-(4-Fluoro-benzyl)-4-hydroxy-phenoxy]-3,4,6-trimethyl-1H-indole-2-carboxylic acid;

5-(3-Cyclopentylmethanesulfonyl-4-hydroxy-phenoxy)-4,6-dimethyl-1H-indole-2-carboxylic acid;

4,6-Dichloro-5-(3-cyclopropylsulfamoyl-4-hydroxy-phenoxy)-1H-indole-2-carboxylic acid;

5-(3-Cyclohexylmethanesulfonyl-4-hydroxy-phenoxy)-4,6-dimethyl-1H-indole-2-carboxylic acid;

5-(3-Cyclopropylsulfamoyl-4-hydroxy-phenoxy)-4,6-dimethyl-1H-indole-2-carboxylic acid;

5-(4-Hydroxy-3-isopropyl-phenoxy)-3,4,6-trimethyl-1H-indole-2-carboxylic acid;

5-(4-Hydroxy-3-isopropyl-phenoxy)-1,4,6-trimethyl-1H-indole-2-carboxylic acid;

4,6-Dichloro-5-[3-(4-fluoro-benzenesulfonyl)-4-hydroxy-phenoxy]-1H-indole-2-carboxylic acid;

4,6-Dichloro-5-[3-(4-fluoro-benzenesulfonyl-4-hydroxy-phenoxy]-3-methyl-1H-indole-2-carboxylic acid;

5-(3-Cyclobutylsulfamoyl-4-hydroxy-phenoxy)-4,6-dimethyl-1H-indole-2-carboxylic acid;

5-[4-Hydroxy-3-(1-isopropyl-2-methyl-propylcarbamoyl)-phenoxy]-4,6-dimethyl-1H-indole-2-carboxylic acid;

4,6-Dichloro-5-{3-[(4-fluoro-phenyl)-hydroxy-methyl]-4-hydroxy-phenoxy)-1H-indole-2-carboxylic acid;

5-(4-Hydroxy-2,3-dimethyl-phenoxy)-4,6-dimethyl-1H-indole-2-carboxylic acid;

4,6-Dichloro-5-(4-hydroxy-2,3-dimethyl-phenoxy)-1H-indole-2-carboxylic acid;

5-(7-Hydroxy-indan-4-yloxy)-4,6-dimethyl-1H-indole-2-carboxylic acid;

4,6-Dichloro-5-(7-hydroxy-indan-4-yloxy)-1H-indole-2-carboxylic acid;

4,6-Dichloro-5-(4-hydroxy-5,6,7,8-tetrahydro-naphthalen-1-yloxy)-1H-indole-2-carboxylic acid; and 5-(4-Hydroxy-5,6,7,8-tetrahydro-naphthalen-1-yloxy)-4,6-dimethyl-1H-indole-2-carboxylic acid.

In addition, the present invention provides methods of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, in a mammal which comprises administering to said mammal a therapeutically effective amount of a compound of Formula I, an isomer thereof, a prodrug of said compound or isomer, or a pharmaceutically acceptable salt of said compound, isomer or prodrug. More preferably, the present invention provides such methods wherein the condition is obesity. More preferably, the present invention provides such methods wherein the condition is atherosclerosis (or hypercholesteremia).

In addition, the present invention provides methods of inducing weight loss in a mammal which comprises administering to said mammal a therapeutically effective amount of a compound of Formula I, an isomer thereof, a prodrug of said compound or isomer, or a pharmaceutically acceptable salt of said compound, isomer or prodrug.

The present invention also provides methods of increasing energy expenditure in a mammal which comprises administering to said mammal a therapeutically effective amount of a compound of Formula I, an isomer thereof, a prodrug of said compound or isomer, or a pharmaceutically acceptable salt of said compound, isomer or prodrug.

In addition, the present invention provides methods of treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, comprising:

administering to a patient having or at risk of having a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, a therapeutically effective amount of 1) a compound of Formula I, an isomer thereof, a prodrug of said compound or isomer, or a pharmaceutically acceptable salt of said compound, isomer or prodrug, as defined in claim 1; and 2) an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss. More preferably, the present invention provides such methods wherein the condition is obesity. More preferably, the present invention provides such methods wherein the additional compound is a lipase inhibitor. Most particularly, the present invention provides such methods wherein the lipase inhibitor is selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. Also, more preferably, the present invention provides such methods wherein the additional compound is an anorectic agent. Most particularly, the present invention provides such methods wherein the anorectic agent is selected from the group consisting of phentermine, sibutramine, fenfluramine, dexfenfluramine and bromocriptine.

In another aspect, the present invention provides pharmaceutical compositions comprising a compound of Formula I, an isomer thereof, a prodrug of said compound or isomer, or a pharmaceutically acceptable salt of said compound, isomer or prodrug.

In another aspect, the present invention provides kits for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss, the kit comprising:
  a) a first pharmaceutical composition comprising a compound of Formula I, an isomer thereof, a prodrug of said compound or isomer, or a pharmaceutically acceptable salt of said compound, isomer or prodrug;
  b) a second pharmaceutical composition comprising an additional compound useful for treating a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss; and
  c) a container.

In another aspect, the present invention provides pharmaceutical compositions comprising a compound of Formula I, an isomer thereof, a prodrug of said compound or isomer, or a pharmaceutically acceptable salt of said compound, isomer or prodrug; and an additional compound useful to treat a condition selected from the group consisting of obesity, overweight condition, hyperlipidemia, glaucoma, cardiac arrhythmias, skin disorders, thyroid disease, hypothyroidism, thyroid cancer, diabetes, atherosclerosis, hypertension, coronary heart disease, congestive heart failure, hypercholesteremia, depression, osteoporosis and hair loss. More preferably, the present invention provides such compositions wherein the condition is obesity. More preferably, the present invention provides such compositions wherein the additional compound is a lipase inhibitor. Most particularly, the present invention provides such compositions wherein the lipase inhibitor is selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. In addition, more preferably, the present invention provides such compositions wherein the additional compound is an anorectic agent. Most particularly, the present invention provides such compositions wherein the anorectic agent is selected from the group consisting of phentermine, sibutramine, fenfluramine, dexfenfluramine and bromocriptine.

Also provided are methods of treating diabetes, the methods comprising the steps of administering to patients having or at risk of having diabetes, a therapeutically effective amount of a compound of Formula I, isomers thereof, prodrugs of said compounds or isomers, or pharmaceutically acceptable salts of said compounds, isomers or prodrugs.

In a preferred embodiment of the method of treating diabetes, the diabetes is Type I diabetes.

In another preferred embodiment of the method of treating diabetes, the diabetes is Type II diabetes.

Also provided are methods of treating atherosclerosis, the methods comprising administering to patients having or at risk of having atherosclerosis, a therapeutically effective amount of a compound of Formula I, isomers thereof, prodrugs of said compounds or isomers, or pharmaceutically acceptable salts of said compounds, isomers or prodrugs.

Also provided are methods of treating hypertension, the methods comprising administering to patients having or at risk of having hypertension, a therapeutically effective amount of a compound of Formula I, isomers thereof, prodrugs of said compounds or isomers, or pharmaceutically acceptable salts of said compounds, isomers or prodrugs.

Also provided are methods of treating coronary heart disease, the methods comprising administering to patients having or at risk of having coronary heart disease, a therapeutically effective amount of a compound of Formula I, isomers thereof, prodrugs of said compounds or isomers, or pharmaceutically acceptable salts of said compounds, isomers or prodrugs.

Also provided are methods of treating hypercholesterolemia, the methods comprising administering to patients having or at risk of having hypercholesterolemia, a therapeutically effective amount of a compound of Formula I, isomers thereof, prodrugs of said compounds or isomers, or pharmaceutically acceptable salts of said compounds, isomers or prodrugs.

Also provided are methods of treating hyperlipidemia, the methods comprising administering to patients having or at risk of having hyperlipidemia, a therapeutically effective amount of a compound of Formula I, isomers thereof, prodrugs of said compounds or isomers, or pharmaceutically acceptable salts of said compounds, isomers or prodrugs.

Also provided are methods of treating thyroid disease, the methods comprising administering to patients having or at risk of having thyroid disease, a therapeutically effective amount of a compound of Formula I, isomers thereof, prodrugs of said compounds or isomers, or pharmaceutically acceptable salts of said compounds, isomers or prodrugs.

Also provided are methods of treating hypothyroidism, the methods comprising administering to patients having or at risk of having hypothyroidism, a therapeutically effective amount of a compound of Formula I, isomers thereof, prodrugs of said compounds or isomers, or pharmaceutically acceptable salts of said compounds, isomers or prodrugs.

Also provided are methods of treating depression, the methods comprising administering to patients having or at risk of having depression, a therapeutically effective amount of a compound of Formula I, isomers thereof, prodrugs of said compounds or isomers, or pharmaceutically acceptable salts of said compounds, isomers or prodrugs.

Also provided are methods of treating obesity, the methods comprising administering to obese patients or patients at risk of becoming obese, a therapeutically effective amount of a compound of Formula I, isomers thereof, prodrugs of said compounds or isomers, or pharmaceutically acceptable salts of said compounds, isomers or prodrugs.

Also provided are methods of treating osteoporosis, the methods comprising administering to patients having or at risk of having osteoporosis, a therapeutically effective amount of a compound of Formula I, isomers thereof, prodrugs of said compounds or isomers, or pharmaceutically acceptable salts of said compounds, isomers or prodrugs.

Also provided are methods of treating thyroid cancer, the methods comprising administering to patients having or at risk of having thyroid cancer, a therapeutically effective amount of a compound of Formula I, isomers thereof, prodrugs of said compounds or isomers, or pharmaceutically acceptable salts of said compounds, isomers or prodrugs.

Also provided are methods of treating glaucoma, the methods comprising administering to patients having or at risk of having glaucoma, a therapeutically effective amount of a compound of Formula I, isomers thereof, prodrugs of said compounds or isomers, or pharmaceutically acceptable salts of said compounds, isomers or prodrugs.

Also provided are methods of treating cardiac arrhythmias, the methods comprising administering to patients having or at risk of having cardiac arrhythmias, a therapeutically effective amount of a compound of Formula I, isomers thereof, prodrugs of said compounds or isomers, or pharmaceutically acceptable salts of said compounds, isomers or prodrugs.

Also provided are methods of treating congestive heart failure, the methods comprising administering to patients having or at risk of having congestive heart failure, a therapeutically effective amount of a compound of Formula I, isomers thereof, prodrugs of said compounds or isomers, or pharmaceutically acceptable salts of said compounds, isomers or prodrugs.

Also provided are methods of treating hair loss, the methods comprising administering to patients having or at risk of having hair loss, a therapeutically effective amount of a compound of Formula I, isomers thereof, prodrugs of said compounds or isomers, or pharmaceutically acceptable salts of said compounds, isomers or prodrugs.

DETAILED DESCRIPTION OF THE INVENTION

Scheme 1

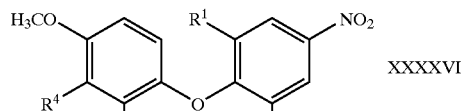
XXXXVI

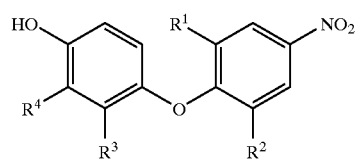
III

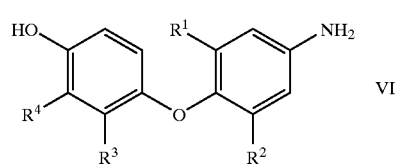
VI

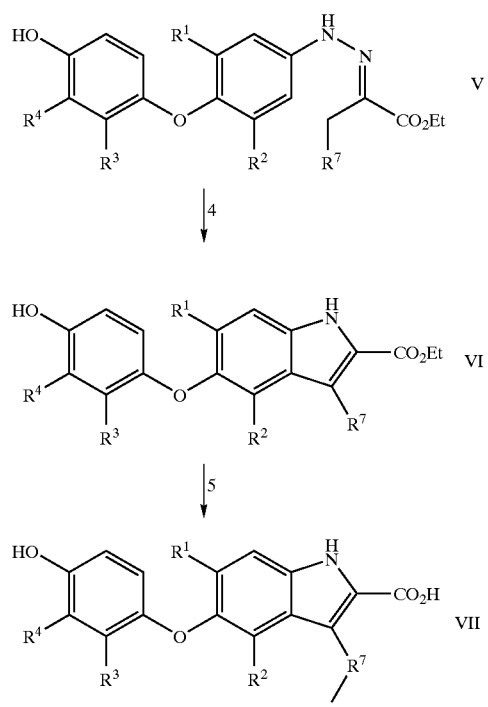

Scheme 2

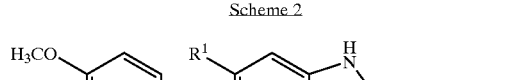
VIII

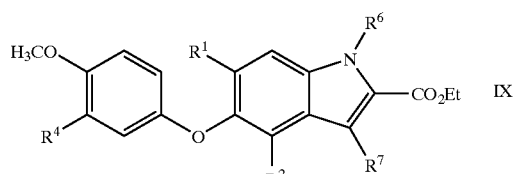
IX

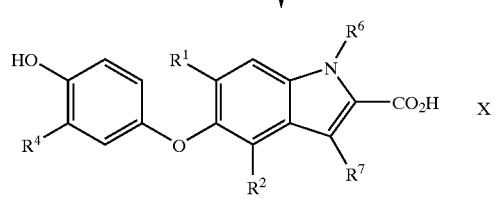
X

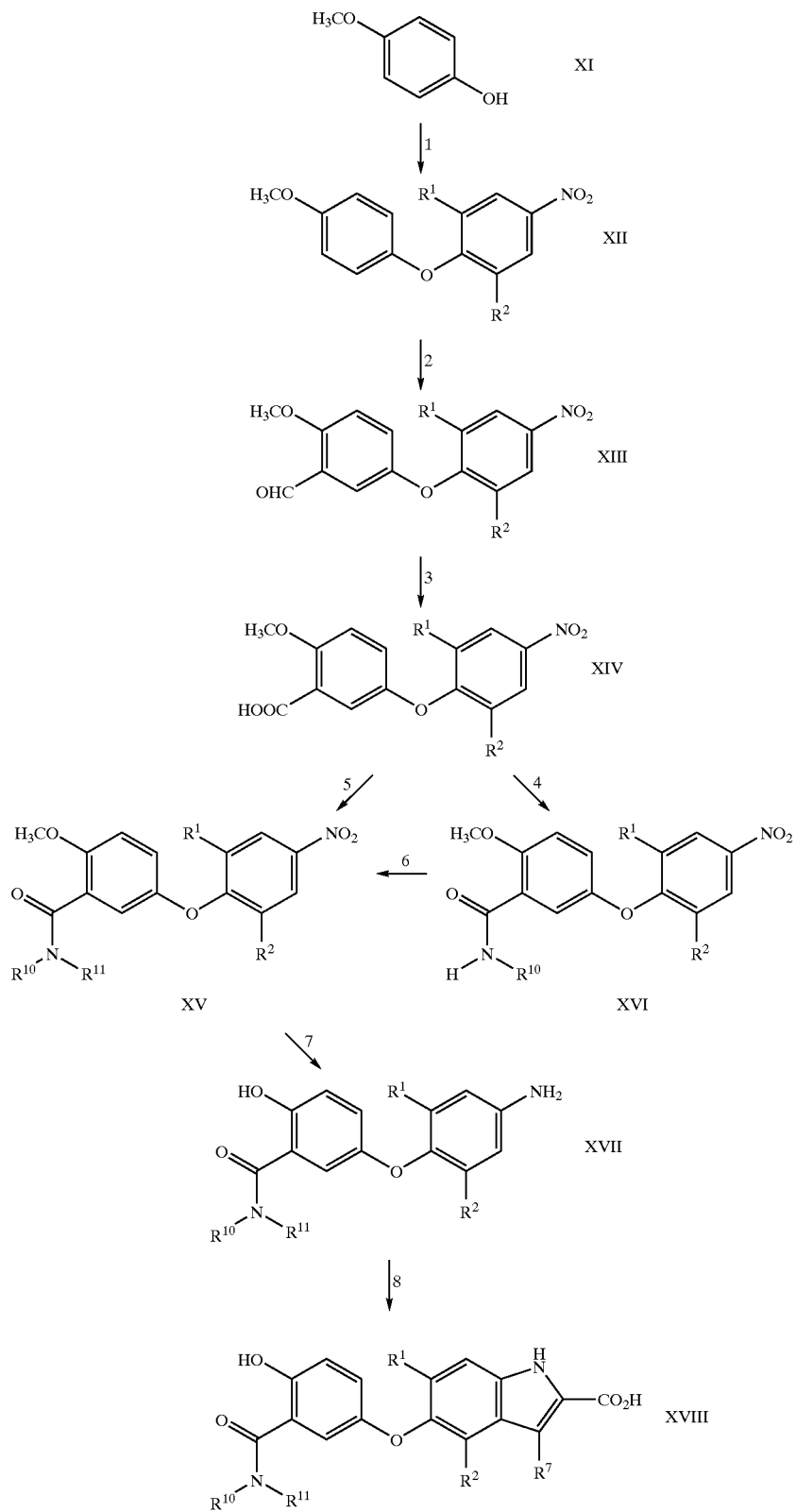

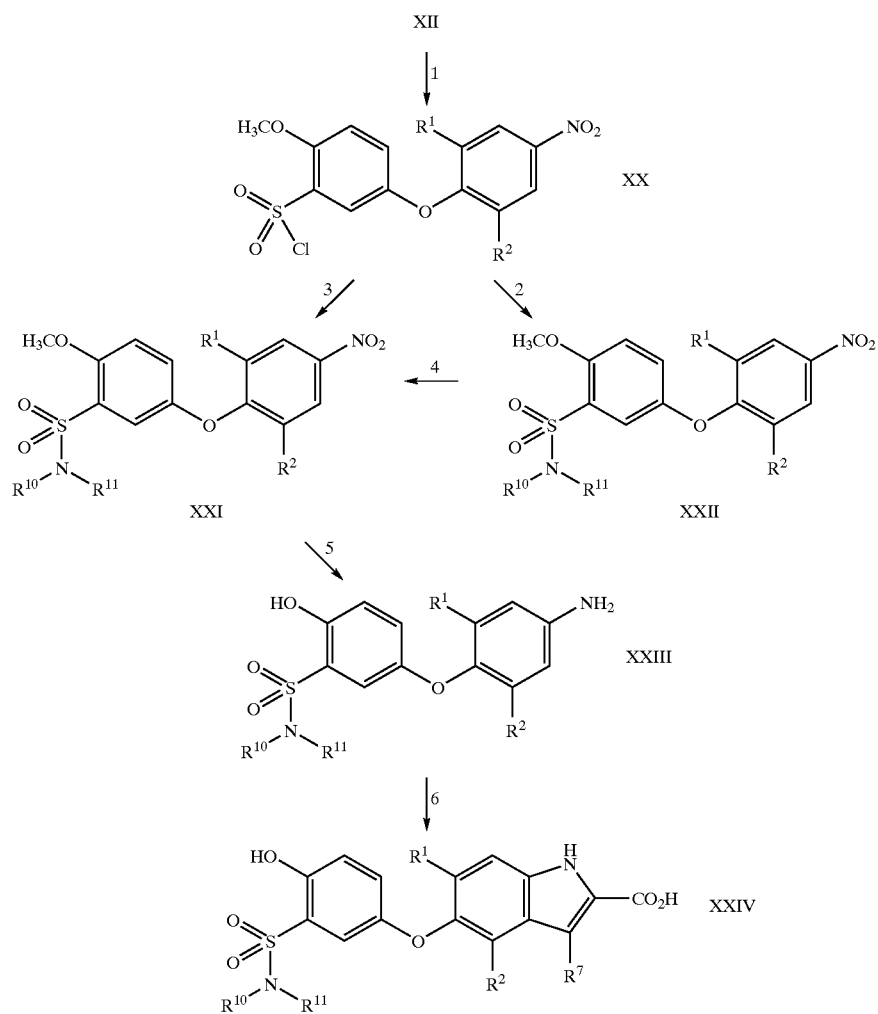
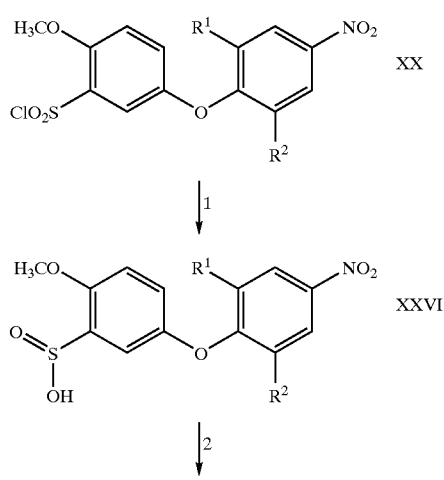
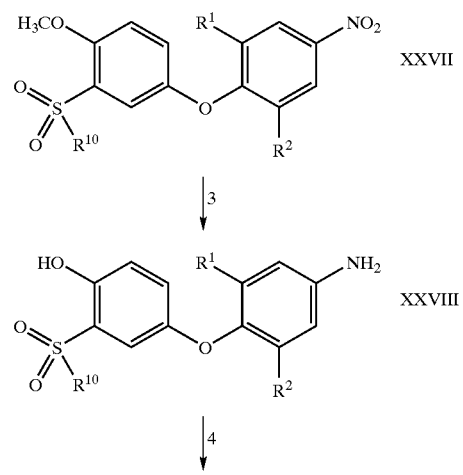

-continued
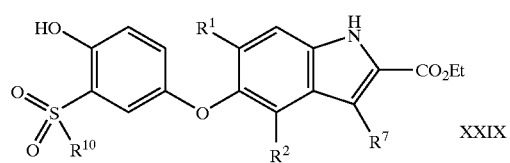
XXIX
↓5
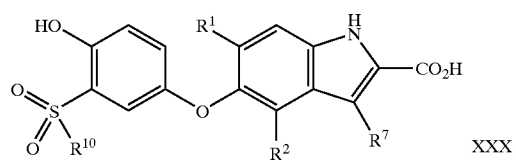
XXX
Scheme 6
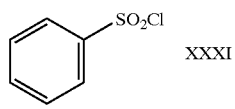
XXXI
↓1
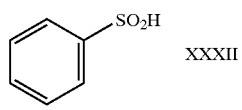
XXXII
↓2
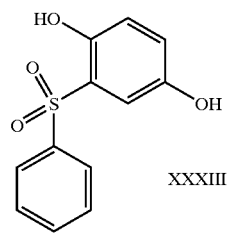
XXXIII
↓3
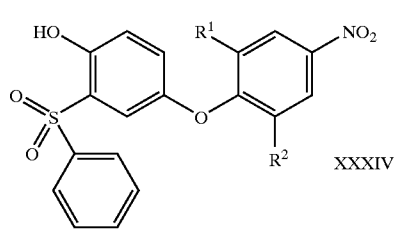
XXXIV
↓4
-continued
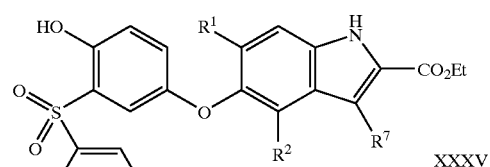
XXXV
↓5
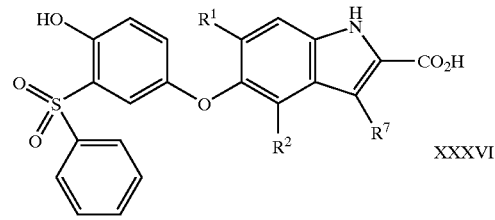
XXXVI
Scheme 7
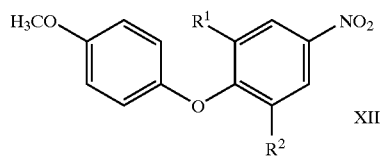
XII
↓1
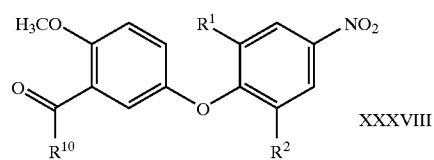
XXXVIII
↓2
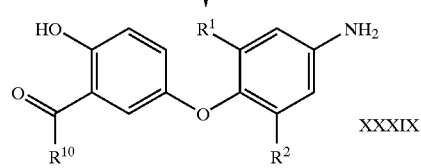
XXXIX
↓3
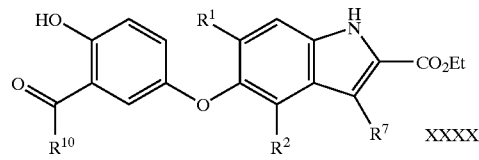
XXXX
↓4

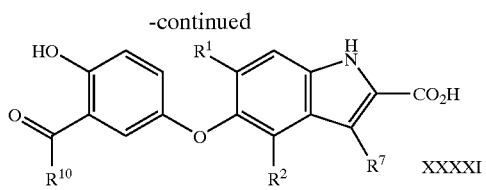

XXXXI

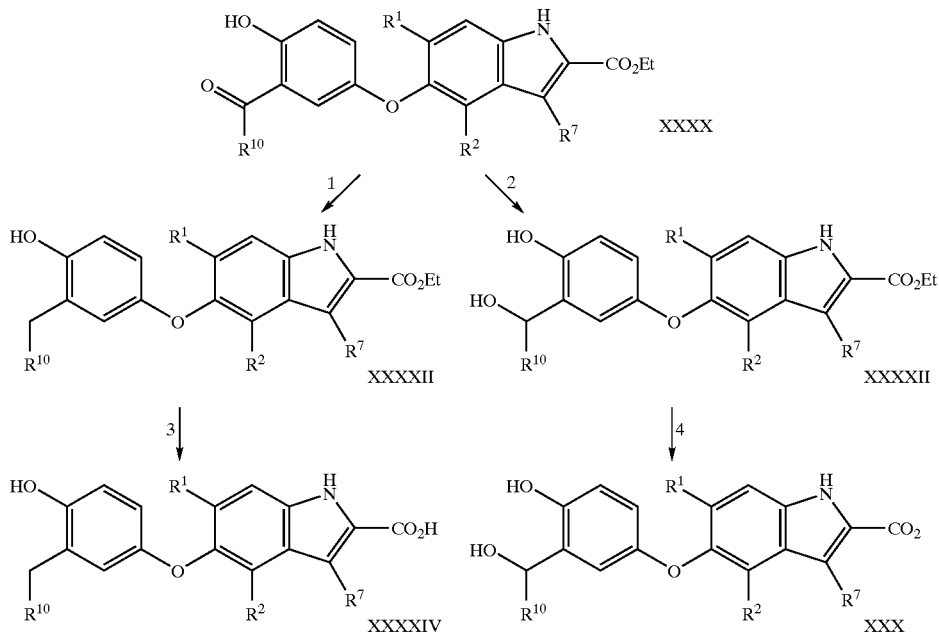

In reaction 4 of Scheme 1, the hydrazone compound of formula V is converted to the corresponding indole ester compound of formula VI by heating V to reflux in the presence of p-toluenesulfonic acid, and an aprotic solvent, such as toluene. The reaction mixture is stirred for a time period between about 1 hour and to about 24 hours, preferably about 2 hours.

In reaction 5 of Scheme 1, the indole ester compound of formula VI is converted to the corresponding indole carboxylic acid compound of formula VII by treating VI with potassium hydroxide or sodium hydroxide in the presence of a solvent mixture, such as methanol and water. The reaction mixture is stirred, at room temperature, for a time period between about 1 hour to about 24 hours, preferably about 2 hours.

The compound of formula II can be prepared according to the procedure described in *J. Med. Chem.*, 38, 697–707 (1995).

In reaction 1 of Scheme 1, the compound of formula XXXXVI is converted to the corresponding compound of formula III by reacting XXXXVI with boron tribromide in a solvent, such as methylene chloride or chloroform. The reaction mixture is stirred, at room temperature, for a time period between about 30 minutes to about 24 hours, preferably about 1 hour.

In reaction 2 of Scheme 1, the nitro compound of formula III is converted to the corresponding aniline compound of formula VI by reducing III with hydrogen in the presence of a catalyst, such as 10% palladium on carbon, and a polar protic solvent, such as methanol or ethanol, or a solvent mixture, such as ethyl acetate and ethanol. The reaction mixture is stirred, at room temperature, under pressure of about 40 psi, for a time period between about 1 hour to about 24 hours.

In reaction 3 of Scheme 1, the aniline compound of formula VI is converted to the corresponding hydrazone compound of formula V by treating VI with sodium nitrate in the presence of hydrochloric acid and reacting the diazonium intermediate so formed with ethyl acetoacetate, in the presence of a polar protic solvent, such as ethanol. The reaction mixture is stirred, at room temperature, for a time period between about 30 minutes to about 24 hours, preferably about 1 hour.

In reaction 1 of Scheme 2, the compound of formula VII is converted to the corresponding compound of formula IX by treating VII with a base, such as sodium hydride, and reacting the intermediate so formed, at a temperature about 0° C., with a $(C_1-C_6)$alkyl halide, such as iodo$(C_1-C_6)$ alkane, in the presence of a solvent, such as dimethylformamide. The reaction mixture is warmed to room temperature and stirred for a time period between about 16 hours to about 48 hours, preferably about 19 hours.

In reaction 2 of Scheme 2, the compound of formula IX is converted to the corresponding compound of formula X by reacting IX with boron tribromide in the presence of a solvent, such as methylene chloride. The intermediate so formed is then treated with a base, such as potassium hydroxide or sodium hydroxide, in the presence an aqueous polar solvent, such as 50% aqueous methanol, to give X.

In reaction 1 of Scheme 3, the 4-methoxy-phenol compound of formula XI is converted to the corresponding diaryl ether compound of formula XII by treating XI with a compound of the formula

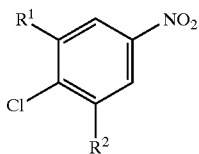

in the presence of potassium carbonate and a solvent, such as methyl sulfoxide or N-methylpyrrolidone. The reaction is stirred at a temperature between about 80° C. to about 140° C., preferably about 125° C., for a time period between about 15 hours to about 48 hours, preferably about 20 hours.

In reaction 2 of Scheme 3, the compound of formula XII is converted to the corresponding aldehyde compound of formula XII by reacting XII with hexamethylenetetramine in the presence of trifluoroacetic acid. The reaction mixture is then stirred at a temperature between about 60° C. to about 80° C., preferably about 75° C., for a time period between about 4 hours to about 24 hours, preferably about 8 hours.

In reaction 3 of Scheme 3, the compound of formula XIII is converted to the corresponding compound of formula XIV by the oxidation of XII with sodium chlorite in the presence of 2-methyl-2-butene, t-butanol and potassium dihydrogenphosphate in the presence of a solvent, such as tetrahydrofuran. The reaction mixture is stirred, at room temperature, for a time period between about 12 hours to about 48 hours, preferably about 16 hours.

In reaction 4 of Scheme 3, the carboxylic acid compound of formula XIV is converted to the corresponding compound of formula XVI by reacting the corresponding acid chloride or mixed anhydride of XIV with a primary amine of the formula, $NH_2R^{10}$, in the presence of a base, such as triethylamine, dimethylaminopyridine or pyridine, a solvent, such as dichloromethane, tetrahydrofuran, ethylene glycol dimethyl ether or 2,2-bis(4-chlorophenyl)-1,1-dichloroethylene. The reaction is stirred, under inert atmosphere, at a temperature between about –10° C. to about 25° C., preferably about 0° C., for a time period of about 30 minutes to about 12 hours, preferably about 2 hours. The carboxylic acid compound of formula XIV can also be converted to the corresponding compound of formula XVI by reacting XIV with a primary amine of the formula, $NH_2R^{10}$, in the presence of N-hydroxysuccinimide, dicyclohexylcarbodiimide and a base, such as triethyamine.

In reaction 5 of Scheme 3, the carboxylic acid compound of formula XIV is converted to the corresponding compound of formula XV by reacting XIV, or the corresponding acid chloride or mixed anhydride of XIV, with a secondary amine of the formula, $HNR^{10}R^{11}$, according to the procedure described above in reaction 4 of Scheme 3.

In reaction 6 of Scheme 3, the amide compound of formula XVI is converted to the corresponding compound of formula XV by alkylating XVI with an alkyl halide of the formula $R^{11}X$, wherein X is halo, in the presence of a base, such as sodium hydride, and a polar aprotic solvent, such as tetrahydrofuran.

In reaction 7 of Scheme 3, the compound of formula XV is converted to the corresponding compound of formula XVII by treating XV with boron tribromide, at room temperature, in the presence of a solvent, such as methylene chloride. The compound so formed is hydrogenated in the presence of a catalyst, such as 10% palladium on carbon, under a pressure of about 40 psi, for a time period between about 3 hours to about 24 hours, preferably about 4 hours.

In reaction 8 of Scheme 3, the compound of formula XVII is converted to the corresponding compound of formula XVIII according to the procedure described above in reactions 3, 4 and 5 of Scheme 1.

In reaction 1 of Scheme 4, the compound of formula XII is converted to the corresponding compound of formula XX by reacting XII with chlorosulfonic acid. The reaction mixture is stirred at a temperature between about –10° C. to about 10° C., preferably about 0° C., for a time period of about 5 minutes, then allowed to warm to room temperature for about an 1 hour.

In reaction 2 of Scheme 4, the sulfonyl chloride compound of formula XX is converted to the corresponding compound of formula XXII according to the procedure described above in reaction 4 of Scheme 3.

In reaction 3 of Scheme 4, the sulfonyl chloride compound of formula XX is converted to the corresponding compound of formula XXI according to the procedure described in reaction 5 of Scheme 3.

In reaction 4 of Scheme 4, the compound of formula XXII is converted to the corresponding compound of formula XXI according to the procedure described above in reaction 6 of Scheme 3.

In reaction 5 of Scheme 4, the compound of formula XXI is converted to the corresponding compound of formula XXIII according to the procedure described above in reaction 7 of Scheme 3.

In reaction 6 of Scheme 4, the compound of formula XXIII is converted to the corresponding indole compound of formula XXIV according to the procedures described above in reactions 3, 4 and 5 of Scheme 1.

In reaction 1 of Scheme 5, the sulfonylchloride compound of formula XX is converted to the corresponding sulfinic acid compound of formula XXVI by reacting XX with sodium sulfite, in the presence of water and a base, such as sodium bicarbonite or sodium hydroxide. The reaction mixture is stirred at a temperature between about 50° C. to about 100° C., preferably about 65° C., for a time period between about 1 hour to about 24 hours, preferably about 6 hours, followed by continued stirring, at room temperature, overnight.

In reaction 2 of Scheme 5, the sulfinic acid compound of formula XXVI is converted to the corresponding alkylsulfone compound of formula XXVII by alkylating XXVI with an alkylhalide of the formula, $R^{10}X$ wherein X is halo, in the presence of a base, such as sodium bicarbonate, sodium hydroxide, sodium hydride, sodium methoxide or potassium t-butoxide.

In reaction 3 of Scheme 5, the compound of formula XXVII is converted to the corresponding compound of formula XXVIII according to the procedure described above in reaction 7 of Scheme 3.

In reaction 4 of Scheme 5, the compound of formula XXVIII is converted to the corresponding indole compound of formula XXIX according to the procedure described above in reactions 3 and 4 of Scheme 1.

In reaction 5 of Scheme 5, the compound of formula XXIX is converted to the corresponding compound of formula XXX according to the procedure described above in reaction 5 of Scheme 1.

In reaction 1 of Scheme 6, the sulfonylchoride compound of formula XXXI is converted to the corresponding sulfinic acid compound of formula XXXII according to the procedure described above in reaction 1 of Scheme 5.

In reaction 2 of Scheme 6, the sulfinic acid compound of formula XXXII is converted to the corresponding dihydroxy benzene compound of formula XXXIII by reacting XXXII with benzoquinone in the presence of a polar protic solvent, such as ethanol, and water. The resulting reaction mixture is stirred, at room temperature, for time period between about 1 hour to about 24 hours, preferably about 4 hours.

In reaction 3 of Scheme 6, the dihydroxy benzene compound of formula XXXIII is converted to the corresponding compound of formula XXXIV by treating XXIII with potassium bis(trimethylsilyl)amide in N-methylpyrrolidinone, in the presence of 18-crown-6, followed by reacting the intermediate so formed with a 4-halonitrobenzene. The reaction is stirred, at room temperature, under an inert atmosphere for a time period between about 1 hour to about 24 hours, preferably about 6 hours.

In reaction 4 of Scheme 6, the nitro compound of formula XXXIV is converted to the corresponding indole ester compound of formula XXXV according to the procedures describe above in reactions 2, 3 and 4 of Scheme 1.

In reaction 5 of Scheme 6, the indole ester compound of formula XXXV is converted to the corresponding indole carboxylic acid compound of formula XXXVI according to the procedure described above in reaction 5 of Scheme 1.

In reaction 1 of Scheme 7, the compound of formula XII is converted to the corresponding ketone compound of formula XXXVIII by reacting XII with an acid chloride compound of the formula, $R^{10}C(O)Cl$, in the presence of titanium tetrachloride and a solvent, such as dichloromethane.

In reaction 2 of Scheme 7, the compound of formula XXXVIII is converted to the corresponding compound of formula XXXIX according to the procedures described above in reactions 1 and 2 of Scheme 1.

In reaction 3 of Scheme 7, the aniline compound of formula XXXIX is converted to the corresponding indole compound of formula XXXX according to the procedures described above in reactions 3, 4 and 5 of Scheme 1.

In reaction 4 of Scheme 7, the compound of formula XXXX is converted to the corresponding compound of formula XXXXI according to the procedure described above in reaction 5 of Scheme 1.

In reaction 1 of Scheme 8, the compound of formula XXXX is converted to the corresponding compound of formula XXXXII by reducing XXXX with triethylsilane and trifluoroacetic acid in a solvent, such as dichloromethane. The reaction is stirred, at room temperature, for a time period between about 12 hours to about 24 hours, preferably about 18 hours.

In reaction 2 of Scheme 8, the compound of formula XXXX is converted to the corresponding hydroxy compound of formula XXXXIII by treating XXXX with sodium borohydride in the presence of a polar protic solvent, such as ethanol. The reaction is stirred, at room temperature, for a time period between about 30 minutes to about 24 hours, preferably about 4 hours.

In reaction 3 of Scheme 8, the compound of formula XXXXII is converted to the corresponding compound of formula XXXXIV by treating XXXXII with a base, such as sodium hydroxide or potassium hydroxide, in the presence of water and a polar protic solvent, such as methanol. The reaction mixture is stirred, at room temperature, for a time period between about 12 hours to about 25 hours, preferably about 20 hours.

In reaction 4 of Scheme 8, the compound of formula XXXXIII is converted to the corresponding compound of formula XXXXV according to the procedure described above in reaction 3 of Scheme 8.

When the above described reactions refer to other procedures for other Schemes, such procedures are of course analogous procedures. All variables are as defined for compounds of formula I unless otherwise specified.

The present invention has an aspect that relates to the treatment of the disease/conditions described herein with a combination of active ingredients. In combination therapy treatment, both the compounds of this invention and the other drug therapies are administered to mammals (e.g., humans, male or female) by conventional formulations and methods, as described above. As recognized by those skilled in the art, the therapeutically effective amounts of the compounds of this invention and the other drug therapies to be administered to a patient in combination therapy treatment will depend upon a number of factors, including, without limitation, the biological activity desired, the condition of the patient, and tolerance for the drug. Dosages and modes of administration of the other drug therapies useful in the present invention are known in the art, for example, as set forth in the patents, patent applications and publications described below, which are hereby incorporated by reference herein in their entirety.

For instance, the characteristics of patients at risk of having atherosclerosis are well known to those in the art and include patients who have a family history of cardiovascular disease, including hypertension and atherosclerosis, obese patients, patients who exercise infrequently, patients with hypercholesterolemia, hyperlipidemia and/or hypertriglyceridemia, patients having high levels of LDL or Lp(a), patients having low levels of HDL, and the like.

In one aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the diabetic complications, such as neuropathy, nephropathy, retinopathy or cataracts.

The preferred type of diabetes to be treated by the compounds of the present invention is non-insulin dependent diabetes mellitus, also known as Type II diabetes or NIDDM.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention along with other agents that can be used to treat diabetes.

Representative agents that can be used to treat diabetes in combination with a compound of the present invention include insulin and insulin analogs (e.g., LysPro insulin); GLP-1 (7-37) (insulinotropin) and GLP-1 (7-36)-$NH_2$; sulfonylureas and analogs: chlorpropamide, glibenclamide, tolbutamide, tolazamide, acetohexamide, Glypizide®, glimepiride, repaglinide, meglitinide; biguanides: metformin, phenformin, buformin; 2-antagonists and imidazolines: midaglizole, isaglidole, deriglidole, idazoxan, efaroxan, fluparoxan; other insulin secretagogues: linoglitide, A-4166; glitazones: ciglitazone, Actos® (pioglitazone), englitazone, troglitazone, darglitazone, Avandia® (BRL49653); fatty acid oxidation inhibitors: clomoxir, etomoxir; -glucosidase inhibitors: acarbose, miglitol, emiglitate, voglibose, MDL-25,637, camiglibose, MDL-73,945; -agonists: BRL 35135, BRL 37344, RO 16-8714, ICI D7114, CL 316,243; phosphodiesterase inhibitors: L-386,398; lipid-lowering agents: benfluorex; antiobesity agents: fenfluramine; vanadate and vanadium complexes (e.g., Naglivan®) and peroxovanadium complexes; amylin antagonists; glucagon antagonists; gluconeogenesis inhibitors; somatostatin analogs; antipolytic agents: nicotinic acid, acipimox, WAG 994. Also contemplated to be used in combination with a compound of the present invention are pramlintide (Symlin), AC 2993 and nateglinide. Any agent or combination of agents can be administered as described above.

In addition, the compounds of the present invention can be used in combination with one or more aldose reductase inhibitors, glycogen phosphorylase inhibitors, sorbitol dehydrogenase inhibitors, NHE-1 inhibitors and/or glucocorticoid receptor antagonists. The compounds of the present invention can be used in combination with an aldose reductase inhibitor. Aldose reductase inhibitors constitute a class of compounds that have become widely known for their utility in treating conditions arising from complications of diabetes, such as diabetic neuropathy and nephropathy. Such compounds are well known to those skilled in the art and are readily identified by standard biological tests. For example, the aldose reductase inhibitor zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140, commonly assigned.

Aldose reductase inhibitors have been taught for use in lowering lipid levels in mammals. See, for example, U.S. Pat. No. 4,492,706 to Kallai-sanfacon and EP 0 310 931 A2.

U.S. Pat. No. 5,064,830 discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood. Such diseases include cardiovascular disorders such as thrombosis, arteriosclerosis, myocardial infarction, and angina pectoris. A preferred aldose reductase inhibitor is zopolrestat.

The term aldose reductase inhibitor refers to compounds that inhibit the bioconversion of glucose to sorbitol, which is catalyzed by the enzyme aldose reductase. Any aldose reductase inhibitor may be used in a combination with a compound of the present invention. Aldose reductase inhibition is readily determined by those skilled in the art according to standard assays (J. Malone, *Diabetes*, 29: 861–864 (1980), "Red Cell Sorbitol, An Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose).

Accordingly, additional examples of aldose reductase inhibitors useful in the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl] thioxomethyl]-N-methylglycine (tolrestat, U.S. Pat. No. 4,600,724);
3. 5-[(Z,E)-methylcinnamylidene]-4-oxo-2-thioxo-3-thiazolideneacetic acid (epalrestat, U.S. Pat. Nos. 4,464,382; 4,791,126; and 4,831,045);
4. 3-(4-bromo-2-fluorobenzyl)-7-chloro-3,4-dihydro-2,4-dioxo-1(2H)-quinazolineacetic acid (zenarestat, U.S. Pat. Nos. 4,734,419 and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. Nos. 5,270,342 and 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)2',5'-dione (U.S. Pat. No. 4,438,272);
13. 2,7-di-fluoro-spiro(9H-fluorene-9,4'-imidazolidine)2',5'-dione (U.S. Pat. Nos. 4,436,745 and 4,438,272);
14. 2,7-di-fluoro-5-methoxy-spiro(9H-fluorene-9,4'-imidazolidine)2',5'-dione (U.S. Pat. Nos. 4,436,745 and 4,438,272);
15. 7-fluoro-spiro(5H-indenol[1,2-b]pyridine-5,3'-pyrrolidine)2,5'-dione (U.S. Pat. Nos. 4,436,745 and 4,438,272);
16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);
17. spiro[imidazolidine-4,5'(6H)-quinoline]2,5-dione-3'-chloro-7',8'-dihydro-7'-methyl-(5'-cis)(U.S. Pat. No. 5,066,659);
18. (2S,4S)-6-fluoro-2',5'-dioxospiro(chroman-4,4'-imidazolidine)-2-carboxamide (U.S. Pat. No. 5,447,946); and
19. 2-[(4-bromo-2-fluorophenyl)methyl]-6-fluorospiro [isoquinoline-4(1 H),3'-pyrrolidine]-1,2',3,5'(2H)-tetrone (ARI-509, U.S. Pat. No. 5,037,831).

Other aldose reductase inhibitors include compounds having formula Ia below:

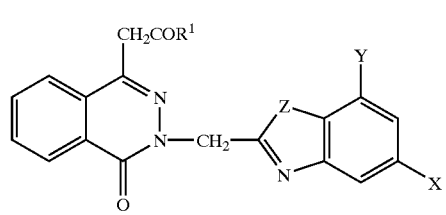

Ia and pharmaceutically acceptable salts and prodrugs thereof, wherein

Z is O or S;

$R^1$ is hydroxy or a group capable of being removed in vivo to produce a compound of formula I wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula Ia:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=$CF_3$; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];
27. 3-(5-chlorobenzoxazol-2-ylmethyl)-3,4-dihydro-4-oxophthalazin-1-ylacetic acid [$R^1$=hydroxy; X=Cl; Y=H];
28. 3-(5,7-dichlorobenzoxazol-2-ylmethyl)-3,4-dihydro-4-oxophthalazin-1-ylacetic acid [$R^1$=hydroxy; X=Y=Cl]; and
29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred, with 29 being especially preferred. Procedures for making the aldose reducatase inhibitors of formula Ia can be found in International Patent Application, Publication No. WO 99/26659.

The compounds of the present invention can also be used in combination with a glucocorticoid receptor modulator, or more preferably, a glucocorticoid receptor antagonist. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NF-. Such interactions result in inhibition of API- and NF-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. Examples of GR antagonists that can be used in combination with a compound of the present invention include compounds disclosed in commonly assigned International Patent Application, Publication No. WO 00/66522, which is hereby incorporated by reference herein.

The compounds of the present invention can also be used in combination with a sorbitol dehydrogenase inhibitor. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

A compound of the present invention can also be used in combination with a sodium-hydrogen exchanger type 1 (NHE-1) inhibitor. Examples of NHE-1 inhibitors include compounds disclosed in International Patent Application, Publication No. WO 99/43663, which is hereby incorporated by reference herein.

A compound of the present invention can also be used in combination with a glycogen phosphorylase inhibitor. Examples of glycogen phosphorylase inhibitors are set forth in commonly assigned U.S. Non-provisional Patent Application No. 09/670,759, filed Sep. 27, 2000; and commonly assigned International Patent Applications, Publication Nos. WO 96/39384 and WO 96/39385, which are hereby incorporated by reference herein.

Any glycogen phosphorylase inhibitor may be used in combination with a compound of the present invention. Glycogen phosphorylase inhibition is readily determined by those skilled in the art according to standard assays (for example, Pesce, et al., *Clinical Chemistry* 23:1711–1717 (1977)). A variety of glycogen phosphorylase inhibitors are described above, however, other glycogen phosphorylase inhibitors will be known to those skilled in the art (e.g., International Patent Application, Publication No. WO 95/24391-A and those disclosed in U.S. Pat. No. 5,952,363). The following documents also disclose glycogen phosphorylase inhibitors that can be used in the present invention: U.S. Pat. No. 5,998,463; Oikanomakos et al., *Protein Science*, 1999 8(10) 1930–1945, which in particular discloses the compound 3-isopropyl-4-(2-chlorophenyl)-1,4-dihydro-1-ethyl-2-methylpyridine; International Patent Applications, Publication Nos. WO 95/24391, WO 97/09040, WO 98/40353, WO 98/50359 and WO 97/31901; EP 884050; and Hoover et al., *J. Med. Chem.*, 1998, 41, 2934–2938.

Moreover, the compounds of the present invention can be administered in combination with other pharmaceutical agents, such as a cholesterol biosynthesis inhibitor or a cholesterol absorption inhibitor, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an antioxidant or niacin. The compounds of the present invention may also be administered in combination with a naturally occurring compound that acts to lower plasma cholesterol levels. Such naturally occurring compounds are commonly called nutraceuticals and include, for example, garlic extract and niacin.

In addition, the compounds of the present invention can be used in combination with an apolipoprotein B secretion inhibitor and/or microsomal triglyceride transfer protein (MTP) inhibitor. Some preferred apolipoprotein B secretion inhibitors and/or MTP inhibitors are disclosed in commonly assigned U.S. Pat. No. 5,919,795.

A variety of apo B secretion/MTP inhibitors are known to one of ordinary skill in the art. Although any apo B secretion/MTP inhibitor may be used in the practice of the methods and pharmaceutical compositions of the present invention, generally preferred apo B secretion/MTP inhibitors include those compounds that are disclosed in, for example, European Patent Applications, Publication Nos. EP 643057, EP 719763, EP 753517, EP 764647, EP 765878, EP 779276, EP 779279, EP 799828, EP 799829, EP 802186, EP 802188, EP 802192, and EP 802197; International Patent Applications, Publication Nos. WO 96/13499, WO 96/33193, WO 96/40640, WO 97/26240, WO 97/43255, WO 97/43257, WO 98/16526 and WO 98/23593; and U.S. Pat. Nos. 5,595,872; 5,646,162; 5,684,014; 5,712,279; 5,739,135 and 5,789,197.

Especially preferred apo-B secretion/MTP inhibitors are those biphenyl-2-carboxylic acid-tetrahydroisoquinolin-6-yl amide derivatives disclosed in International Patent Applications, Publication Nos. WO 96/40640 and WO 98/23593. Especially preferred apo B secretion/MTP inhibitors disclosed in International Patent Applications, Publication Nos. WO 96/40640 and WO 98/23593, and useful in the methods and pharmaceutical compositions of the present invention, are 4'-trifluoromethyl-biphenyl-2-carboxylic acid-[2-(1H-[1,2,4]triazol-3-ylmethyl)-1,2,3,4-tetrahydroisoquin-6-yl]-amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the methods and pharmaceutical compositions of the present invention, are 9-(4-{4-[4'trifluoromethyl-biphenyl-2-carbonyl)-amino]-piperidin-1-yl}-butyl-9H-fluorene-9-carboxylic acid-(2,2,2-trifluoroethyl)-amide and 9-{4-[4-(2-benzothiazol-2-yl-benzoylamino)-piperidin-1-yl]-butyl}- 9H-fluorene-9-carboxylic acid-(2,2,2-trifluoroethyl)-amide.

Another class of especially preferred apo B secretion/MTP inhibitors is disclosed in International Patent Application, Publication No. WO 98/16526.

Especially preferred apo B secretion/MTP inhibitors disclosed in International Patent Application, Publication No. WO 98/16526, and useful in the methods and pharmaceutical compositions of the present invention, are [11a-R]-8-[(4-cyanophenyl)methoxy]-2-cyclopentyl-7-(prop-2-enyl)-2,3,11,11a-tetrahydro-6H-pyrazino[1,2b]isoquinoline-1,4-dione and [11a-R]-cyclopentyl-7-(prop-2-enyl)-8-[(pyridin-2-yl)methoxy]-2,3,11,11a-tetrahydro-6H-pyrazino[1,2b]isoquinoline-1,4-dione.

Another especially preferred class of apo B secretion/MTP inhibitors is disclosed in U.S. Pat. No. 5,684,014.

An especially preferred apo B secretion/MTP inhibitor disclosed in U.S. Pat. No. 5,684,014 and useful in the methods and pharmaceutical compositions of the present invention is 2-cyclopentyl-2-[4-(2,4-dimethyl-pyrido[2,3-b]indol-9-ylmethyl)-phenyl]-N-(2-hydroxy-1-phenyl-ethyl)-acetamide.

Yet another class of especially preferred apo B secretion/MTP inhibitors is disclosed in U.S. Pat. No. 5,646,162.

An especially preferred apo B secretion/MTP inhibitor disclosed in U.S. Pat. No. 5,646,162 and useful in the methods and pharmaceutical compositions of the present invention, is 2-cyclopentyl-N-(2-hydroxy-1-phenylethyl)-2-[4-(quinolin-2-ylmethoxy)-phenyl]-acetamide.

Additional apo B secretion/MTP inhibitors that can be used in combination with compounds identified by the present invention are disclosed in commonly assigned U.S. Nonprovisional patent application Ser. No. 09/711281, filed Nov. 9, 2000. Examples of specific preferred apo B secretion/MTP inhibitors are disclosed in that application, which is hereby incorporated by reference herein.

Specific cholesterol absorption inhibitors and cholesterol biosynthesis inhibitors are described in detail below. Additional cholesterol absorption inhibitors are known to those skilled in the art and are described, for example, in International Patent Application, Publication No. WO 94/00480.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455–509 (1981) and the references cited therein). A variety of these compounds are described and referenced below. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors include Baycol, Lescol, Lipitor, Mevacor, Pravachol and Zocor.

Any HMG-CoA synthase inhibitor may be used as an additional compound in the combination therapy aspect of this invention. The term HMG-CoA synthase inhibitor refers to a compound that inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology*, 35: 155–160 (1975); and

*Methods of Enzymology*, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors useful in the methods, compositions and kits of the present invention will be known to those skilled in the art.

Any compound that decreases HMG-CoA reductase gene expression may be used as an additional compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology*, 110: 9–19 (1985)). Several such compounds are described and referenced below; however, other inhibitors of HMG-CoA reductase gene expression will be known to those skilled in the art, for example, U.S. Pat. No. 5,041,432 discloses certain 15-substituted lanosterol derivatives that are inhibitors of HMG-CoA reductase gene expression. Other oxygenated sterols that suppress the biosynthesis of HMG-CoA reductase are discussed by E. I. Mercer (*Prog. Lip. Res.*, 32: 357–416 (1993)).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.*; 6: 1951–1954 (1996), respectively.

Preferred CETP inhibitors that can be used in combination with a compound of the present invention include those described in commonly assigned International Patent Application, Publication No. WO 00/17164, which is hereby incorporated by reference herein.

Any ACAT inhibitor can serve as an additional compound in the combination therapy aspect of this invention. The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research*, 24:1127 (1983). A variety of these compounds are described and referenced below; however, other ACAT inhibitors will be known to those skilled in the art. U.S. Pat. No. 5,510,379 discloses certain carboxysulfonates, while International Patent Applications, Publication Nos. WO 96/26948 and WO 96/10559, both disclose urea derivatives having ACAT inhibitory activity.

Any compound having activity as a squalene synthetase inhibitor can serve as an additional compound in the combination therapy aspect of the present invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology*, 15: 393–454 (1969); and *Methods of Enzymology*, 110: 359–373 (1985); and references cited therein). A summary of squalene synthetase inhibitors has been compiled in *Curr. Op. Ther. Patents*, 861-4 (1993). European Patent Application, Publication No. 0 567 026 A1 discloses certain 4,1-benzoxazepine derivatives as squalene synthetase inhibitors and their use in the treatment of hypercholesterolemia and as fungicides. European Patent Application, Publication No. 0 645 378 A1 discloses certain seven- and eight-membered heterocycles as squalene synthetase inhibitors and their use in the treatment and prevention hypercholesterolemia and fungal infections. European Patent Application, Publication No. 0 645 377 A1 discloses certain benzoxazepine derivatives as squalene synthetase inhibitors useful for the treatment of hypercholesterolemia or coronary sclerosis. European Patent Application, Publication Number 0 611 749 A1 discloses certain substituted amic acid derivatives useful for the treatment of arteriosclerosis. European Patent Application, Publication No. 0 705 607 A2 discloses certain condensed seven- and eight-membered heterocyclic compounds useful as antihypertriglyceridemic agents. International Patent Application, Publication No. WO 96/09827 discloses certain combinations of cholesterol absorption inhibitors and cholesterol biosynthesis inhibitors including benzoxazepine derivatives and benzothiazepine derivatives. European Patent Application, Publication No. 0 701 725 A1 discloses a process for preparing certain optically-active compounds, including benzoxazepine derivatives, having plasma cholesterol and triglyceride lowering activities.

Other compounds that are marketed for hyperlipidemia, including hypercholesterolemia, and which are intended to treat atherosclerosis, include bile acid sequestrants, such as Colestid, LoCholest and Questran; and fibric acid derivatives, such as Atromid, Lopid and Tricor. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. Preferred lipase inhibitors comprise gastric or pancreatic lipase inhibitors. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92:125 (1987).

A variety of lipase inhibitors are known to one of ordinary skill in the art. However, in the practice of the methods, pharmaceutical compositions, and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. The compound tetrahydrolipstatin is especially preferred.

The pancreatic lipase inhibitors lipstatin, 2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of Actinomycetes strain MG147-CF2, are disclosed in Kitahara, et al., *J. Antibiotics*, 40(11), 1647–1650 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa, et al., *J. Antibiotics*, 33, 1594–1596 (1980). The use of ebelactones A and B in the suppression of monoglyceride formation is disclosed in Japanese Kokai 08-143457, published Jun. 4, 1996.

The lipase inhibitor RHC 80267, cyclo-O,O'-[(1,6-hexanediyl)-bis(iminocarbonyl)]dioxime, and the various bis(iminocarbonyl)dioximes related thereto may be prepared as described in Petersen et al., *Liebig's Annalen*, 562, 205–229 (1949). The ability of RHC 80267 to inhibit the activity of myocardial lipoprotein lipase is disclosed in Carroll et al., *Lipids*, 27, pp. 305–307 (1992) and Chuang et al., *J. Mol. Cell Cardiol.*, 22, 1009–1016 (1990).

Any suitable dosage of a lipase inhibitor is used in aspects of the present invention comprising such inhibitors. The dosage of the lipase inhibitor is generally in the range of from about 0.01 to about 50 mg/kg body weight of the subject per day, preferably from about 0.05 to about 10 mg/kg body weight of the subject per day, administered singly or as a divided dose. For example, where the lipase inhibitor is tetrahydrolipstatin, the dosage of tetrahydrolipstatin is preferably from about 0.05 to 2 mg/kg body weight of the subject per day. In practice, the physician will determine the actual dosage of the lipase inhibitor which will be most suitable for an individual patient and it will vary with, e.g., age, weight and response of the particular patient. The above dosages of lipase inhibitors are exemplary, but there can be, of course, individual instances where higher or lower dosage ranges of such lipase inhibitors are merited, and all such dosages are within the scope of the present invention.

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

In combination with a compound of the present invention, any glucosidase inhibitor may be employed; however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods, pharmaceutical compositions and kits of the present invention, generally preferred glucosidase inhibitors are those inhibitors that are selected from the group consisting of acarbose, adiposine, voglibose, miglitol, emiglitate, MDL-25637, camiglibose, tendamistate, Al-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1-yl]amino]-glucopyranosyl-(1→4)-O-D-glucopyranosyl-(1→4)-D-glucose, the various amino sugar derivatives related thereto and a process for the preparation thereof by the microbial cultivation of Actinoplanes strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254,256. Additionally, a process for the preparation and purification of adiposine is disclosed in Namiki et al., *J. Antiobiotics*, 35: 1234–1236 (1982).

The glucosidase inhibitor voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl) piperidino]-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor Al-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of *Streptomyces dimorphongenes* strains NR-320-OM7HB and NR-320-OM7HBS, are disclosed in U.S. Pat. No. 4,273,765.

The glucosidase inhibitor pradimicin-Q and a process for the preparation thereof by the microbial cultivation of *Actinomadura verrucospora* strains R103-3 or A10102, are disclosed in U.S. Pat. Nos. 5,091,418 and 5,217,877, respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, Al-3688 and trestatin.

In another aspect of the present invention, the compounds of Formula I can be used in combination with an additional anti-obesity agent. The additional anti-obesity agent is preferably selected from the group consisting of phenylpropanolamine, ephedrine, pseudoephedrine, phentermine, a neuropeptide Y antagonist, a $_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy}acetic acid.

Suitable anorectic agents for the compositions, methods and kits of the present invention can be prepared using methods known to those skilled in the art, for example, phentermine can be prepared as described in U.S. Pat. No. 2,408,345; sibutramine can be prepared as described in U.S. Pat. No. 4,929,629; fenfluramine and dexfenfluramine can be prepared as described in U.S. Pat. No. 3,198,834; and bromocriptine can be prepared as described in U.S. Pat. Nos. 3,752,814 and 3,752,888.

Any suitable dosage of an anorectic agent is used in aspects of the present invention comprising such agents. The dosage of the anorectic agent is generally in the range of from about 0.01 to about 50 mg/kg body weight of the subject per day, preferably from about 0.1 to about 10 mg/kg body weight of the subject per day, administered singly or as a divided dose. For example, where the anorectic agent is phentermine, the dosage of phentermine is from about 0.01 to 50 mg/kg body weight of the subject per day, preferably from about 0.1 to about 1 mg/kg body weight of the subject per day. In addition, where the anorectic agent is sibutramine, the dosage range is from about 0.01 to about 50 mg/kg body weight of the subject per day, preferably from about 0.1 to about 1 mg/kg body weight of the subject per day; where the anorectic agent is dexfenfluramine or fenfluramine, the dosage range is from about 0.01 to about 50 mg/kg body weight of the subject per day, preferably from about 0.1 to about 1 mg/kg body weight of the subject per day; and where the anorectic agent is bromocriptine, the dosage range is from about 0.01 to about 10 mg/kg body weight of the subject per day, preferably from about 0.1 to about 1 mg/kg body weight of the subject per day. In practice, the physician will determine the actual dosage of the anorectic agent which will be most suitable for an individual patient and it will vary with, e.g., age, weight and response of the particular patient. The above dosages of anorectic agents are exemplary, but there can be, of course, individual instances where higher or lower dosage ranges of such anorectic agents are merited, and all such dosages are within the scope of the present invention.

The compounds of the present invention can also be used in combination with an antihypertensive agent. Examples of presently marketed products containing antihypertensive agents include calcium channel blockers, such as Cardizem, Adalat, Calan, Cardene, Covera, Dilacor, DynaCirc Procardia XL, Sular Tiazac, Vascor, Verelan, Isoptin, Nimotop Norvasc, and Plendil; and angiotensin converting enzyme (ACE) inhibitors, such as Accupril, Altace, Captopril, Lotensin, Mavik, Monopril, Prinivil, Univasc, Vasotec and Zestril. In addition, diuretics and combinations of the above antihypertensive agents have been employed and are contemplated to be used in combination with a compound of the present invention.

The compounds of the present invention can also be used in combination with an antidepressant. Examples of marketed antidepressants that can be used in combination with a compound of the present invention include monoamine oxidase inhibitors such as Nardil and Parnate; selective serotonin reuptake inhibitors, such as Paxil, Prozac, and Zoloft; triclyclics, such as Asendin, Elavil, Etrafon, Limbitrol, Norpramin Pamelor, Sinequan, Surmontil, Tofranil, Triavil, and Vivactil. Additional compounds that are used to treat depression and that can be used in combination with a compound of the present invention include Desyrel, Effexor, Remeron, Serzone, and Wellbutrin.

The compounds of the present invention can also be used in combination with a compound useful to treat osteoporosis. Examples of marketed products containing active agents that can be used in combination with a compound of the present invention include biphosphonates such as Fosamax and hormonal agents such as calcitonin and estrogens. In addition, Evista may be used in combination with a compound of the present invention.

The compounds of the present invention can also be used in combination with a compound useful to regrow hair. Currently, there are two drugs approved by the United States Food and Drug Administration for the treatment of male pattern baldness: topical minoxidil (marketed as Rogaine by Pharmacia), and oral finasteride (marketed as Propecia by Merck & Co., Inc.).

The compounds of the present invention are administered to a patient in a therapeutically effective amount. The compounds can be administered alone or as part of a pharmaceutically acceptable composition. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially in any order. For example, in the case of tablets, the compounds may be found in one tablet or in separate tablets, which can be administered at once or sequentially. In addition, it should be recognized that the compositions may be different forms. For example, one or more compounds may be delivered via a tablet, while another is administered via injection or orally as a syrup. All combinations, delivery methods and administration sequences are contemplated.

For sequential administration, a compound, a prodrug, an isomer or a pharmaceutically acceptable salt of the present invention and another active compound, as the case may be, can be administered in any order. It is generally preferred that such administration be oral. It is even more preferred that the administration be oral and simultaneous. However, for example, if the subject being treated is unable to swallow, or oral absorption is otherwise impaired or undesirable, parenteral or transdermal administration will be appropriate. Where the administration is sequential, the administration of a compound, prodrug, isomer or pharmaceutically acceptable salt of the present invention and another active compound, as the case may be, can be by the same method or by different methods.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, a prodrug thereof, or a salt of such compound or prodrug; and an additional pharmaceutically active compound. The kit may also comprise more than two separate pharmaceutical compositions, one composition containing a compound of the present invention, a prodrug thereof, or a salt of such compound or prodrug; and the other compositions containing additional pharmaceutically active compounds. The kit comprises a container for containing the separate compositions, such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of compounds of the present invention can consist of one tablet or capsule, while a daily dose of the second compound can consist of several tablets or capsules and vice versa. The memory aid should reflect this and aid in correct administration of the active agents.

In another embodiment of the present invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Any suitable route of administration may be used for the compounds of Formula I, isomers, prodrugs and pharmaceutically acceptable salts thereof, in the present invention. The compounds of the present invention and other pharmaceutically active agents, if desired, can be administered to a patient orally, rectally, parenterally, (for example, intravenously, intramuscularly, or subcutaneously) intracisternally, intravaginally, intraperitoneally, intravesically, topically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound or compounds in a delayed manner. Examples of embedding compositions that can be used are polymeric substances and waxes. The compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and/or sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration are preferably suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the compound.

Dosage forms for topical administration of a compound of the present invention may include ointments, powders, sprays and inhalants. The compound or compounds are admixed under sterile condition with a physiologically acceptable carrier, and any preservatives, buffers, or propellants that may be required. Opthalmic formulations, eye ointments, powders, and solutions are also contemplated as being within the scope of this invention.

For example, for the treatment of hair loss, the compounds of the present invention are preferably administered as topical compositions. The carrier of the topical composition preferably aids penetration of the present compounds into the skin to reach the environment of the hair follicle. Topical compositions of the present invention may be in any form including, for example, solutions, oils, creams, ointments, gels, lotions, shampoos, leave-on and rinse-out hair conditioners, milks, cleansers, moisturizers, sprays, skin patches, and the like.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2, myristyl propionate, and the like. Other materials suitable for use in topical carriers include, for example, emollients, solvents, humectants, thickeners and powders. Examples of each of these types of materials, which can be used singly or as mixtures of one or more materials, are set forth in several patent publications relating to treatment of hair loss, including, for example, International Patent Application Publication No. WO 00/72810, published Dec. 7, 2000; International Patent Application Publication No. WO 00/72811, published Dec. 7, 2000, International Patent Application Publication No. WO 00/72812, published Dec. 7, 2000; International Patent Application Publication No. WO 00/72813, published Dec. 7, 2000; International Patent Application Publication No. WO 00/72920, published Dec. 7, 2000; and International Patent Application Publication No. WO 00/73292, published Dec. 7, 2000; and references cited therein. All of these patent publications are hereby incorporated by reference herein.

The topical compositions of the present invention may also optionally comprise an activity enhancer. The activity enhancer can be chosen from a wide variety of molecules which can function in different ways to enhance hair growth effects of a compound of the present invention. Particular classes of activity enhancers include other hair growth stimulants and penetration enhancers. Examples of other hair growth stimulants and penetration enhancers as well as other methods of administration for hair loss treatment, such as liposome delivery systems and iontophoresis are set forth in the patent publications, referred to above. The Telogen Conversion Assay which measures the potential of a test compound to convert mice in the resting stage of the hair growth cycle ("telogen"), to the growth stage of the hair growth cycle ("anagen"), is also described in the patent publications, referred to above.

The compounds of the present invention can be administered to a patient at dosage levels in the range of about 0.7 to about 7,000 mg per day. For a normal adult human having a body weight of about 70 kg, a dosage in the range of about 0.001 to about 100 mg per kilogram body weight is typically sufficient. Even more preferably, the dosage may be in the range of about 0.001 to about 10 mg per kilogram body weight. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in the art in view of this disclosure. It is also noted that the compounds of the present invention can be used in sustained release, controlled release, and delayed release formulations. Such formulations and their preparation are within the ordinary skill in the art in view of the present disclosure.

The compounds, prodrugs, isomers and pharmaceutically acceptable salts of this invention are also administered to a mammal other than a human. The method of administration and the dosage to be administered to such a mammal will depend, for example, on the animal species and the disease or disorder being treated. The compounds, prodrugs, isomers and pharmaceutically acceptable salts of the present invention may be administered to animals in any suitable manner, e.g., orally, parenterally or transdermally, in any suitable form such as, for example, a capsule, bolus, tablet, pellet, e.g., prepared by admixing a compound, prodrug, isomer or pharmaceutically acceptable salt of the present invention with a suitable diluent such as carbowax or carnuba wax together with a lubricant, liquid drench or paste, e.g., prepared by dispersing a compound, prodrug, isomer or pharmaceutically acceptable salt of the present invention in a pharmaceutically acceptable oil such as peanut oil, sesame oil or corn oil. The compounds, prodrugs, isomers and pharmaceutically acceptable salts of the present invention may also be administered to animals as an implant. Such formulations are prepared in a conventional manner in accordance with standard veterinary practice.

As an alternative, the compounds, prodrugs, isomers and pharmaceutically acceptable salts of the present invention may be administered with the water supply, e.g., in the form of a liquid or water-soluble concentrate. In addition, the compounds, prodrugs, isomers and pharmaceutically acceptable salts of this invention may be administered in the animal feedstuff, e.g., a concentrated feed additive or premix may be prepared for mixing with the normal animal feed, commonly along with a suitable carrier therefor. The carrier facilitates uniform distribution of a compound, prodrug, isomer or pharmaceutically acceptable salt of the present invention, e.g., in the finished feed with which the premix is blended. Suitable carriers include, but are not limited to, liquids, e.g., water, oils such as soybean, corn, cottonseed, or volatile organic solvents, and solids, e.g., a small portion of the feed or various suitable meals including alfalfa, soybean, cottonseed oil, linseed oil, corncob, corn, molasses, urea and bone, and mineral mixes.

The utility of the compounds of Formula I, isomers thereof, prodrugs of said compounds or isomers, or pharmaceutically acceptable salts of said compounds, isomers or prodrugs, are demonstrated by activity in one or more of the assays described below:

Assay 1

Oxygen Consumption

As would be appreciated by those skilled in the art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity. As is well known by those skilled in the art, thyroid hormones affect cardiac functioning, for example, by causing an increase in the heart rate and, accordingly, an increase in oxygen consumption with concomitant heat production.

The ability of compounds of the present invention to generate a thermogenic response may be demonstrated according to the following protocol.

A. Experimental

This in vivo assay is designed to evaluate the efficacy and cardiac effects of compounds that are tissue-selective thyroid hormone agonists. The efficacy endpoints measured are whole body oxygen consumption and the activity of liver mitochondrial alpha-glycerophosphate dehydrogenase ("mGPDH"). The cardiac endpoints that are measured are heart weight and heart mGPDH activity. The protocol involves: (a) dosing fatty Zucker rats for about 6 days, (b) measuring oxygen consumption and (c) harvesting tissue for preparation of mitochondria and subsequent assaying of enzyme activity thereby.

B. Preparation of Rats

Male fatty Zucker rats having a body weight range of from about 400 g to about 500 g are housed for from about 3 to about 7 days in individual cages under standard laboratory conditions prior to the initiation of the study.

A compound of Formula I, or a pharmaceutically acceptable salt, prodrug or salt of a prodrug of a compound of Formula I, vehicle, or $T_3$ sodium salt, is administered by oral gavage as a single daily dose given between about 3 p.m. to about 6 p.m. for about 6 days. A compound of Formula I, or a pharmaceutically acceptable salt or prodrug or salt of the prodrug of a compound of Formula I, or $T_3$ sodium salt is dissolved in a suitably small volume of about 1N NaOH and then brought up to a suitable volume with about 0.01N NaOH containing about 0.25% of methyl cellulose (10:1, 0.01N NaOH/MC:1N NaOH). The dosing volume is about 1 ml.

C. Oxygen Consumption

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment.

The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 l/min to about 1.7 l/min.

The Oxymax software then calculates the oxygen consumption (ml/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 minutes for about 5 hours to about 6.5 hours. Resting oxygen consumption is calculated on individual rats by averaging the values excluding the first 5 values and the values obtained during time periods where ambulatory activity exceeds about 100 counts.

Assay 2

Binding to Thyroid Hormone Receptors

The ability of a compound of Formula I, or an isomer thereof, or a pharmaceutically acceptable salt of such compound or isomer ("the test thyromimetic compound") to bind to thyroid hormone receptors can be demonstrated in the following protocol:

A. Preparation of Insect Cell Nuclear Extracts

High Five cell pellets (BTI-TN-5B1-4, catalog number B855-02, Invitrogen®, Carlsbad, Calif.) obtained about 48 hours after infection with baculovirus (GibcoBRL®, Gaithersburg, Md.) expressing either human TR or TR are suspended in ice cold Sample Buffer (10 mM Tris, pH 8.0; 1 mM $MgCl_2$; 1 mM DTT; 0.05% Tween 20; 1 mM 4-(2-aminoethyl)-benzenesulfonylfluoride; 25 µg/ml leupeptin). After about 10 minutes incubation on ice, the suspension is homogenized by 20 strokes with a Dounce homogenizer (VWR® Scientific Products, West Chester, Pa.) and centrifuged at 800×g for about 15 minutes at 4 C. The pellet (nuclei) is suspended in a hypertonic buffer (0.4M KCl; 10 mM Tris, pH 8.0; 1 mM $MgCl_2$; 1 mM DTT; 0.05% Tween 20) and incubated for about 30 min on ice. The suspension is centrifuged at 100,000×g for about 30 minutes at 4 C. The supernatant (nuclear extract) is stored in 0.5 ml aliquots at −80 C.

B. Binding Assay

Competition binding assays to measure the interaction of the test compounds with thyroid hormone receptor 1 and 1 (TR and TR) are carried out according to the following protocol:

Solutions of test compounds (final compound concentration of 20 mM) are prepared using 100% DMSO as a solvent. Each compound is serially diluted in an assay buffer (5 mM Tris-HCl, pH 8.0; 50 mM NaCl; 2 mM EDTA; 10% (v/v) glycerol; 1 mM DTT) containing 0.4 nM $^{125}$I-$T_3$ (specific activity of about 2200 Ci/mmol) to yield solutions that vary in compound concentration from about 10 µM to about 0.1 nM.

High Five insect cell nuclear extract containing either TR or TR is diluted to a total protein concentration of 0.0075 mg/ml using the assay buffer as diluent.

One volume (100 µl) of each compound dilution (containing 0.4 nM $^{125}$I-T3) is combined with an equal volume (100 µl) of diluted nuclear extract containing TR or TR, and incubated at room temperature for about 90 min. A one hundred and fifty µl sample of the binding reaction is removed and placed into a 96-well filter plate (Millipore®, Bedford, Mass.) that has been pre-washed with ice-cold assay buffer. The plate is subjected to vacuum filtration using a filtration manifold (Millipore®). Each well is washed five times by the addition of 200 µl of ice-cold assay buffer and subsequent vacuum filtration. The plate is removed from the vacuum filtration manifold, the bottom of the plate is briefly dried on paper towels, then 25 µl of Wallace® (EG&G Wallac, Gaithersburg, Md.) Optiphase Supermix scintillation cocktail is added to each well and the top of the plate is covered with plastic sealing tape (Microplate Press-on Adhesive Sealing Film, Packard®

Instrument Co., Inc., Downers Grove, Ill.) and the radioactivity is quantitated using a Wallace® Microbeta 96-Well plate scintillation counter. The binding activity is then calculated by dividing the amount of $^{125}$I-T3 bound in the presence of increasing amounts of the test compound relative to the amount of $^{125}$I-T3 bound in the absence of a test compound (expressed as % of control) and then linear regression analysis is used to determine the $IC_{50}$.

EXAMPLE 1

5-(4-Hydroxy-3-isopropyl-phenoxy)-4,6-dimethyl-1H-indole-2-carboxylic acid

Step A: Preparation of 4-(3-lsopropyl-4-methoxy-phenoxy)-3,5-dimethyl-nitrobenzene The product was prepared by coupling 2,6-dimethyl-4-nitrophenol with (3,3'-diisopropyl-4,4'-dimethoxydiphenyl) iodonium tetrafluoroborate in the presence of copper powder and triethylamine according to the procedure described in the *J. Med. Chem.* 38, 695–707(1991).

Step B: Preparation of 4-(4-Amino-2,6-dimethyl-phenoxy)-2-isopropyl-phenol

To a solution of 4-(3-isopropyl-4-methoxy-phenoxy)-3,5-dimethyl-nitrobenzene (500 mg, 1.6 mmol) in methylene chloride (12 mL) at room temperature was added boron tribromide (1M in methylene chloride, 3.2 mL, 3.2 mmol). After stirring at room temperature for 1 hour, the reaction was quenched with water (15 mL) and 1M HCl (10 mL). The resulting mixture was stirred at room temperature for 30 minutes and the solution was extracted with methylene chloride (3 times 20 mL). The combined organic extracts were washed with brine (50 mL), dried ($Na_2SO_4$), filtered, and concentrated to give the demethylated nitro product. The nitro compound was dissolved in ethyl acetate/ethanol (3:1, 40 mL), to which was added 10% palladium on carbon (100 mg). The mixture was put on Parr shaker for 2 hours at room temperature under 50 psi hydrogen gas and then filtered through Celite®. The filtrate was concentrated to give the title compound as a brown solid (458 mg) which was used in the next step without further purification. $^1$H NMR (400 MHz, $CDCl_3$) δ6.51 (d, 1H), 6.45 (d, 1H), 6.39 (s, 2H), 6.14–6.12 (dd, 1H), 4.06 (br s, 2H), 3.10–3.06 (m, 1H), 1.90 (s, 6H), 1.01 (d, 6H). MS (APCI$^-$) Calc: 271.2, Found: 270.2 (M−1).

Step C: Preparation of 2-{[4-(4-Hydroxy-3-isopropyl-phenoxy)-3,5-dimethyl-phenyl]-hydrazono}-propionic acid ethyl ester To a solution of 4-(4-amino-2,6-dimethyl-phenoxy)-2-isopropyl-phenol (136 mg, 0.50 mmol) in a mixture of ethanol (2 mL) and hydrochloric acid (12M, 0.17 mL) at 0° C. was added slowly a solution of sodium nitrite (45 mg, 0.65 mmol) in water (0.5 mL). After stirring at 0° C. for 30 minutes, the diazonium solution was added dropwise into a solution of ethyl-2-methyl acetoacetate (87 mg, 0.60 mmol) in ethanol (1 mL) and 1N sodium hydroxide (2.26 mL) at 0° C. The resulting mixture was warmed to room temperature, stirred for 1 hour, then diluted with water (10 mL) and 1M hydrochloric acid (1 mL), and extracted with ethyl acetate (15 mL). The organic layer was separated, washed with 1M hydrochloric acid (15 mL), brine (15 mL), dried ($Na_2SO_4$), filtered, and concentrated to give the title compound (193 mg) which was used in the next step without further purification. MS (APCI$^-$) Calc: 384.2, Found: 383.3 (M−1).

Step D: Preparation of 5-(4-Hydroxy-3-isopropyl-phenoxy)-4,6-dimethyl-1H-indole-2-carboxylic acid ethyl ester A mixture of p-toluenesulfonic acid (130 mg, 0.75 mmol) and 2-{[4-(4-hydroxy-3-isopropyl-phenoxy)-3,5-dimethyl-phenyl]-hydrazono}-propionic acid ethyl ester (193 mg, 0.50 mmol) in toluene (2 mL) was heated to reflux for 2 hours and then cooled to room temperature. Saturated aqueous $NaHCO_3$ (10 mL) and ehtyl acetate (25 mL) were added. The organic layer was separated, washed with saturated $NaHCO_3$ (2 times 25 mL), 1M hydrochloric acid (25 mL), brine (25 mL), dried ($Na_2SO_4$), filtered, and concentrated. The residue was purified by preparative thin layer chromatography (3% methanol in methylene chloride ) to afford the title compound (60 mg) as a solid. $^1$H NMR (400 MHz, $CDCl_3$) δ8.82 (s, 1H), 7.20 (s, 1H), 7.09 (s, 1H), 6.74 (d, 1H), 6.55 (d, 1H), 6.28–6.25 (m, 1H), 4.41–4.35 (q, 2H), 3.15–3.11 (m, 1H), 2.30 (s, 3H), 2.20 (s, 3H), 1.40 (t, 3H), 1.18 (d, 6H). MS (APCI$^-$) Calc: 367.2, Found: 366.3 (M−1).

Step E: Preparation of 5-(4-Hydroxy-3-isopropyl-phenoxy)-4,6-dimethyl-1H-indole-2-carboxylic acid To a solution of 5-(4-hydroxy-3-isopropyl-phenoxy)-4,6-dimethyl-1H-indole-2-carboxylic acid ethyl ester (60 mg, 0.16 mmol) in methanol/water (1:1, 3.2 mL) at room temperature was added 3N potassium hydroxide (324 μL). After stirring at room temperature for 2 hours, the mixture was diluted with water (10 mL) and washed with ethyl acetate. The aqueous solution was acidified with 1 M hydrochloric acid and then extracted with ethyl acetate (3 times 25 mL). The combined organic extracts were dried ($Na_2SO_4$), filtered, and concentrated to afford the title compound (30 mg) as a solid. $^1$H NMR (400 MHz, $CD_3OD$) δ11.07 (s, 1H), 7.16 (s, 2H), 6.62 (d, 1H), 6.57 (d, 1H), 6.25–6.22 (dd, 1H), 3.24–3.19 (m, 1H), 2.27 (s, 3H), 2.17 (s, 3H), 1.12 (d, 6H). MS (APCI$^-$) Calc: 339.1, Found: 338.2 (M−1).

Using the appropriate starting materials, EXAMPLES 1-1 to 1-4 were prepared in an analogous manner to the sequence of reactions described for EXAMPLE 1.

EXAMPLE 1-1

4.6-Dichloro-5-(4-hydroxy-3-isopropyl-phenoxy)-1H-indole-2-carboxylic acid ethyl ester $^1$H NMR (400 MHz, $CDCl_3$) δ7.42 (s, 1H), 7.23 (d 1H), 6.76 (d, 1H), 6.56 (d, 1H), 6.32–6.29 (dd, 1H), 4.38–4.33 (q, 2H), 3.20–3.13 (m, 1H), 1.36 (t, 3H), 1.14 (d, 6H). MS (APCI$^-$) Calc: 407.0, Found: 406.2 (M−1).

EXAMPLE 1-2

5-(3-sec-Butyl-4-hydroxy-phenoxy)-4,6-dimethyl-1H-indole-2-carboxylic acid ethyl ester $^1$H NMR (400 MHz, $CDCl_3$) δ7.12 (s, 1H), 7.03 (s, 1H), 6.55 (d, 1H), 6.50 (d, 1H), 6.23–6.20 (dd, 1H), 4.32–4.27 (q, 2H), 2.91–2.86 (m, 1H), 2.23 (s, 3H), 2.12 (s, 3H), 1.51–1.36 (m, 2H), 1.32 (t, 3H), 1.04 (d, 3H), 0.73 (t, 3H). MS (APCI$^-$) Calc: 381.2, Found: 380.3 (M−1).

EXAMPLE 1-3

5-(3-sec-Butyl-4-hydroxy-phenoxy)-4,6-dimethyl-1H-indole-2-carboxylic acid $^1$H NMR (400 MHz, $CD_3OD$) δ7.18 (s, 2H), 6.63 (d, 1H), 6.56 (d, 1H), 6.33–6.30 (dd, 1H), 3.04–2.98 (m, 1H), 2.30 (s, 1H), 2.20 (s, 1H), 1.56–1.45 (m, 2H), 1.12 (d, 3H), 0.82 (t, 3H). MS (APCI$^-$) Calc: 353.2, Found: 352.2 (M−1).

EXAMPLE 1-4

4,6-Dichloro-5-(4-hydroxy-3-isopropyl-phenoxy)-1H-indole-2-carboxylic acid $^1$H NMR (400 MHz, $CD_3OD$) δ7.53 (s, 1H), 7.15 (s, 1H), 6.64 (d, 1H), 6.57 (d, 1H), 6.29–6.26 (dd, 1H), 3.23–3.16 (m, 1H), 1.12 (d, 6H). MS (APCI$^-$) Calc: 379.0, Found: 378.1 (M−1).

EXAMPLE 2

4,6-Dichloro-5-(4-hydroxy-3-isopropyl-phenoxy)-1-methyl-1H-indole-2-carboxylic acid Step A: Preparation of 4,6-Dichloro-5-(3-isopropyl-4-methoxy-phenoxy)-1H-indole-2-carboxylic acid ethyl ester 4,6-Dichloro-5-(3-isopropyl-4-methoxy-phenoxy)-1H-indole-2-carboxylic acid ethyl ester was prepared from 4-(3-isopropyl-4-methoxy-phenoxy)-3,5-dichloro-nitrobenzene according to the procedures described in EXAMPLE 1, Steps A, B, C and D. $^1$H NMR (400 MHz, CDCl$_3$) δ9.18 (s, 1H), 7.50 (s, 1H), 7.34 (d, 1H), 6.91 (d, 1H), 6.70(d, 1H), 6.48–6.44 (dd, 1H), 4.50–4.43 (q, 2H), 3.80 (s, 3H), 3.35–3.26 (m, 1H), 1.46 (t, 3H), 1.20 (d, 6H). MS (APCI$^-$) Calc: 421.1, Found: 420.2 (M−1).

Step B: Preparation of 4,6-Dichloro-5-(3-isopropyl-4-methoxy-phenoxy)-1-methyl-1H-indole-2-carboxylic acid methyl ester To a solution of 4,6-dichloro-5-(3-isopropyl-4-methoxy-phenoxy)-1H-indole-2-carboxylic acid ethyl ester (50 mg, 0.12 mmol) in N,N-dimethylformamide (1 mL) at 0° C. was added sodium hydride (60% dispersion in mineral oil, 4.3 mg, 0.18 mmol) and the mixture was stirred at 0° C. for 30 minutes. To which at 0° C. was added iodomethane (15 μL, 0.24 mmol). The solution was warmed to room temperature, stirred for 19 hours, quenched with 1M hydrochloric acid (15 mL) and extracted with ethyl acetate (15 mL). The organic extract was washed with 1M hydrochloric acid (4 times 20 mL), brine (20 mL), dried (Na$_2$SO$_4$), filtered, and concentrated. The residue was purified by preparative thin layer chromatography (50% CH$_2$Cl$_2$ in hexane) to afford the title compound (46 mg). $^1$H NMR (400 MHz, CDCl$_3$) δ7.42 (s, 1H), 7.33 (s, 1H), 6.85 (d, 1H), 6.65 (d, 1H), 6.42–6.39 (dd, 1H), 4.05 (s, 3H), 3.91 (s, 3H), 3.91 (s, 3H), 3.74 (s, 3H), 3.27–3.23 (m, 1H), 1.15 (d, 6H).

Step C: Preparation of 4,6-Dichloro-5-(4-hydroxy-3-isopropyl-phenoxy)-1-methyl-1H-indole-2-carboxylic acid methyl ester To a solution of 4,6-dichloro-5-(3-isopropyl-4-methoxy-phenoxy)-1-methyl-1H-indole-2-carboxylic acid methyl ester (46 mg, 0.11 mmol) in dry methylene chloride (1 mL) at room temperature was added boron tribromide (1M in methylene chloride, 0.22 mL, 0.22 mmol). After stirring at room temperature for 1.5 hours, the reaction was quenched with methanol (0.5 mL), stirred for 15 minutes, then diluted with water (10 mL), and stirred for another 15 minutes. The solution was extracted with methylene chloride (3 times 5 mL). The combined organic extracts were dried (Na$_2$SO$_4$), filtered, and concentrated. The residue was purified by preparative thin layer chromatography (3% methanol in methylene chloride) to afford the title compound (32 mg). $^1$H NMR (400 MHz, CDCl$_3$) δ7.42 (s, 1H), 7.34 (s, 1H), 6.83 (d, 1H), 6.60 (d, 1H), 6.39–6.36 (dd, 1H), 4.05 (s, 3H), 3.92 (s, 3H), 3.19–3.12 (m, 1H), 1.21 (d, 6H). MS (APCI$^-$) Calc: 407.1, Found: 406.2 (M−1).

Step D: Preparation of 4,6-Dichloro-5-(4-hydroxy-3-isopropyl-phenoxy)-1-methyl-1H-indole-2-carboxylic acid To a solution of 4,6-dichloro-5-(4-hydroxy-3-isopropyl-phenoxy)-1-methyl-1H-indole-2-carboxylic acid methyl ester (32 mg, 0.078 mmol) in 50% aqueous MeOH (4 mL) was added potassium hydroxide (3N, 154 μL). The resulting solution was stirred for 19 hours at room temperature, diluted with potassium hydroxide (0.1N, 16 mL) and the solution was washed with EtOAc (3 times 10 mL). The aqueous solution was acidified with concentrated hydrochloric acid and then extracted with ethyl acetate (3 times 15 mL). The combined organic extracts were washed with brine, dried (Na$_2$SO$_4$), filtered, and concentrated to afford the title compound (23 mg). $^1$H NMR (400 MHz, CD$_3$OD) δ7.64 (s, 1H), 7.24 (s, 1H), 6.63 (d, 1H), 6.57 (d, 1H), 6.29–6.26 (dd, 1H), 4.03 (s, 3H), 3.22–3.15 (m, 1H), 1.11 (d, 6H). MS (APCI$^-$) Calc: 393.0, Found: 392.2 (M−1).

Using the appropriate starting materials, EXAMPLE 2-1 was prepared in an analogous manner to the sequence of reactions described for EXAMPLE 2.

EXAMPLE 2-1

5-(3-sec-Butyl-4-hydroxy-phenoxy)-1,4,6-trimethyl-1H-indole-2-carboxylic acid $^1$H NMR (400 MHz, CD$_3$OD) δ7.23 (s, 1H), 7.15 (s, 1H), 6.57 (d, 1H), 6.50 (d, 1H), 6.27–6.24 (dd, 1H), 3.99 (s, 3H), 2.98–2.93 (m, 1H), 2.24 (s, 3H), 2.19 (s, 3H), 1.53–1.43 (m, 2H), 1.06 (d, 3H), 0.76 (t, 3H). MS (APCI$^-$) Calc: 367.2, Found: 366.3 (M−1).

EXAMPLE 3

5-[3-(Cyclobutyl-methyl-carbamoyl)-4-hydroxy-phenoxy]4,6-dimethyl-1H-indole-2-carboxylic acid Step A: Preparation of 4-(4-methoxy-phenoxy)-3,5-dimethyl-nitrobenzene To a solution of 4-methoxyphenol (6.70 g, 53.9 mmol) and 4-chloro-3,5-dimethyl nitrobenzene (10 g, 53.9 mmol) in N-methylpyrrolidinone (50 mL) at room temperature was added potassium carbonate (8.19 g, 59.3 mmol). The reaction mixture was heated to 125° C. and stirred for 20 hours. The solution was cooled to room temperature, diluted with water (500 mL), and extracted with methylene chloride (3 times 300 mL). The combined organic extracts were washed with potassium hydroxide (0.1N, 3 times 500 mL), water (500 mL), brine (500 mL), dried (Na$_2$SO$_4$), filtered, and concentrated. The residue was dissolved in a mixture of ether (20 mL) and petroleum ether (30 mL) and the title compound was crystalized as a brown solid (6.84 g). The mother liquor was concentrated and purified by column chromatography (20% methylene chloride in hexane to 27.5% methylene chloride in hexane) to give an additional product (0.88 g) and the unreacted starting material (3.4 g). $^1$H NMR (400 MHz, CDCl$_3$) δ7.97 (s, 2H), 6.78 (d, 2H), 6.64 (d, 2H), 3.74 (s, 3H), 2.18 (s, 6H).

Step B: Preparation of 5-(2,6-Dimethyl-4-nitro-phenoxy)-2-methoxy-benzaldehyde

To a solution of 4-(4-methoxy-phenoxy)-3,5-dimethyl-nitrobenzene (7.0 g, 25.6 mmol) in trifluoroacetic acid (60 mL) at room temperature was added hexamethylenetetramine (5.75 g, 41.0 mmol). The resulting mixture was stirred at 75° C. for 6 hours and then concentrated. To the residue was added water (150 mL), stirred at room temperature for 19 hours, extracted with 10% methanol in methylene chloride (4 times 50 mL) and ethyl acetate (75 mL). The combined organic extracts were dried over Na$_2$SO$_4$, filtered, and concentrated. The product (6.56 g) was crystallized from dissolving in a minimum amount of Et$_2$O. $^1$H NMR (400 MHz, CDCl$_3$) δ10.40 (s, 1H), 8.00 (s, 2H), 7.07–7.04 (s+d, 2H), 6.95 (d, 1H), 3.90 (s, 3H), 2.18 (s, 6H). MS (APCI$^-$) Calc: 301.0, Found: 300.0 (M−1).

Step C: Preparation of 5-(2,6-Dimethyl-4-nitro-phenoxy)-2-methoxy-benzoic acid

To a solution of 5-(2,6-dimethyl-4-nitro-phenoxy)-2-methoxy-benzaldehyde (6.6 g, 21.8 mmol) and 2-methyl-2-butene (23.0 g, 327 mmol) in a mixture of tetrahydrofuran (31 mL) and t-butyl alcohol (210 mL) at room temperature was added dropwise a solution of sodium chlorite (17.7 g, 196 mmol) in KH$_2$PO$_4$ (0.6 M, 254 mL). The resulting mixture was stirred at room temperature for 16 hours, and then saturated aqueous Na$_2$S$_2$O$_3$ (100 mL) was added. The solution was stirred at room temperature for 30 minutes and extracted with ethyl acetate (3 times 300 mL). The combined organic extracts were dried over Na$_2$SO$_4$ and concentrated to afford the title compound (7.7 grams) as a crude product. The product was used in the next step without purification. $^1$H NMR (400 MHz, CDCl$_3$) δ8.01 (s, 2H), 7.49 (s, 1H), 7.02 (s, 2H), 4.06 (s, 3H), 2.19 (s, 6H). MS (APCI$^-$) Calc: 317.3, Found: 316.3 (M−1).

Step D: Preparation of N-Cyclobutyl-5-(2,6-dimethyl-4-nitro-phenoxy)-2-methoxy-benzamide To a solution of 5-(2,6-Dimethyl-4-nitro-phenoxy)-2-methoxy-benzoic acid (2.0 g, 6.3 mmol) in tetrahydrofuran (60 mL) at 0° C. under nitrogen was added N-methylmorpholine (1.4 mL) and isobutyl chloroformate (1.3 g, 9.5 mmol). The resulting mixture was stirred for 25 minutes at 0° C., and cyclobutyl amine (0.9 g, 13 mmol) was added in a single portion at 0° C. The reaction solution was stirred for another 30 minutes at 0° C. and warmed to room temperature over 1 hour. The solution was then concentrated to a viscous oily solid which was partitioned between water (25 mL) and methylene chloride (25 mL). The organic phase was separated and the aqueous phase was extracted with methylene chloride (10 mL). The combined organic extracts were washed with saturated aqueous NaHCO$_3$, 1N hydrochloric acid and brine, dried over Na$_2$SO$_4$, filtered, and concentrated. To the residue was purified by column chromatography (Et$_2$O/methylene chloride/hexane=1/7/12) to afford the title compound (1.67 grams) as a crude product. $^1$H NMR (400 MHz, CDCl$_3$) δ8.04 (br s, 1H), 7.98 (s, 2H), 7.54 (d, 1H), 6.90 (d, 1H), 6.86 (dd, 1H), 4.51–4.49 (m, 1H), 3.94 (s, 3H), 2.41–2.38 (m, 2H), 2.17 (s, 6H), 1.95–1.90 (m, 2H), 1.80–1.75 (m, 2H). MS (APCI$^+$) Calc: 370.4, Found: 371.2 (M+1).

Step E: Preparation of N-Cyclobutyl-5-(2,6-dimethyl-4-nitro-phenoxy)-2-methoxy-N-methyl-benzamide To a solution of N-Cyclobutyl-5-(2,6-dimethyl-4-nitrophenoxy)-2-methoxy-benzamide (1.67 grams, 4.51 mmol) in N,N-dimethylformamide (50 mL) at 0° C. under nitrogen was added NaH (60% dispersion in mineral oil, 0.27 grams, 11 mmol). After stirring 30 minutes at 0° C., iodomethane (3.2 g, 23 mmol) was added at 0° C. The reaction mixture was allowed to warm to room temperature and stirred at room temperature for 16 hours, poured into water (450 mL), and extracted with ethyl acetate (3 times 75 mL). The combined organic extracts were washed with water (5 times 200 mL), dried over Na$_2$SO$_4$, filtered, and concentrated. The residue was purified by column chromatography (20% ethyl acetate in hexane to 40% ethyl acetate in hexane) to afford the title compound (1.65 grams) as an off white foam. $^1$H NMR (400 MHz, CDCl$_3$) δ7.96 (s, 2H), 6.80–6.52 (m, 3H, 2 rotomers observed), 5.04, 4.02–3.98 (m, m, 1H, 2 rotomers observed), 3.74, 3.67 (s,s, 3H, 2 rotomers observed), 3.02, 2.75 (s,s, 3H, 2 rotomers observed), 2.25–1.94 (m, 9H, 2 rotomers observed), 1.75–1.41 (m, 3H, 2 rotomers observed). MS (APCI$^+$) Calc: 384.0, Found: 385.2 (M+1).

Step F: Preparation of 5-(4-Amino-2,6-dimethyl-phenoxy)-N-cyclobutyl-2-hydroxy-N-methyl-benzamide To a solution of N-Cyclobutyl-5-(2,6-dimethyl-4-nitro-phenoxy)-2-methoxy-N-methyl-benzamide (1.65 grams, 4.3 mmol) in methylene chloride (35 mL) at room temperature was added slowly boron tribromide (1M in methylene chloride, 8.6 mL, 8.6 mmol). The resulting mixture was stirred at room temperature for 4 hours, and quenched by pouring into ice water (100 mL), stirred for 1 hour at room temperature, then extracted with methylene chloride (3 times 30 mL). The combined organic extracts were washed with saturated aqueous NaHCO$_3$, brine, dried over Na$_2$SO$_4$, filtered, and concentrated to give 2-hydroxy-N-methyl benzamide as a brown solid which was subjected directly to hydrogenation without further purification. $^1$H NMR (400 MHz, CDCl$_3$) δ9.43 (s, 1H), 8.00 (s, 2H), 6.97–6.93 (d+dd, 2H), 6.42 (d, 1H), 4.44 (m, 1H), 2.96 (s, 3H), 2.22 (s, 6H), 2.19–2.14 (m, 2H), 1.87–1.55 (m, 4H). MS (APCI$^+$) Calc: 370.2, Found: 371.2 (M+1).

To 2-hydroxy-N-methyl benzamide in a mixture of ethanol/ethyl acetate (30 mL/10 mL) was added 10% palladium on carbon (0.16 grams). The reaction mixture was placed on Parr shaker for 4 hours under 50 p.s.i. hydrogen gas at room temperature. The solution was filtered through Celite® and concentrated to afford the title compound (1.33 grams) as a tan solid. The product was used in the next step without purification. $^1$H NMR (400 MHz, CDCl$_3$) δ9.37 (s, 1H), 6.96–6.89 (dd+d, 2H), 6.42–6.39 (d+s, 3H), 4.47–4.42 (m, 1H), 3.48 (br s, 2H), 2.94 (s, 3H), 2.16 −2.04 (m, 2H), 2.01 (s, 6H), 2.00–1.85 (m, 2H), 1.66–1.61 (m, 1H), 1.50–1.44 (m, 1H). MS (APCI$^+$) Calc: 340.2, Found: 341.3 (M+1).

Step G: Preparation of 2-({4-[3-(Cyclobutyl-methyl-carbamoyl)-4-hydroxy-phenoxy]-3,5-dimethyl-phenyl}-hydrazono)-propionic acid ethyl ester To a solution of 5-(4-Amino-2,6-dimethyl-phenoxy)-N-cyclobutyl-2-hydroxy-N-methyl-benzamide (200 mg, 0.59 mmol) in a mixture of ethanol (2 mL) and hydrochloric acid (12M, 0.20 mL) at 0° C. was added slowly a solution of sodium nitrite (53 mg, 0.76 mmol) in water (0.5 mL). The resulting mixture was stirred at 0° C. for 30 minutes to furnish a diazonium solution, which was added dropwise into a solution of ethyl-2-methyl acetoacetate (102 mg, 0.71 mmol) in ethanol/1N NaOH (2 mL/2.6 mL) at 0° C. The reaction mixture was warmed to room temperature, stirred for 1 hour, then diluted with water (10 mL) and 1M hydrochloric acid (1 mL). The solution was extracted with ethyl acetate (3 times 15 mL). The combined organic extracts were washed with brine (30 mL), dried over Na$_2$SO$_4$, filtered, and concentrated to give the title compound (259 mg) as a reddish glass which was used in the next step without purification. MS (APCI$^+$) Calc: 453.2, Found: 454.3 (M+1).

Step H: Preparation of 5-[3-(Cyclobutyl-methyl-carbamoyl)-4-hydroxy-phenoxy]-4,6-dimethyl-1H-indole-2-carboxylic acid ethyl ester A mixture of p-toluenesulfonic acid (163 mg, 0.86 mmol) and 2-({4-[3-(Cyclobutyl-methyl-carbamoyl)-4-hydroxy-phenoxy]-3,5-dimethyl-phenyl}-hydrazono)-propionic acid ethyl ester (259 mg, 0.57 mmol) in toluene (2 mL) was heated to reflux. After vigorously stirring at reflux for 1 hour, the reaction mixture was then allowed to cool to room temperature. To which was added saturated aqueous NaHCO$_3$ (15 mL) and EtOAc (20 mL). The EtOAc layer was separated, washed with saturated NaHCO$_3$ (2 times 25 mL), brine (25 mL), dried over Na$_2$SO$_4$, filtered, and concentrated. The residue was purified by preparative TLC (4% MeOH in CH$_2$Cl$_2$) to afford the title compound (136 mg) as a yellow solid. $^1$H NMR (400 MHz, CDCl$_3$) δ9.45 (s, 1H), 8.89 (br s, 1H), 7.23 (s, 1H), 7.16 (s, 1H), 7.04 (dd, 1H), 6.97 (d, 1H), 6.42 (d, 1H), 4.46–4.38 (m, 3H), 2.93 (s, 3H), 2.36 (s, 3H), 2.26 (s, 3H), 2.22–2.01 (m, 2H), 1.74–1.54 (m, 2H), 1.43 (t, 3H), 1.36–1.20 (m, 2H). MS (APCI$^+$) Calc: 436.2, Found: 437.3 (M+1).

Step I: Preparation of 5-[3-(Cyclobutyl-methyl-carbamoyl)-4-hydroxy-phenoxy]-4,6-dimethyl-1H-indole-2-carboxylic acid To a solution of 5-[3-(Cyclobutyl-methyl-carbamoyl)-4-hydroxy-phenoxy]-4,6-dimethyl-1H-indole-2-carboxylic acid ethyl ester (102 mg, 0.23 mmol) in methanol (2 mL) at room temperature was added 3N potassium hydroxide (0.44 mL) and the mixture was stirred at room temperature for 7 hours. The reaction mixture was diluted with water (10 mL) and washed with EtOAc/Et$_2$O (1/1, 3 times 5 mL). The aqueous solution was acidified with hydrochloric acid and then extracted with ethyl acetate (3 times 5 mL). The combined organic extracts were dried over Na$_2$SO$_4$, filtered, and concentrated to afford the title compound (81 mg) as a yellow solid. $^1$H NMR (400 MHz, CD$_3$OD) δ11.08 (s, 1H), 7.15–7.14 (d, 2H), 6.76 (s+m, 2H), 6.33 (br s, 1H), 4.25–4.16 (m, 1H), 2.90 (s, 3H), 2.25 (s, 3H), 2.22–2.19 (m, 2H), 2.15 (s, 3H), 1.95–1.85 (m, 2H), 1.60–1.48 (m, 2H). MS (APCI$^+$) Calc: 408.2, Found: 409.2 (M+1).

Using the approproate starting materials, EXAMPLE 3-1 to EXAMPLE 3-16 were prepared in an analogous manner to the sequence of reactions described for EXAMPLE 3.

EXAMPLE 3-1

4,6-Dichloro-5-(4-hydroxy-3-methylcarbamoyl-phenoxy)-1H-indole-2-carboxylic acid $^1$H NMR (400 MHz, CD$_3$OD) δ8.62–8.56 (br s, 1H), 7.57 (s, 1H), 7.22 (d, 1H), 7.18 (s, 1H), 6.85–6.81 (m, 2H), 2.84 (s, 3H). MS (APCI$^+$) Calc:394.0, Found:395.1 (M+1).

EXAMPLE 3-2

5-(3-Butylcarbamoyl4-hydroxy-phenoxy)-4,6-dichloro-1H-indole-2-carboxylic acid $^1$H NMR (400 MHz, CD$_3$OD) δ8.68–8.62 (br t, 1H), 7.57 (s, 1H), 7.28 (d, 1H), 7.18 (s, 1H), 6.85–6.80 (m, 2H), 3.35–3.30 (m, 2H), 1.58–1.52 (m, 2H), 1.39–1.32 (m, 2H). 0.93 (t, 3H). MS (ES$^+$) Calc:436.1, Found:436.9 (M+1).

EXAMPLE 3-3

4,6-Dichloro-5-(4-hydroxy-3-isopropylcarbamoyl-phenoxy)-1H-indole-2-carboxylic acid $^1$H NMR (400 MHz, CD$_3$OD) δ8.49–8.44 (br d, 1H), 7.57 (s, 1H), 7.36 (d, 1H), 7.18 (s, 1H), 6.83–6.6.78 (m, 2H), 4.22–4.11 (m, 1H), 1.20 (d, 6H). MS (ES$^+$) Calc:422.0 Found:422.9 (M+1).

EXAMPLE 3-4

4,6-Dichloro-5-(4-hydroxy-3-nonylcarbamoyl-phenoxy)-1H-indole-2-carboxylic acid $^1$H NMR (400 MHz, CD$_3$OD) δ8.68–8.62 (br t, 1H), 7.57 (s, 1H), 7.28 (d, 1H), 7.18 (s, 1H), 6.86–6.80 (m, 2H), 3.34–3.30 (m, 2H), 1.60–1.51 (m, 2H), 1.39–1.32 (m, 2H), 1.35–1.25 (m, 12H), 0.87 (t, 3H). MS (APCI$^+$) Calc:506.1, Found:507.4 (M+1).

EXAMPLE 3-5

4,6-Dichloro-5-(3-cyclopentylcarbamoyl-4-hydroxy-phenoxy)-1H-indole-2-carboxylic acid $^1$H NMR (400 MHz, CD$_3$OD) δ8.58 (d, 1H), 7.57 (s, 1H), 7.37 (d, 1H), 7.18 (s, 1H), 6.83–6.77 (m, 2H), 4.32–4.22 (m, 1H), 2.06–1.92 (m, 2H), 1.78–1.47 (m, 6H). MS (APCI$^+$) Calc:448.1, Found:449.0 (M+1).

EXAMPLE 3-6

4,6-Dichloro-5-(3-cyclohexylcarbamoyl-4-hydroxy-phenoxy)-1H-indole-2-carboxylic acid $^1$H NMR (400 MHz, CD$_3$OD) δ8.53 (d, 1H), 7.57 (s, 1H), 7.36 (d, 1H), 7.18 (s, 1H), 6.84–6.78 (m, 2H), 3.91–3.79 (m, 1H), 1.96–1.85 (m, 2H), 1.79–1.70 (m, 2H), 1.69–1.60 (m, 1H), 1.42–1.19 (m, 5H). MS (APCI$^+$) Calc:462.1, Found:463.2 (M+1).

EXAMPLE 3-7

4,6-Dichloro-5-(3-cycloheptylcarbamoyl-4-hydroxy-phenoxy)-1H-indole-2-carboxylic acid $^1$H NMR (400 MHz, CD$_3$OD) δ8.59 (d, 1H), 7.57 (s, 1H), 7.36 (d, 1H), 7.18 (s, 1H), 6.85–6.73 (m, 2H), 4.09–3.98 (m, 1H), 1.98–1.87 (m, 2H), 1.75–1.48 (m, 10H). MS (APCI$^+$) Calc:476.1, Found:477.1 (M+1).

EXAMPLE 3-8

4,6-Dichloro-5-(3-cyclooctylcarbamoyl-4-hydroxy-phenoxy)-1H-indole-2-carboxylic acid $^1$H NMR (400 MHz, CD$_3$OD) δ8.60 (d, 1H), 7.57 (s, 1H), 7.38 (d, 1H), 7.18 (s, 1H), 6.83–6.77 (m, 2H), 4.16–4.03 (m, 1H), 1.90–1.78 (m, 2H), 1.77–1.50 (m, 12H). MS (APCI$^+$) Calc:490.1, Found:491.0 (M+1).

EXAMPLE 3-9

4,6-Dichloro-5-[4-hydroxy-3-(1-isopropyl-2-methyl-propylcarbamoyl)-phenoxy]-1H-indole-2-carboxylic acid $^1$H NMR (400 MHz, CD$_3$OD) δ8.41 (d, 1H), 7.57 (s, 1H), 7.38 (d, 1H), 7.18 (s, 1H), 6.90–6.78 (m, 2H), 3.68 (dt, 1H), 1.97–1.84 (m, 2H), 0.92–0.87 (m, 12H). MS (APCI$^+$) Calc:478.1, Found:479.4 (M+1).

EXAMPLE 3-10

4,6-Dichloro-5-[3-(cyclohexylmethyl-carbamoyl)-4-hydroxy-phenoxy]-1H-indole-2-carboxylic acid $^1$H NMR (400 MHz, CD$_3$OD) δ8.73–8.64 (m, 1H), 7.57 (s, 1H), 7.30 (d, 1H), 7.18 (s, 1H), 6.87–6.80 (m, 2H), 3.20–3.12 (m, 2H), 1.80–1.52 (m, 5H), 1.38–1.12 (m, 5H). MS (APCI$^+$) Calc:476.1, Found:477.2 (M+1).

EXAMPLE 3-11

4,6-Dichloro-5-[3-(1-cyclohexyl-(R)-ethylcarbamoyl)-4-hydroxy-phenoxy]-1H-indole-2-carboxylic acid $^1$H NMR (400 MHz, CD$_3$OD) δ8.49 (d, 1H), 7.57 (s, 1H), 7.36 (d, 1H), 7.18 (s, 1H), 6.87–6.75 (m, 2H), 3.98–3.86 (m, 1H), 1.82–1.60 (m, 5H), 1.50–1.00 (m, 5H), 1.14 (d, 3H). MS (ES$^-$) Calc: 490.1, Found: 488.9 (M−1).

EXAMPLE 3-12

4,6-Dichloro-5-[3-(1-cyclohexyl-(S)-ethylcarbamoyl)-4-hydroxy-phenoxy]-1H-indole-2-carboxylic acid $^1$H NMR (400 MHz, CD$_3$OD) δ8.49 (d, 1H), 7.57 (s, 1H), 7.36 (d, 1H), 7.18 (s, 1H), 6.87–6.75 (m, 2H), 3.98–3.86 (m, 1H), 1.82–1.60 (m, 5H), 1.50–1.00 (m, 5H), 1.14 (d, 3H). MS (ES$^-$) Calc:490.1, Found:488.9 (M−1).

EXAMPLE 3-13

4,6-Dichloro-5-{3-[(1-cyclohexyl-(R)-ethyl)-methyl-carbamoyl]-4-hydroxy-phenoxy}-1H-indole-2-carboxylic acid $^1$H NMR (400 MHz, CD$_3$OD) δ7.57 (s, 1H), 7.17 (d, 1H), 6.95 (dd, 1H), 6.82 (d, 1H), 6.21 (d, 1H), 3.25–3.17 (m, 1H),

EXAMPLE 3-14

4,6-Dichloro-5-{3-[(1-cyclohexyl-(S)-ethyl)-methyl-carbamoyl]-4-hydroxy-phenoxy}-1H-indole-2-carboxylic acid $^1$H NMR (400 MHz, CD$_3$OD) δ7.57 (s, 1H), 7.17 (d, 1H), 6.95 (dd, 1H), 6.82 (d, 1H), 6.21 (d, 1H), 3.25–3.17 (m, 1H), 2.77 (s, 3H), 1.84–1.53 (m, 5H), 1.40–1.00 (m, 5H), 1.13 (d, 3H). MS (ES$^+$) Calc:504.1, Found:504.9 (M+1).

EXAMPLE 3-15

4,6-Dichloro-5-[3-(cyclohexyl-methyl-carbamoyl)-4-hydroxy-phenoxy]-1H-indole-2-carboxylic acid $^1$H NMR (400 MHz, CD$_3$OD) δ7.56 (s, 1H), 7.16 (d, 1H), 6.87–6.75 (m, 2H), 6.40–6.31(m, 1H), 3.41–3.31 (m, 1H), 2.85 (brs, 3H), 1.80–1.40 (m, 8H), 1.17–1.00 (m, 2H), 1.13 (d, 3H). MS (ES$^+$) Calc:476.1, Found:476.9 (M+1).

EXAMPLE 3-16

4,6-Dichloro-5-[3-(cyclohexyl-methyl-methyl-carbamoyl)-4-hydroxy-phenoxy]-1H-indole-2-carboxylic acid $^1$H NMR (400 MHz, CD$_3$OD) δ7.56 (s, 1H), 7.17 (d, 1H), 6.93–6.87 (m, 1H), 6.82–6.75 (m, 1H), 6.35–6.29 (m, 1H), 3.09–2.99 (m, 2H), 2.94 (broad s, 3H), 1.80–1.00 (m, 10H). MS (ES$^+$) Calc:490.1, Found:490.9 (M+1).

EXAMPLE 4

4,6-Dichloro-5-(3-cyclobutylsulfamoyl-4-hydroxy-phenoxy)-1H-indole-2-carboxylic acid Step A Preparation of 5-(2,6-Dichloro-4-nitro-phenoxy)-2-methoxy-benzenesulfonyl chloride A solution of neat 2',6'-dichloro-4'-nitrodiphenyl ether (500 mg, 1.6 mmol) at 0° C. was treated with chlorosulfonic acid (0.88 mL, 7.5 mmol). The mixture was stirred for 5 minutes at 0° C. and allowed to warm to room temperature. After stirring for 30 minutes at room temperature, the reaction mixture was slowly dropped into ice water (100 mL) with stirring. The aqueous solution was extracted with ethyl acetate (3 times 75 mL). The combined organic extracts were washed with sodium bicarbonate (100 mL), water (100 mL), dried, and concentrated to afford the title compound as a brown solid. The crude product was used in the next step without purification. $^1$H NMR (400 MHz, CDCl$_3$) δ8.32 (s, 2H), 7.40 (d, 1H), 7.20–7.25 (dd, 1H), 7.09 (d, 1H), 4.04 (s, 3H). MS (APCI$^-$) Calc: 410.9, Found: 392.1 [M−1 for 5-(2,6-dichloro-4-nitro-phenoxy)-2-methoxy-benzenesulfonic acid].

Step B: Preparation of N-Cyclobutyl-5-(2,6-dichloro-4-nitro-phenoxy)-2-methoxy-benzenesulfonamide To a solution of 5-(2,6-Dichloro-4-nitro-phenoxy)-2-methoxy-benzenesulfonyl chloride (1.3 grams, 3.2 mmol) in methylene chloride (30 mL) at 0° C. was added triethylamine (0.58 mL, 4.1 mmol) followed by cyclobutylamine (0.27 mL, 3.2 mmol). After stirring at room temperature for 2 hours, the reaction mixture was quenched with 1N hydrochloric acid (25 mL) and extracted with methylene chloride (3 times 15 mL). The combined organic extracts were washed with 1N HCl (20 mL), saturated aqueous NaHCO$_3$ (2 times 20 mL), dried over Na$_2$SO$_4$, filtered, and concentrated. The residue was purified by column chromatography (30% ethyl acetate in hexane) to afford the title compound (531 mg). $^1$H NMR (400 MHz, CDCl$_3$) δ8.28 (s, 2H), 7.28 (d, 1H), 7.07–7.04 (dd, 1H), 6.98 (d, 1H), 5.26 (d, 1H), 3.96 (s, 3H), 3.71–3.69 (m, 1H), 1.99–1.92 (m, 2H), 1.74–1.68 (m, 2H), 1.57–1.48 (m, 2H). MS (APCI$^-$) Calc: 446.1, Found: 445.2 (M−1).

Step C: Preparation of N-Cyclobutyl-5-(2,6-dichloro-4-nitro-phenoxy)-2-hydroxy-benzenesulfonamide To a solution of N-Cyclobutyl-5-(2,6-dichloro-4-nitro-phenoxy)-2-methoxy-benzenesulfonamide (451 mg, 1.0 mmol) in methylene chloride (9 mL) at 0° C. was added boron tribromide (1M in methylene chloride, 2.0 mL, 2.0 mmol), and the mixture was stirred at room temperature for 2 hours. The reaction was quenched with water (25 mL) and stirred at room temperature for 1 hour, then extracted with ethyl acetate (3 times 40 mL). The combined organic extracts were washed with brine (15 mL), dried over Na$_2$SO$_4$, filtered, and concentrated. The residue was purified by column chromatography (5% ethyl acetate in CH$_2$Cl$_2$) to afford the title compound (403 mg). $^1$H NMR (400 MHz, CDCl$_3$) δ8.39 (s, 1H), 8.28 (s, 2H), 7.05–6.94 (m, 3H), 4.77 (d, 1H), 3.77–3.71 (m, 1H), 2.14–2.07 (m, 2H), 1.75–1.56 (m, 4H). MS (APCI$^-$) Calc: 432.1, Found: 431.2 (M−1).

Step D: Preparation of 5-(4-Amino-2,6-dichloro-phenoxy)-N-cyclobutyl-2-hydroxy-benzenesulfonamide To a solution of N-Cyclobutyl-5-(2,6-dichloro-4-nitro-phenoxy)-2-hydroxy-benzenesulfonamide (403 mg, 0.73 mmol) in ethanol (10 mL) at room temperature was added 10% palladium on carbon (60 mg), and the resulting mixture was placed on Parr shaker for 3 hours under 50 psi. hydrogen gas at room temperature. The reaction solution was filtered through Celite®, and the filtrate was concentrated to afford the title compound (379 mg) which was used in the next step without further purification. $^1$H NMR (400 MHz, CDCl$_3$) δ8.32 (s, 1H), 7.07–7.04 (dd, 1H), 6.95 (m, 2H), 6.67 (s, 2H), 4.68 (d, 1H), 3.81–3.68 (m, 1H), 2.16–2.08 (m, 2H), 1.7–1.58 (m, 4H). MS (APCI$^-$) Calc: 402.1, Found: 401.3 (M−1).

Step E: Preparation of 2-{[3,5-Dichloro-4-(3-cyclobutylsulfamoyl-4-hydroxy-phenoxy)-phenyl]-hydrazono}-propionic acid ethyl ester 2-{[3,5-Dichloro-4-(3-cyclobutylsulfamoyl-4-hydroxy-phenoxy)-phenyl]-hydrazono}-propionic acid ethyl ester was prepared from 5-(4-amino-2,6-dichloro-phenoxy)-N-cyclobutyl-2-hydroxy-benzenesulfonamide according to the procedure described in EXAMPLE 1, Step C. MS (APCI$^-$) Calc: 515.1, Found: 514.2 (M−1).

Step F: Preparation of 4,6-Dichloro-5-(3-cyclobutylsulfamoyl-4-hydroxy-phenoxy)-1H-indole-2-carboxylic acid ethyl ester The title compound (28 mg) was prepared from 2-{[3,5-Dichloro-4-(3-cyclobutylsulfamoyl-4-hydroxy-phenoxy)-phenyl]-hydrazono}-propionic acid ethyl ester (89 mg) according to the precedure described in Example 1, Step D. $^1$H NMR (400 MHz, CDCl$_3$) δ9.27 (s, 1H), 8.39 (br s, 1H), 7.40 (s, 1H), 7.22 (s, 1H), 7.12–7.09 (dd, 1H), 6.96 (d, 1H), 6.88 (d, 1H), 5.07 (d, 1H), 4.44–4.39 (q, 2H), 3.76–3.72 (m, 1H), 2.10–2.07 (m, 2H), 1.73–1.52 (m, 4H), 1.42 (t, 3H). MS (APCI$^-$) Calc: 498.0, Found: 497.1 (M−1).

Step G: Preparation of 4,6-Dichloro-5-(3-cyclobutylsulfamoyl-4-hydroxy-phenoxy)-1H-indole-2-carboxylic acid 4,6-Dichloro-5-(3-cyclobutylsulfamoyl-4-hydroxy-phenoxy)-1H-indole-2-carboxylic acid (19 mg) was prepared from 4,6-Dichloro-5-(3-cyclobutylsulfamoyl-4-hydroxy-phenoxy)-1H-indole-2-carboxylic acid ethyl ester (26 mg) according to the procedure described in EXAMPLE 1, Step E. $^1$H NMR (400 MHz, CD$_3$OD) δ7.58 (s, 1H), 7.19 (s, 1H), 7.02–6.99 (m, 2H), 6.90 (d, 1H), 3.68–3.60 (m, 1H), 1.95–1.84 (m, 2H), 1.81–1.76 (m, 2H), 1.56–1.45 (m, 2H). MS (APCI$^-$) Calc: 470.0, Found: 469.1 (M−1).

Using the appropriate starting materials, EXAMPLE 4-1 to 4-7 were prepared in an analogous manner to the sequence of reactions described for EXAMPLE 4 as appropriate.

EXAMPLE 4-1

4-Chloro-5-(3-cyclopropylsulfamoyl-4-hydroxy-phenoxy)-6-methyl-1H-indole-2-carboxylic acid ethyl ester MS (APCI$^-$) Calc:464.0, Found:463.2 (M−1).

EXAMPLE 4-2

4-Chloro-5-(3-cyclopropylsulfamoyl-4-hydroxy-phenoxy)-6-methyl-1H-indole-2-carboxylic acid MS (APCI$^-$) Calc: 436.0, Found: 435.1 (M−1).

EXAMPLE 4-3

5-(3-Cyclobutylsulfamoyl-4-hydroxy-phenoxy)-4,6-dimethyl-1H-indole-2-carboxylic acid $^1$H NMR (400 MHz, CD$_3$OD) δ7.18 (d, 2H), 6.93 (m, 2H), 6.86 (d, 1H), 3.64 (m, 1H), 5.47 (s, 1H), 2.28 (s, 3H), 2.17 (s, 3H), 1.97–1.75 (m, 4H), 1.46–1.56 (m, 2H). MS (APCI$^-$) Calc: 430.1, Found: 429.0 (M−1).

EXAMPLE 4-4

5-(3-Cyclopropylsulfamoyl-4-hydroxy-phenoxy)-4,6-dimethyl-1H-indole-2-carboxylic acid $^1$H NMR (400 MHz, CD$_3$OD) δ11.19 (s, 1H), 7.18 (d, 2H), 6.96 (d, 2H), 6.92 (d, 1H), 5.47 (s, 1H), 2.28 (s, 3H), 2.18 (s, 3H), 2.13 (m, 1H), 0.45 (dd, 4H). MS (APCI$^-$) Calc: 416.1, Found: 415.1 (M−1).

EXAMPLE 4-5

5-(3-Cyclopentylsulfamoyl-4-hydroxy-phenoxy)-4,6-dimethyl-1H-indole-2-carboxylic acid $^1$H NMR (400 MHz, CD$_3$OD) δ11.19 (s, 1H), 7.18 (d, 2H), 6.96 (m, 2H), 6.90 (d, 1H), 5.47 (s, 1H), 3.43 (m, 1H), 2.28 (s, 3H), 2.18 (s, 3H), 1.65–1.56 (m, 4H), 1.44–1.40 (m, 2H), 1.31–1.37 (m, 2H). MS (APCI$^-$) Calc: 444.1, Found: 443.1 (M−1).

EXAMPLE 4-6

5-(3-Cyclohexylsulfamoyl-4-hydroxy-phenoxy)-4,6-dimethyl-1H-indole-2-carboxylic acid $^1$H NMR (400 MHz, CD$_3$OD) δ11.19 (s, 1H), 7.18 (d, 2H), 6.99–6.89 (m, 3H), 2.92 (br s, 1H), 2.28 (s, 3H), 2.17 (s, 3H), 1.61 (d, 4H), 1.51 (d, 1H), 1.12 (m, 5H). MS (APCI$^-$) Calc: 458.1, Found: 457.1 (M−1).

EXAMPLE 4-7

4,6-Dichloro-5-(3-cyclopropylsulfamoyl-4-hydroxy-phenoxy)-1H-indole-2-carboxylic acid $^1$H NMR (400 MHz, CD$_3$OD) δ7.59 (d, 1H), 7.51 (s, 1H), 7.06–7.02 (m, 2H), 6.94 (m, 1H), 2.15 (m, 1H), 0.47 (m, 4H). MS (APCI$^-$) Calc: 456.0, Found: 454.9 (M−1).

EXAMPLE 5

4,6-Dichloro-5-(3-ethanesulfonyl-4-hydroxy-phenoxy)-1H-indole-2-carboxylic acid

Step A: Preparation of 5-(2,6-Dichloro-4-nitro-phenoxy)-2-methoxy-benzenesulfonyl chloride 5-(2,6-Dichloro-4-nitro-phenoxy)-2-methoxy-benzenesulfonyl chloride was prepared from 2',6'-dichloro-4'-nitrodiphenyl ether according to the procedure described in EXAMPLE 4, Step A.

Step B: Preparation of 5-(2,6-Dichloro-4-nitro-phenoxy)-2-methoxy-ethanesulfonyl-benzene To a solution of 5-(2,6-Dichloro-4-nitro-phenoxy)-2-methoxy-benzenesulfonyl chloride (5.2 grams, 12.6 mmol) in water (8 mL) at room temperature was added sodium sulfite (4.0 grams, 32 mmol) and sodium hydroxide (32%, w/v) until the solution was basic (pH approximately 9). The resulting mixture was stirred at 65° C. for 2 hours and overnight at room temperature. The mixture was acidified with 2N hydrochloric acid (20 mL) and extracted with ethyl acetate (3 times 80 mL). The combined organic extracts were dried over Na$_2$SO$_4$, filtered, and concentrated to give a sulfinic acid intermediate. To the sulfinic acid in a mixture of water (8 mL) and methanol (11 mL) at room temperature was added ethyl iodide (13 grams, 83 mmol) and sodium hydroxide (32%, w/v) until the solution was basic (pH approximately 9). The mixture was heated to reflux and stirred for 16 hours. The reaction solution was cooled to room temperature and extracted with ethyl acetate (4 times 100 mL). The combined organic extracts were washed with brine (200 mL), dried over Na$_2$SO$_4$, filtered, and concentrated. The crude product was purified by column chromatography (1% ethyl acetate in methylene chloride) to afford the title compound (2.0 g). $^1$H NMR (400 MHz, CDCl$_3$) δ8.30 (s, 1H), 7.38 (d, 1H), 7.14–7.11 (dd, 1H), 7.01 (d, 1H), 3.95 (s, 3H), 3.39–3.34 (q, 2H), 1.24 (t, 3H). MS (APCI$^-$) Calc: 405.0, Found: 404.1 (M−1).

Step C: Preparation of 4-(2,6-Dichloro-4-nitro-phenoxy)-2-ethanesulfonyl-phenol

To a solution of 5-(2,6-Dichloro-4-nitro-phenoxy)-2-methoxy-ethanesulfonyl-benzene (200 mg, 0.49 mmol) in methylene chloride (4 mL) at 0° C. was added boron tribromide (1M in methylene chloride, 1 mL, 1 mmol). The mixture was stirred at 0° C. for 5 minutes and then 2 hours at room temperature. The reaction was quenched with water (15 mL) and stirred at room temperature for 30 minutes, then extracted with ethyl acetate (3 times 15 mL). The combined organic extracts were washed with sodium bicarbonate (15 mL), dried over Na$_2$SO$_4$, filtered, and concentrated. The product (199 mg) was used in the next step without purification. $^1$H NMR (400 MHz, CDCl$_3$) δ8.28 (s, 1H), 7.13–7.10 (dd, 1H), 7.02 (d, 1H), 7.00 (d, 1H), 3.18–3.12 (q, 2H), 1.28 (t, 3H). MS (APCI$^-$) Calc: 391.0, Found: 390.0 (M−1).

Step D: Preparation of 4-(4-Amino-2,6-dichloro-phenoxy)-2-ethanesulfonyl-phenol 4-(4-Amino-2,6-dichloro-phenoxy)-2-ethanesulfonyl-phenol was prepared from 4-(2,6-Dichloro-4-nitro-phenoxy)-2-ethanesulfonyl-phenol according to the procedure described in EXAMPLE 4, Step D. $^1$H NMR (400 MHz, CDCl$_3$) δ7.11–7.08 (dd, 1H), 6.98–6.95 (m, 2H), 6.65 (s, 2H), 3.17–3.12 (q, 2H), 1.26 (t, 3H). MS (APCI$^-$) Calc: 361.0, Found: 360.0 (M−1).

Step E: Preparation of 2-{[3,5-Dichloro-4-(3-ethanesulfonyl-4-hydroxy-phenoxy)-phenyl]-hydrazono}-propionic acid ethyl ester 2-{[3,5-Dichloro-4-(3-ethanesulfonyl-4-hydroxy-phenoxy)-phenyl]-hydrazono}-propionic acid ethyl ester was prepared from 4-(4-Amino-2,6-dichloro-phenoxy)-2-ethanesulfonyl-phenol according to the procedure described in EXAMPLE 1, Step C. $^1$H NMR (400 MHz, CDCl$_3$) δ7.73 (s, 1H), 7.41 (s, 1H), 7.15 (d, 1H), 7.05 (d, 1H), 6.96 (d, 1H), 4.35–4.27 (q, 2H), 3.45–3.38 (q, 2H), 2.12 (s, 3H), 1.37 (t, 3H), 1.22 (t, 3H). MS (APCI$^-$) Calc: 474.0, Found: 472.7 (M−1).

Step F: Preparation of 4,6-Dichloro-5-(3-ethanesulfonyl-4-hydroxy-phenoxy)-1H-indole-2-carboxylic acid ethyl ester A mixture of p-toluenesulfonic acid (169 mg, 0.98 mmol) and 2-{[3,5-Dichloro-4-(3-ethanesulfonyl-4-hydroxy-phenoxy)-phenyl]-hydrazono}-propionic acid ethyl ester (310 mg, 0.65 mmol) in toluene (2.5 mL) was heated to reflux for 16 hours and then cooled to room temperature. The reaction mixture was diluted with ethyl acetate (25 mL), washed with saturated NaHCO$_3$ (3 times 10 mL), brine (10 mL), dried over Na$_2$SO$_4$, filtered, and concentrated. The residue was purified by preparative thin layer chromatography (4% methanol in methylene chloride) to afford the title compound (100 mg) as a tan solid. $^1$H NMR (400 MHz, CDCl$_3$) δ10.7 (s, 1H), 7.42 (s, 1H), 7.18 (d, 1H), 7.04–6.98 (m, 2H), 6.88 (d, 1H), 4.36–4.30 (q, 2H), 3.20–3.05 (q, 2H), 1.34 (t, 3H), 1.18 (t, 3H). MS (APCI$^-$) Calc: 457.0, Found: 456.1 (M−1).

Step G: Preparation of 4,6-Dichloro-5-(3-ethanesulfonyl-4-hydroxy-phenoxy)-1H-indole-2-carboxylic acid 4,6-Dichloro-5-(3-ethanesulfonyl-4-hydroxy-phenoxy)-1H-indole-2-carboxylic acid was prepared from 4,6-Dichloro-5-(3-ethanesulfonyl-4-hydroxy-phenoxy)-1H-indole-2-carboxylic acid ethyl ester according to the procedure described in EXAMPLE 1, Step E. $^1$H NMR (400 MHz, CD$_3$OD) δ7.57 (s, 1H), 7.17 (d, 1H), 7.06 (m, 2H), 6.94 (d, 1H), 3.39–3.34 (q, 2H), 1.13 (t, 3H). MS (APCI$^-$) Calc: 429.0, Found: 428.4 (M−1).

Using the appropriate starting materials, EXAMPLES 5-1 to 5-14 were prepared in an analogous manner to the sequence of reactions described for EXAMPLE 5 as appropriate.

EXAMPLE 5-1

4,6-Dichloro-5-(4-hydroxy-3-methanesulfonyl-phenoxy)-1H-indole-2-carboxylic acid ethyl ester $^1$H NMR (400 MHz, CD$_3$OD) δ7.42 (s, 1H), 7.18 (d, 1H), 7.09 (d, 1H), 6.98 (dd, 1H), 6.87 (d, 1H), 4.36–4.30 (q, 2H), 3.10 (s, 3H), 1.34 (t, 3H). MS (APCI$^-$) Calc: 443.0, Found: 442.1 (M−1).

EXAMPLE 5-2

4,6-Dichloro-5-(4-hydroxy-3-methanesulfonyl-phenoxy)-1H-indole-2-carboxylic acid $^1$H NMR (400 MHz, CD$_3$OD) δ7.56 (s, 1H), 7.16 (s, 1H), 7.12 (d, 1H), 7.04–7.01 (dd, 1H), 6.93 (d, 1H), 3.27 (s, 3H). MS (APCI$^-$) Calc: 415.0, Found: 414.1 (M−1).

EXAMPLE 5-3

5-(3-Cyclobutylmethanesulfonyl-4-hydroxy-phenoxy)-4,6-dimethyl-1H-indole-2-carboxylic acid ethyl ester $^1$H NMR (400 MHz, CDCl$_3$) δ9.26 (s, 1H), 7.21 (dd, 1H), 7.13 (s, 1H), 6.99 (dd, 1H), 6.98–6.91 (m, 2H), 4.11 (q, 1H), 3.20 (d, 2H), 2.73–2.61 (m, 1H), 2.30 (s, 3H), 2.18 (s, 3H), 2.04–1.96 (m, 2H), 1.94–1.81 (m, 1H), 1.80–1.65 (m, 3H), 1.41 (t, 3H). MS (APCI$^+$) Calc:457.2, Found: 458.2 (M+1).

EXAMPLE 5-4

5-(3-Cyclobutylmethanesulfonyl-4-hydroxy-phenoxy)-4,6-dimethyl-1H-indole-2-carboxylic acid $^1$H NMR (400 MHz, CD$_3$OD) δ11.14 (s, 1H), 7.19 (d, 1H), 7.16 (s, 1H), 7.01–6.97 (m, 2H), 6.91 (d, 1H), 3.43 (d, 2H), 2.57–2.51 (m, 1H), 2.26 (s, 3H), 2.16 (s, 3H), 1.90–1.79 (m, 3H), 1.78–1.68 (m, 3H). MS (APCI$^-$) Calc:429.1, Found: 428.3 (M−1).

EXAMPLE 5-5

4,6-Dichloro-5-(3-cyclobutylmethanesulfonyl-4-hydroxy-phenoxy)-1H-indole-2-carboxylic acid $^1$H NMR (400 MHz, CDCl$_3$/CD$_3$OD 10:1) δ7.47 (s, 1H), 7.23 (s, 1H), 7.06 (dd, 1H), 7.00 (d, 1H), 6.90 (d, 1H), 3.29 (d, 2H), 2.70–2.55 (m, 1H), 2.00–1.62 (m, 6H). MS (APCI$^-$) Calc:469.0, Found: 468.2 (M−1).

EXAMPLE 5-6

5-(3-Cyclohexylmethanesulfonyl-4-hydroxy-phenoxy)-4,6-dimethyl-1H-indole-2-carboxylic acid $^1$H NMR (400 MHz, CDCl$_3$) δ8.84 (b s,1H), 8.49 (bs, 1H), 7.35 (s, 1H), 7.15 (s, 1H), 6.93–7.03 (m, 3H), 2.97 (d, 2H), 2.32 (s, 3H), 2.21 (s, 3H), 2.11 (s, 1H), 1.92 (m, 1H), 1.78 (br d, 2H), 1.63 (m, 3H), 1.01–1.26 (m, 4H). MS (APCI$^-$) Calc: 457.2, Found: 456.1 (M−1).

EXAMPLE 5-7

5-(3-Cyclopentylmethanesulfonyl-4-hydroxy-phenoxy)-4,6-dimethyl-1H-indole-2-carboxylic acid $^1$H NMR (400 MHz, CD$_3$OD) δ11.19 (s, 1H), 7.18 (d, 2H), 7.02 (m, 2H), 6.94 (m, 1H), 3.41 (d, 2H), 2.27 (s, 3H), 2.17 (s, 3H), 2.03–2.11 (m, 1H), 1.71–1.76 (m, 2H), 1.57–1.63 (m, 2H), 1.45–1.54 (m, 2H), 1.13–1.22 (m, 2H). MS (APCI$^-$) $^{Calc:}$ 443.2, Found: 442.1 (M−1).

EXAMPLE 5-8

4,6-Dichloro-5-(3-cyclopropylmethanesulfonyl-4-hydroxy-phenoxy)-1H-indole-2-carboxylic acid $^1$H NMR (400 MHz, CD$_3$OD) δ7.59 (d, 1H), 7.18 (d, 1H), 7.09 (m, 2H), 6.95 (m, 1H), 3.28 (d, 2H), 0.87 (m, 1H), 0.46 (m, 2H), 0.15 (m, 2H). MS (APCI$^-$) Calc: 455.0, Found: 453.9 (M−1).

EXAMPLE 5-9

4,6-Dichloro-5-(3-cyclopentylmethanesulfonyl-4-hydroxy-phenoxy)-1H-indole-2-carboxylic acid $^1$H NMR (400 MHz, CD$_3$OD) δ7.58 (d, 1H), 7.18 (d, 1H), 7.06 (m, 2H), 6.96 (d, 2H), 3.41 (d, 2H), 2.07 (m, 1H), 1.73 (m, 2H), 1.58 (m, 2H), 1.46 (m, 2H), 1.21 (m, 2H). MS (APCI$^-$) Calc: 483.0, Found: 481.9 (M−1).

EXAMPLE 5-10

5-(3-Cyclobutylmethanesulfonyl-4-hydroxy-phenoxy)-1-isopropyl-4,6-dimethyl-1H-indole-2-carboxylic acid $^1$H NMR (400 MHz, CDCl$_3$/CD$_3$OD 10:1) δ8.89 (bs, <1H: partial D exchange, phenol), 7.35 (bs, 2H), 7.14 (bs, 1H), 6.96–6.86 (m, 2H), 4.65–4.58 (m, 1H), 3.46 (d, 2H), 2.73–2.64 (m, 1H), 2.32 (s, 3H), 2.20 (s, 3H), 2.05–1.65 (m, 6H), 1.40 (d, 6H). MS (APCI⁻) Calc:471.2, Found: 470.3 (M−1).

EXAMPLE 5-11

1-Benzyl-5-(3-cyclobutylmethanesulfonyl-4-hydroxy-phenoxy)-4,6-dimethyl-1H-indole-2-carboxylic acid ¹H NMR (400 MHz, CDCl₃/CD₃OD 10:1) δ7.31 (bs, 1H), 7.17–7.06 (m, 3H), 6.97–6.92 (m, 4H), 6.83–6.75 (m, 2H), 3.25 (d, 2H), 2.62–2.52 (m, 1H), 2.21 (s, 3H), 2.05 (s, 3H), 1.95–1.55 (m, 6H). MS (APCI⁻) Calc:519.2, Found: 518.1 (M−1).

EXAMPLE 5-12

5-(3-Cyclobutylmethanesulfonyl-4-hydroxy-phenoxy)-1,4,6-trimethyl-1H-indole-2-carboxylic acid ¹H NMR (400 MHz, CDCl₃/CD₃OD 10:1) δ7.27 (s, 1H), 7.05 (s, 1H), 6.97 (d, 1H), 6.90 (dd,1H), 6.83 (d, 1H), 3.99 (s, 3H), 3.28 (d, 2H), 2.70–2.55 (m, 1H), 2.24 (s, 3H), 2.18 (s, 3H), 1.98–1.62 (m, 6H). MS (APCI⁻) Calc:443.1, Found: 442.3 (M−1).

EXAMPLE 5-13

5-(3-Cyclobutylmethanesulfonyl-4-hydroxy-phenoxy)-1-ethyl-4,6-dimethyl-1H-indole-2-carboxylic acid ¹H NMR (400 MHz, CDCl₃/CD₃OD 10:1) δ7.28 (s, 1H), 7.06 (s, 1H), 6.99 (d, 1H), 6.92 (dd, 1H), 6.86 (d, 1H), 4.53 (q, 2H), 3.28 (d, 2H), 2.70–2.56 (m, 1H), 2.25 (s, 3H), 2.19 (s, 3H), 1.99–1.62 (m, 6H), 1.35 (t, 3H). MS (APCI⁻) Calc:457.2, Found: 456.4 (M−1).

EXAMPLE 5-14

5-(3-Cyclobutylmethanesulfonyl-4-hydroxy-phenoxy)-4,6-dimethyl-1-propyl-1H-indole-2-carboxylic acid ¹H NMR (400 MHz, CDCl₃/CD₃OD 10:1) δ7.29 (s, 1H), 7.05 (s, 1H), 7.00 (d, 1H), 6.92 (dd, 1H), 6.85 (d, 1H), 4.45 (dd, 2H), 3.28 (d, 2H), 2.71–2.59 (m, 1H), 2.25 (s, 3H), 2.19 (s, 3H), 2.00–1.64 (m, 8H), 0.90 (t, 3H). MS (APCI⁻) Calc:471.2, Found: 470.3 (M−1).

EXAMPLE 6

5-[3-(4-Fluoro-benzenesulfonyl)-4-hydroxy-phenoxy]-4,6-dimethyl-1H-indole-2-carboxylic acid Step A: 4-Fluoro-benzenesulfinic acid A mixture of 4-fluorobenzenesulfonyl chloride (50.0 grams 257 mmol), sodium sulfite (48.6 grams, 386 mmol), and sodium bicarbonate (108 grams, 1.28 mol) in water was heated to 100° C. The resulting solution was stirred for 1.5 hours at 100° C. then cooled to room temperature, acidified by careful addition of concentrated hydrochloric acid and extracted with ethyl acetate (3 times 250 ml). The combined organic extracts were washed with brine, dried over anhydrous sodium sulfate, filtered and concentrated to give the title compound of Step A as a solid (35.8 g). ¹H NMR (400 MHz, CDCl₃) δ9.78 (s, 1H), 7.77–7.67 (m, 2H), 7.21–7.15 (m, 2H). MS (APCI⁻) Calc.: 160.0, Found: 195.1 (M+35, Cl⁻ adduct).

Step B: 2-(4-Fluoro-benzenesulfonyl)-benzene-1,4-diol

A solution of benzoquinone (23.5 grams, 217 mmol) in ethanol (500 mL) was added at room temperature over 30 minutes to a solution of 4-fluoro-benzenesulfinic acid (34.8 grams, 217 mmol) in a mixture of ethanol (300 mL) and water (500 mL). The resulting solution was stirred for 2 hours at room temperature then diluted to 4L with warm water. The solution was kept at 4° C. for 62 hours and crystals formed. The crystalline solid was collected by filtration and washed with water (3 times 500 ml) and hexanes (2 times 500 ml) and dried to give the title compound of Step B (40.8 grams). ¹H NMR (400 MHz, CDCl₃) δ8.64 (bs, 1H), 7.96–7.92 (m, 2H), 7.22–7.16 (m, 2H), 7.08 (d, 1H), 6.97 (dd, 1H), 6.89 (d, 1H). MS (APCI⁻) Calc.: 268.0, Found: 267.1 (M−1).

Step C: 4-(2,6-Dimethyl-4-nitro-phenoxy)-2-(4-fluoro-benzenesulfonyl)-phenol

A solution of 2-(4-Fluoro-benzenesulfonyl)-benzene-1,4-diol (10.0 grams, 37 mmol) in dry 1-methyl-2-pyrrolidinone (100 mL) with 3° A molecular sieves (3.0 grams) was sparged with dry nitrogen for 15 minutes at room temperature. The solution was cooled to 0° C. and potassium bis(trimethylsilyl)amide (18.6 grams, 93.2 mmol) was added in a single portion to give a deep red suspension. The suspension was warmed to room temperature with continued sparging. 18-Crown-6 (10.8 grams 41.0 mmol) was added in a single portion and the resulting solution was cooled to 0° C. To the cooled suspension was added 2-chloro-1,3-dimethyl-5-nitro-benzene (8.30 grams, 44.7 mmol) to give a brown solution and sparging was ceased. The solution was allowed to warm to room temperature and stirred under dry nitrogen for 3 hours. The reaction mixture was poured into 1M hydrochloric acid (1 L) at 0° C. and extracted with ethyl acetate (3 times 300 ml). The combined organic extracts were washed with 1 M hydrochloric acid (4 times 1 L), brine (1 L), dried over anhydrous sodium sulfate and filtered. The filtrate was treated with activated carbon, filtered, and concentrated. The crude product was purified by chromatography on silica gel (150 grams) (methanol:hexanes:methylene chloride=1:9:10, 1.5 L) to give the title compound as a tan solid (11.4 grams). ¹H NMR (400 MHz, CD₃OD) δ8.05 (s, 1H), 8.00–7.95 (m, 2H), 7.28 (d, 1H), 7.26–7.20 (m, 2H), 6.93 (dd, 1H), 6.82 (d, 1H), 2.19 (s, 6H). MS (APCI⁻) Calc.: 417.1, Found: 416.0 (M−1).

Step D: 4-(4-Amino-2,6-dimethyl-phenoxy)-2-(4-fluoro-benzenesulfonyl)-phenol

To a solution of 4-(2,6-dimethyl-4-nitro-phenoxy)-2-(4-fluoro-benzenesulfonyl)-phenol (11.4 grams, 27.4 mmol) in a mixture of ethanol (200 mL and ethyl acetate (200 mL) was added catalyst (10% palladium on carbon, 2.3 grams). The mixture was hydrogenated under 45 psi at room temperature for 4 hours. The mixture was filtered through Celite and concentrated to give the title compound of Step D (10.5 grams) as a tan solid. The product was used in the next step without further purification. ¹H NMR (400 MHz, CD₃OD) δ7.98–7.92 (m, 2H), 7.29–7.22 (m, 2H), 7.21 (d, 1H), 6.92 (dd, 1H), 6.78 (d, 1H), 1.98 (s, 6H). MS (APCI⁻) Calc.:387.1, Found: 386.2 (M−1).

Step E: 5-[3-(4-Fluoro-benzenesulfonyl)-4-hydroxy-phenoxy]-4,6-dimethyl-1H-indole-2-carboxylic acid The title compound was prepared from 4-(4-Amino-2,6-dimethyl-phenoxy)-2-(4-fluoro-benzenesulfonyl)-phenol via Fischer indole synthhesis and basic hydrolysis as procedures described in EXAMPLE 1, Steps C, D and E. 1H NMR (400 MHz, CD3OD) δ11.16 (s, 1H), 7.98–7.93 (m, 2H), 7.28–7.17 (m, 5H), 6.93 (dd, 1H), 6.79 (d, 1H), 2.28 (s, 3H), 2.17 (s, 3H). MS (APCI⁻) Calc:455.1, Found: 454.2 (M−1).

Using the appropriate starting material, the following title compound of Example 6-1 was prepared in an analogous manner to the sequence of reactions described for Example 6

EXAMPLE 6-1

5-[3-(4-Fluoro-benzenesulfonyl)-4-hydroxy-phenoxy]-3,4,6-trimethyl-1H-indole-2-carboxylic acid $^1$H NMR (400 MHz, CD$_3$OD) δ10.62 (s, 1H), 7.92–7.97 (m, 2H), 7.18–7.24 (m, 3H), 7.10 (s, 1H), 6.90 (dd, 1H), 6.78 (d, 1H), 2.76 (s, 3H), 2.42 (s, 3H), 2.11 (s, 3H). MS (APCI$^-$) Calc: 469.1, Found: 468.0 (M−1).

EXAMPLE 7

5-[3-(4-Fluoro-benzoyl)-4-hydroxy-phenoxy]-4,6-dimethyl-1H-indole-2-carboxylic acid Step A: Preparation of [5-(2,6-Dimethyl-4-nitro-phenoxy)-2-methoxy-phenyl]-(4-fluoro-phenyl)-methanone

[5-(2,6-Dimethyl-4-nitro-phenoxy)-2-methoxy-phenyl]-(4-fluoro-phenyl)-methanone was prepared by titanium tetrachloride-catalyzed Friedel-Crafts acylation of 4-(4-methoxy-phenoxy)-3,5-dimethyl-nitrobenzene with p-fluorobenzoyl chloride according to the procedure described in the *J. Med. Chem.*, 1995, 695–707.

Step B: Preparation of [5-(4-Amino-2,6-dimethyl-phenoxy)-2-hydroxy-phenyl]-(4-fluoro-phenyl)-methanone

[5-(4-Amino-2,6-dimethyl-phenoxy)-2-hydroxy-phenyl]-(4-fluoro-phenyl)-methanone was prepared from [5-(2,6-Dimethyl-4-nitro-phenoxy)-2-methoxy-phenyl]-(4-fluoro-phenyl)-methanone via demethylation and hydrogenation according to the procedures described in EXAMPLE 1, Step B. $^1$H NMR (400 MHz, CDCl$_3$) δ11.4 (br s, 1H), 7.68–7.65 (m, 2H), 7.15–7.11 (m, 2H), 6.96 (s, 3H), 6.37 (s, 2H), 2.01 (s, 6H). MS (APCI$^-$) Calc:351.1, Found: 350.2 (M−1).

Step C: Preparation of 5-[3-(4-Fluoro-benzoyl)-4-hydroxy-phenoxy]-4,6-dimethyl-1H-indole-2-carboxylic acid 5-[3-(4-Fluoro-benzoyl)-4-hydroxy-phenoxy]-4,6-dimethyl-1H-indole-2-carboxylic acid was prepared from [5-(4-Amino-2,6-dimethyl-phenoxy)-2-hydroxy-phenyl]-(4-fluoro-phenyl)-methanone via Fischer indole synthesis and basic hydrolysis according to the procedures described in EXAMPLE 1, Steps C, D and E. $^1$H NMR (400 MHz, CD$_3$OD) δ11.1 (s, 1H), 7.61–7.57 (m, 2H), 7.12 (s, 2H), 7.06–7.02 (m, 3H), 6.92 (d, 1H), 6.67 (s, 1H), 2.25 (s, 3H), 2.15 (s, 3H). MS (APCI$^-$) Calc:419.1, Found: 418.2 (M−1).

Using the appropriate starting materials, EXAMPLES 7-1 was prepared in an analogous manner to the sequence of reactions described for EXAMPLE 7 as appropriate.

EXAMPLE 7-1

5-(3-Cyclopentylacetyl-4-hydroxy-phenoxy)-4,6-dimethyl-1H-indole-2-carboxylic acid $^1$H NMR (400 MHz, CDCl$_3$/CD$_3$OD 10:1) δ7.20 (s, 1H), 7.13–7.12 (m, 2H), 6.90–6.79 (m, 2H), 2.79 (d, 2H), 2.29 (s, 3H), 2.19 (s, 3H), 1.80–1.70 (m, 2H),1.60–1.51 (m, 4H), 1.15–1.01 (m, 2H). MS (APCI$^-$) Calc:407.2, Found: 406.4 (M−1).

EXAMPLE 8

5-{3-[(4-Fluoro-phenyl)-hydroxy-methyl]-4-hydroxy-phenoxy}-4,6-dimethyl-1H-indole-2-carboxylic acid Step A: Preparation of 5-{3-[(4-Fluoro-phenyl)-hydroxy-methyl]-4-hydroxy-phenoxy}-4,6-dimethyl-1H-indole-2-carboxylic acid ethyl ester To a solution of 5-[3-(4-Fluoro-benzoyl)-4-hydroxy-phenoxy]-4,6-dimethyl-1H-indole-2-carboxylic acid ethyl ester (20 mg, 0.045 mmol) in ethanol (1 mL) at room temperature was added sodium borohydride (3.4 mg, 0.089 mmol), and the resulting solution was stirred at room temperature for 1 hour. The reaction was quenched with 1M HCl.(10 mL), diluted with ethyl acetate (10 mL). The ethyl acetate layer was separated, washed with 1M HCl (2 times 10 mL), brine (10 mL), dried over Na$_2$SO$_4$, filtered, and concentrated. The residue was purified by preparative thin layer chromatography (4% methanol in methylene chloride) to afford the title compound (17.5 mg) as a solid. $^1$H NMR (400 MHz, CDCl$_3$) δ8.76 (s, 1H), 7.31–7.23 (m, 2H), 7.17 (s, 1H), 7.05 (s, 1H), 6.98 (t, 2H), 6.72 (d, 1H), 6.50 (dd, 1H), 6.36 (d, 1H), 5.84 (s, 1H), 4.40–4.34 (q, 2H), 2.25 (s, 3H), 2.14 (s, 3H), 1.38 (t, 3H). MS (APCI$^-$) Calc:449.2, Found: 448.3 (M−1).

Step B: Preparation of 5-{3-[(4-Fluoro-phenyl)-hydroxy-methyl]-4-hydroxy-phenoxy}-4,6-dimethyl-1H-indole-2-carboxylic acid To a solution of 5-{3-[(4-Fluoro-phenyl)-hydroxy-methyl]-4-hydroxy-phenoxy}-4,6-dimethyl-1H-indole-2-carboxylic acid ethyl ester (17.5 mg, 0.039 mmol) in a mixture of methanol (0.5 mL) and water (0.5 mL) at room temperature was added potassium hydroxide (3M, 0.078 mL), and the resulting solution was stirred at room temperature for 20 hours. The reaction solution was diluted with 0.1M potassium hydroxide (10 mL) and washed with ethyl acetate (3 times 5 mL). The aqueous solution was acidified with hydrochloric acid and then extracted with ethyl acetate (3 times 10 mL). The combined organic extracts were washed with brine, dried over Na$_2$SO$_4$, filtered, and concentrated to afford the title compound (13 mg) as a solid. $^1$H NMR (400 MHz, CD$_3$OD) δ11.0 (s, 1H), 7.30–7.26 (m, 2H), 7.12 (s, 2H), 6.93 (t, 2H), 6.73 (d, 1H), 6.60 (d, 2H), 6.43–6.40 (dd, H), 5.97 (s, 1H), 2.23 (s, 3H), 2.13 (s, 3H). MS (APCI$^-$) Calc:421. 1, Found: 420.1 (M−1).

Using the appropriate starting materials, EXAMPLES 8-1 was prepared in an analogous manner to the sequence of reactions described for EXAMPLE 7 as appropriate.

EXAMPLE 8-1

5-[3-(2-Cyclopentyl-1-hydroxy-ethyl)-4-hydroxy-phenoxy]-4,6-dimethyl-1H-indole-2-carboxylic acid $^1$H NMR (400 MHz, CD$_3$OD) δ7.21–7.16 (m, 2H), 6.70–6.62 (m, 2H), 6.49 (dd, 1H), 2.30 (s, 3H), 2.20 (s, 3H), 1.93–1.43 (m, 9H), 1.22–1.12 (m, 2H). MS (APCI$^-$) Calc:409.2, Found: 408.4 (M−1).

EXAMPLE 9

5-[3-(4-Fluoro-benzyl)-4-hydroxy-phenoxy]-4,6-dimethyl-1H-indole-2-carboxylic acid Step A: Preparation of 5-[3-(4-Fluoro-benzyl)-4-hydroxy-phenoxy]-4,6-dimethyl-1H-indole-2-carboxylic acid ethyl ester To a solution of 5-[3-(4-Fluoro-benzoyl)-4-hydroxy-phenoxy]-4,6-dimethyl-1H-indole-2-carboxylic acid ethyl ester (25 mg, 0.056 mmol) in a mixture of trifluoroacetic acid (0.2 mL) and methylene chloride (0.25 mL) at room temperature was added triethylsilane (0.09 mL, 0.56 mmol), and the resulting solution was stirred at room temperature for 18 hours. The reaction solution was poured into water (10 mL) and ethyl acetate (15 mL) was added. The organic phase was washed with saturated aqueous NaHCO$_3$ (2 times 10 mL), brine (10 mL), dried over Na$_2$SO$_4$, filtered, and concentrated. The residue was purified by preparative thin layer chromatography (30% ethyl acetate in hexane) to afford the title compound (17.8 mg) as a white solid. $^1$H NMR (400 MHz, CDCl$_3$) δ8.84 (s, 1H), 7.21 (s, 1H), 7.15–7.09(m, 3H), 6.94 (t, 2H), 6.63 (d, 1H), 6.58 (d, 1H), 6.45–6.42 (dd, 1H), 4.43–4.37 (q, 2H), 3.86 (s, 2H), 2.31 (s, 3H), 2.20 (s, 3H), 1.41 (t, 3H). MS (APCI$^-$) Calc:433.2, Found: 432.1 (M–1).

Step B: Preparation of 5-[3-(4-Fluoro-benzyl)-4-hydroxy-phenoxy]-4,6-dimethyl-1H-indole-2-carboxylic acid 5-[3-(4-Fluoro-benzyl)-4-hydroxy-phenoxy]-4,6-dimethyl-1H-indole-2-carboxylic acid was prepared from 5-[3-(4-Fluoro-benzyl)-4-hydroxy-phenoxy]-4,6-dimethyl-1H-indole-2-carboxylic acid ethyl ester according to the procedure described in EXAMPLE 8, Step B. $^1$H NMR (400 MHz, CD$_3$OD) δ11.0 (s, 1H), 7.13–7.09 (m, 4H), 6.87 (t, 2H), 6.61 (d, 1H), 6.39–6.31 (m, 2H), 3.78 (s, 2H), 2.20 (s, 3H), 2.10 (s, 3H). MS (APCI$^-$) Calc:405.1, Found: 404.2 (M–1).

What is claimed is:

1. A compound of the formula

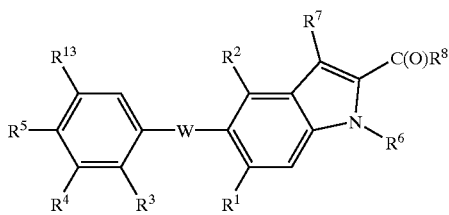

I or the pharmaceutically acceptable salt thereof; wherein

W is oxygen, CH$_2$, CF$_2$, NR$^{12}$, S(O)$_m$ wherein m is 0, 1 or 2;

R$^1$, R$^2$, and R$^3$ are each independently selected from the group consisting of hydrogen, halo, cyano, trifluoromethyl, trifluomethoxy and (C$_1$–C$_6$)alkyl;

R$^4$ is hydrogen, halo, cyano, (C$_1$–C$_{12}$)alkyl, (C$_2$–C$_{12}$)alkenyl, (C$_2$–C$_{12}$)alkynyl, (C$_3$–C$_{10}$)cycloalkyl, (C$_3$–C$_{10}$)cycloalkyl(C$_1$–C$_6$)alkyl, —OR$^9$, —S(O)$_2$NR$^{10}$R$^{11}$, —C(O)NR$^{10}$R$^{11}$, —C(O)R$^{10}$, —CH(OH)R$^{10}$, —NR$^{12}$C(O)R$^{10}$, —NR$^{12}$C(O)NR$^{10}$R$^{11}$, —NR$^{12}$S(O)$_2$R$^{10}$ or —S(O)$_n$R$^{10}$ wherein n is 0, 1 or 2;

R$^5$ is hydroxy, or, (C$_1$–C$_4$)alkoxy;

R$^6$ is hydrogen, —C(O)CH$_3$, (C$_1$–C$_6$)alkyl, or phenyl (C$_1$–C$_6$)alkyl;

R$^7$ is hydrogen or (C$_1$–C$_6$)alkyl;

R$^8$ is OR$^{12}$ or NR$^9$R$^{12}$;

R$^9$ for each occurrence is independently hydrogen, (C$_1$–C$_{12}$)alkyl, (C$_3$–C$_{10}$)cycloalkyl;

R$^{10}$ for each occurrence is independently hydrogen, (C$_1$–C$_{12}$)alkyl, (C$_2$–C$_{12}$)alkenyl, (C$_2$–C$_{12}$)alkynyl, (C$_3$–C$_{10}$)cycloalkyl, (C$_3$–C$_9$)cycloalkyl(C$_1$–C$_6$)alkyl;

R$^{11}$ for each occurrence is independently hydrogen, (C$_1$–C$_6$)alkyl, (C$_3$–C$_{10}$) cycloalkyl or (C$_3$–C$_9$)cycloalkyl(C$_1$–C$_6$)alkyl;

R$^{12}$ for each occurrence is independently hydrogen or (C$_1$–C$_6$)alkyl; and R$^{13}$ is hydrogen, halo or (C$_1$–C$_6$)alkyl.

2. A compound according to claim 1, wherein W is oxygen.

3. A compound according to claim 1, wherein R$^1$ and R$^2$ are each independently halo, cyano or (C$_1$–C$_6$)alkyl.

4. A compound according to claim 1, wherein R$^3$ is hydrogen or (C$_1$–C$_4$)alkyl.

5. A compound according to claim 1, wherein R$^4$ is halo, (C$_1$–C$_{12}$)alkyl, —C(O)NR$^{10}$R$^{11}$, —S(O)$_2$NR$^{10}$R$^{11}$, —S(O)$_2$R$^{10}$, —C(O)R$^{10}$, or —CH(OH)R$^{10}$.

6. A compound according to claim 1, wherein R$^{10}$ is hydrogen, (C$_1$–C$_8$)alkyl, (C$_3$–C$_9$)cycloalkyl, (C$_3$–C$_9$)cycloaklyl(C$_1$–C$_6$)alkyl, (C$_6$–C$_{10}$)aryl or halo(C$_6$–C$_{10}$)aryl.

7. A compound according to claim 1, wherein R$^{11}$ is hydrogen, (C$_1$–C$_6$)alkyl, (C$_3$–C$_9$)cycloalkyl or (C$_3$–C$_9$)cycloalkyl(C$_1$–C$_6$)alkyl.

8. A compound according to claim 1, wherein R$^5$ is hydroxy.

9. A compound according to claim 1, wherein R$^6$ is hydrogen or (C$_1$–C$_6$)alkyl.

10. A compound according to claim 1, wherein R$^7$ is hydrogen or (C$_1$–C$_4$)alkyl.

11. A compound according to claim 1, wherein R$^8$ is OR$^{12}$ wherein R$^{12}$ is hydrogen or (C$_1$–C$_6$)alkyl.

12. A compound according to claim 1, wherein R$^{13}$ is hydrogen, chloro, fluoro, methyl or isopropyl.

13. A compound according to claim 1, wherein W is oxygen; R$^1$ and R$^2$ are each independently halo, cyano or (C$_1$–C$_6$)alkyl; R$^3$ is hydrogen or (C$_1$–C$_4$)alkyl; R$^4$ is halo; R$^5$ is hydroxy; R$^6$ is hydrogen or (C$_1$–C$_6$)alkyl; R$^7$ is hydrogen or (C$_1$–C$_4$)alkyl, R$^8$ is OR$^{12}$ wherein R$^{12}$ is hydrogen or (C$_1$–C$_6$)alkyl, and R$^{13}$ is hydrogen, chloro, fluoro, methyl or isopropyl.

14. A compound according to claim 1, wherein W is oxygen; R$^1$ and R$^2$ are each independently halo, cyano or (C$_1$–C$_6$)alkyl; R$^3$ is hydrogen or (C$_1$–C$_4$)alkyl; R$^4$ is (C$_1$–C$_{12}$)alkyl; R$^5$ is hydroxy; R$^6$ is hydrogen or (C$_1$–C$_6$) alkyl; R$^7$ is hydrogen or (C$_1$–C$_4$)alkyl; R$^8$ is OR$^{12}$ wherein R$^{12}$ is hydrogen or (C$_1$–C$_6$)alkyl, and R$^{13}$ is hydrogen, chloro, fluoro, methyl or isopropyl.

15. A compound according to claim 1, wherein W is oxygen; R$^1$ and R$^2$ are each independently halo, cyano or (C$_1$–C$_6$)alkyl; R$^3$ is hydrogen or (C$_1$–C$_4$)alkyl; R$^4$ is —C(O)NR$^{10}$R$^{11}$; R$^{10}$ is hydrogen, (C$_1$–C$_8$)alkyl, (C$_3$–C$_9$)cycloalkyl, (C$_3$–C$_9$)cycloalkyl(C$_1$–C$_6$)alkyl; R$^{11}$ is hydrogen, (C$_1$–C$_6$)alkyl, (C$_3$–C$_9$)cycloalkyl or (C$_3$–C$_9$)cycloalkyl(C$_1$–C$_6$)alkyl; R$^5$ is hydroxy; R$^6$ is hydrogen or (C$_1$–C$_6$)alkyl; R$^7$ is hydrogen or (C$_1$–C$_4$)alkyl; R$^8$ is OR$^{12}$ wherein R$^{12}$ is hydrogen or (C$_1$–C$_6$)alkyl, and R$^{13}$ is hydrogen, chloro, fluoro, methyl or isopropyl.

16. A compound according to claim 1, wherein W is oxygen; R$^1$ and R$^2$ are each independently halo, cyano or (C$_1$–C$_6$)alkyl; R$^3$ is hydrogen or (C$_1$–C$_4$)alkyl; R$^4$ is —S(O)$_2$NR$^{10}$R$^{11}$; R$^{10}$ is hydrogen, (C$_1$–C$_8$)alkyl, (C$_3$–C$_9$)cycloalkyl, (C$_3$–C$_9$)cycloalkyl(C$_1$–C$_6$)alkyl; R$^{11}$ is hydrogen, (C$_1$–C$_6$)alkyl, (C$_3$–C$_9$)cycloalkyl or (C$_3$–C$_9$)cycloalkyl(C$_1$–C$_6$)alkyl; R$^5$ is hydroxy; R$^6$ is hydrogen or (C$_1$–C$_6$)alkyl; R$^7$ is hydrogen or (C$_1$–C$_4$)alkyl; R$^8$ is OR$^{12}$ wherein R$^{12}$ is hydrogen or (C$_1$–C$_6$)alkyl, and R$^{13}$ is hydrogen, chloro, fluoro, methyl or isopropyl.

17. A compound according to claim 1, wherein W is oxygen; R$^1$ and R$^2$ are each independently halo, cyano or (C$_1$–C$_6$)alkyl; R$^3$ is hydrogen or (C$_1$–C$_4$)alkyl; R$^4$ is —S(O)$_2$R$^{10}$; R$^{10}$ is hydrogen, (C$_1$–C$_8$)alkyl, (C$_3$–C$_9$)cycloalkyl, (C$_3$–C$_9$)cycloalkyl(C$_1$–C$_6$)alkyl; R$^5$ is hydroxy; R$^6$ is hydrogen or (C$_1$–C$_6$)alkyl; R$^7$ is hydrogen or (C$_1$–C$_4$)alkyl; R$^8$ is OR$^{12}$ wherein R$^{12}$ is hydrogen or (C$_1$–C$_6$)alkyl, and R$^{13}$ is hydrogen, chloro, fluoro, methyl or isopropyl.

18. A compound according to claim 1, wherein W is oxygen; R$^1$ and R$^2$ are each independently halo, cyano or (C$_1$–C$_6$)alkyl; R$^3$ is hydrogen or (C$_1$–C$_4$)alkyl; R$^4$ is —C(O)R$^{10}$; R$^{10}$ is hydrogen, (C$_1$–C$_8$)alkyl, (C$_3$–C$_9$)cycloalkyl, (C$_3$–C$_9$)cycloalkyl(C$_1$–C$_6$)alkyl; R$^5$ is hydroxy; R$^6$ is hydrogen or (C$_1$–C$_6$)alkyl; R$^7$ is hydrogen or (C$_1$–C$_4$)alkyl; R$^8$ is OR$^{12}$ wherein R$^{12}$ is hydrogen or (C$_1$–C$_6$)alkyl, and R$^{13}$ is hydrogen, chloro, fluoro, methyl or isopropyl.

19. A compound according to claim 1, wherein W is oxygen; R$^1$ and R$^2$ are each independently halo, cyano or (C$_1$–C$_6$)alkyl; R$^3$ is hydrogen or (C$_1$–C$_4$)alkyl; R$^4$ is —CH(OH)R$^{10}$; R$^{10}$ is hydrogen, (C$_1$–C$_8$)alkyl, (C$_3$–C$_9$)cycloalkyl, (C$_3$–C$_9$)cycloalkyl(C$_1$–C$_6$)alkyl; R$^5$ is hydroxy; R$^6$ is hydrogen or (C$_1$–C$_6$)alkyl; R$^7$ is hydrogen or (C$_1$–C$_4$)alkyl; R$^8$ is OR$^{12}$ wherein R$^{12}$ is hydrogen or (C$_1$–C$_6$)alkyl, and R$^{13}$ is hydrogen, chloro, fluoro, methyl or isopropyl.

20. A compound according to claim 1, selected from the group consisting of:
    5-(4-Hydroxy-3-isopropyl-phenoxy)-4,6-dimethyl-1H-indole-2-carboxylic acid;
    4,6-Dichloro-5-(4-hydroxy-3-isopropyl-phenoxy)-1H-indole-2-carboxylic acid;
    5-(3-sec-butyl-4-hydroxy-phenoxy)-4,6-dimethyl-1H-indole-2-carboxylic acid;
    5-[3-(4-Fluoro-benzyl)-4-hydroxy-phenoxyl]-4,6-dimethyl-1H-indole-2-carboxylic acid;
    5-{3-[(4-Fluoro-phenyl)-hydroxy-methyl]-4-hydroxy-phenoxy}-4,6-dimethyl-1H-indole-2-carboxylic acid;
    5-[3-(2-Cyclopentyl-1-hydroxy-ethyl)-4-hydroxy-phenoxyl]-4,6-dimethyl-1H-indole-2-carboxylic acid;
    5-[3-(4-Fluoro-benzoyl)-4-hydroxy-phenoxyl]-4,6-dimethyl-1H-indole-2-carboxylic acid;
    5-[3-(Cyclobutyl-methyl-carbamoyl)-4-hydroxy-phenoxyl]-4,6-dimethyl-1H-indole-2-carboxylic acid;
    5-(3-Cyclobutylmethanesulfonyl-4-hydroxy-phenoxy)-4,6-dimethyl-1H-indole-2-carboxylic acid;
    4,6-Dichloro-5-(3-cyclobutylmethanesulfonyl-4-hydroxy-phenoxy)-1H-indole-2-carboxylic acid;
    4,6-Dichloro-5-(4-hydroxy-3-isopropyl-phenoxy)-1-methyl-1H-indole-2-carboxylic acid;
    4,6-Dichloro-5-(4-hydroxy-3-isopropyl-phenoxy)-3-methyl-1H-indole-2-carboxylic acid;
    5-[3-(4-Fluoro-benzenesulfonyl)-4-hydroxy-phenoxy]-4,6-dimethyl-1H-indole-2-carboxylic acid;
    5-[3-(4-Fluoro-benzenesulfonyl)-4-hydroxy-phenoxy]-3,4,6-trimethyl-1H-indole-2-carboxylic acid;
    4,6-Dichloro-5-(3-cyclobutylsulfamoyl-4-hydroxy-phenoxy)-1H-indole-2-carboxylic acid;
    4-Chloro-5-(3-cyclopropylsulfamoyl-4-hydroxy-phenoxy)-5-methyl-1H-indole-2-carboxylic acid;
    4,6-Dichloro-5-[4-hydroxy-3-(1-isopropyl-2-methyl-propylcarbamoyl-phenoxy]-1H-indole-2-carboxylic acid;
    5-[3-(4-Fluoro-benzenesulfonyl)-4-hydroxy-phenoxy]-1,4,6-trimethyl-1H-indole-2-carboxylic acid;
    5-3-[(4-Fluoro-phenyl)-hydroxy-methyl]-4-hydroxy-phenoxy)-3,4,6-trimethyl-1H-indole-2-carboxylic acid;
    5-[3-(4-Fluoro-benzyl)-4-hydroxy-phenoxy]-3,4,6-trimethyl-1H-indole-2-carboxylic acid;
    5-(3-Cyclopentylmethanesulfonyl-4-hydroxy-phenoxy)-4,6-dimethyl-1H-indole-2-carboxylic acid;
    4,6-Dichloro-5-(3-cyclopropylsulfamoyl-4-hydroxy-phenoxy)-1H-indole-2-carboxylic acid;
    5-(3-Cyclohexylmethanesulfonyl-4-hydroxy-phenoxy)-4,6-dimethyl-1H-indole-2-carboxylic acid;
    5-(3-Cyclopropylsulfamoyl-4-hydroxy-phenoxy)-4,6-dimethyl-1H-indole-2-carboxylic acid;
    5-(4-Hydroxy-3-isopropyl-phenoxy)-3,4,6-trimethyl-1H-indole-2-carboxylic acid;
    5-(4-Hydroxy-3-isopropyl-phenoxy)-1,4,6-trimethyl-1H-indole-2-carboxylic acid;
    4,6-Dichloro-5-[3-(4-fluoro-benzenesulfonyl)-4-hydroxy-phenoxy]-1H-indole-2-carboxylic acid;
    4,6-Dichloro-5-[3-(4-fluoro-benzenesulfonyl-4-hydroxy-phenoxy]-3-methyl-1H-indole-2-carboxylic acid;
    5-(3-Cyclobutylsulfamoyl-4-hydroxy-phenoxy)-4,6-dimethyl-1H-indole-2-carboxylic acid;
    5-[4-Hydroxy-3-(1-isopropyl-2-methyl-propylcarbamoyl)-phenoxy]-4,6-dimethyl-1H-indole-2-carboxylic acid;
    4,6-Dichloro-5-3-[(4-fluoro-phenyl)-hydroxy-methyl]-4-hydroxy-phenoxy-1H-indole-2-carboxylic acid;
    5-(4-Hydroxy-2,3-dimethyl-phenoxy)-4,6-dimethyl-1H-indole-2-carboxylic acid, and;
    4,6-Dichloro-5-(4-hydroxy-2,3-dimethyl-phenoxy)-1H-indole-2-carboxylic acid.

21. A method for treating obesity, in a mammal, including a human, comprising administering to said mammal an amount of a compound of claim 1 or a pharmaceutically acceptable salt thereof, effective in treating such a condition.

22. A pharmaceutical composition for treating obesity, in a mammal, including a human, comprising an amount of a compound of claim 1 or a pharmaceutically acceptable salt thereof, effective in such treatments and a pharmaceutically acceptable carrier.

23. A compound according to claim 1, selected from the group consisting of:
    5-(3-sec-Butyl-4-hydroxy-phenoxy)-1,4,6-trimethyl-1H-indole-2carboxylic acid;
    4,6-Dichloro-5-(4-hydroxy-3-methylcarbamoyl-phenoxy)-1H-indole-2-carboxylic acid;
    5-(3-Butylcarbamoyl-4-hydroxy-phenoxy)-4,6-dichloro-1H-indole-2-carboxylic acid;
    4,6-Dichloro-5-(4-hydroxy-3-isopropylcarbamoyl-phenoxy)-1H-indole-2-carboxylic acid;
    4,6-Dichloro-5-(4-hydroxy-3-nonylcarbamoyl-phenoxy)-1H-indole-2-carboxylic acid;
    4,6-Dichloro-5-(3-cyclopentylcarbamoyl-4-hydroxy-phenoxy)-1H-indole-2-carboxylic acid;
    4,6-Dichloro-5-(3-cyclohexylcarbamoyl-4-hydroxy-phenoxy)-1H-indole-2-carboxylic acid;
    4,6-Dichloro-5-(3-cycloheptylcarbamoyl-4-hydroxy-phenoxy)-1H-indole-2-carboxylic acid;
    4,6-Dichloro-5-(3-cyclooctylcarbamoyl-4-hydroxy-phenoxy)-1H-indole-2-carboxylic acid;
    4,6-Dichloro-5-[3-(cyclohexylmethyl-carbamoyl)-4-hydroxy-phenoxy]-1H-indole-2-carboxylic acid;
    4,6-Dichloro-5-[3-(1-cyclohexyl-(R)-ethylcarbamoyl)-4-hydroxy-phenoxy]-1H-indole-2 carboxylic acid;
    4,6-Dichloro-5-[3-(1-cyclohexyl-(S)-ethylcarbamoyl)-4-hydroxy-phenoxy]-1H-indole-2-carboxylic acid;
    4,6-Dichloro-5-{3-[(1-cyclohexyl-(R)-ethyl)-methyl-carbamoyl]-4-hydroxy-phenoxy}-1H-indole-2-carboxylic acid;
    4,6-Dichloro-5-{3-[(1-cyclohexyl-(S)-ethyl)-methyl-carbamoyl]-4-hydroxy-phenoxy}-1H-indole-2-carboxylic acid;
    4,6-Dichloro-5-[3-(cyclohexyl-methyl-carbamoyl)-4-hydroxy-phenoxy]-1H-indole-2-carboxylic acid;

4,6-Dichloro-5-[3-(cyclohexylmethyl-methyl-carbamoyl)-4-hydroxy-phenoxy]-1H-indole-2-carboxylic acid;

4,6-Dichloro-5-(3-ethanesulfonyl-4-hydroxy-phenoxy)-1H-indole-2-carboxylic acid;

6-Dichloro-5-(4-hydroxy-3-methanesulfonyl-phenoxy)-1H-indole-2-carboxylic acid ethyl ester;

4,6-Dichloro-5-(4-hydroxy-3-methanesulfonyl-phenoxy)-1H-indole-2-carboxylic acid;

4,6-Dichloro-5-(3-cyclopropylmethanesulfonyl-4-hydroxy-phenoxy)-1H-indole-2-carboxylic acid;

4,6-Dichloro-5-(3-cyclopentylmethanesulfonyl-4-hydroxy-phenoxy)-1H-indole-2-carboxylic acid;

5-(3-Cyclobutylmethanesulfonyl-4-hydroxy-phenoxy)-1-isopropyl-4,6-dimethyl-1H-indole-2-carboxylic acid;

1-Benzyl-5-(3-cyclobutylmethanesulfonyl-4-hydroxy-phenoxy)-4,6-dimethyl-1H-indole-2-carboxylic acid;

5-(3-Cyclobutylmethanesulfonyl-4-hydroxy-phenoxy)-1,4,6-trimethyl-1H-indole-2-carboxylic acid;

5-(3-Cyclobutylmethanesulfonyl-4-hydroxy-phenoxy)-1-ethyl-4,6-dimethyl-1H-indole-2-carboxylic acid; and;

5-(3-Cyclopentylacetyl-4-hydroxy-phenoxy)-4,6-dimethyl-1H-indole-2-carboxylic acid.

\* \* \* \* \*